(12) United States Patent
Inal et al.

(10) Patent No.: US 12,144,614 B2
(45) Date of Patent: Nov. 19, 2024

(54) N-TYPE POLYMER BASED ELECTROCHEMICAL DEVICE FOR DIRECT ENZYMATIC METABOLITE SENSING AND METHODS OF MAKING AND USING

(71) Applicants: King Abdullah University of Science and Technology, Thuwal (SA); Institut Mines Telecom, Palaiseau (FR); Imperial College London, London (GB)

(72) Inventors: Sahika Inal, Thuwal (SA); Anna-Maria Pappa, Cambridge (GB); Alexander Giovannitti, London (GB)

(73) Assignees: King Abdullah University of Science and Technology, Thuwal (SA); Institut Mines Telecom, Palaiseau (FR); Imperial College London, London (GB)

( * ) Notice: Subject to any disclaimer, the term of this patent is extended or adjusted under 35 U.S.C. 154(b) by 509 days.

(21) Appl. No.: 16/962,971

(22) PCT Filed: Jan. 18, 2019

(86) PCT No.: PCT/IB2019/050443
§ 371 (c)(1),
(2) Date: Jul. 17, 2020

(87) PCT Pub. No.: WO2019/142146
PCT Pub. Date: Jul. 25, 2019

(65) Prior Publication Data
US 2021/0128030 A1   May 6, 2021

Related U.S. Application Data

(60) Provisional application No. 62/618,794, filed on Jan. 18, 2018.

(51) Int. Cl.
*A61B 5/145* (2006.01)
*A61B 5/1486* (2006.01)
*C12Q 1/00* (2006.01)

(52) U.S. Cl.
CPC ...... *A61B 5/14532* (2013.01); *A61B 5/14546* (2013.01); *A61B 5/14865* (2013.01);
(Continued)

(58) Field of Classification Search
CPC ............ A61B 5/14532; A61B 5/14546; A61B 5/14865; A61B 2562/125; C12Q 1/002; C12Q 1/005; C12Q 1/006
See application file for complete search history.

(56) References Cited

U.S. PATENT DOCUMENTS

2009/0040587 A1* 2/2009 Kugler .................... G02F 1/163
                                                    257/253
2012/0078072 A1* 3/2012 Roesicke ........... A61B 17/3468
                                                    600/309

(Continued)

FOREIGN PATENT DOCUMENTS

WO    2011022121    2/2011
WO    2014096407    6/2014

(Continued)

OTHER PUBLICATIONS

Giovannitti, Alexander, et al. "N-type organic electrochemical transistors with stability in water." Nature communications 7.1 (2016): 1-10. (Year: 2016).*

(Continued)

*Primary Examiner* — David J. McCrosky
*Assistant Examiner* — Meghan R Kumar
(74) *Attorney, Agent, or Firm* — PABST PATENT GROUP LLP

(57) ABSTRACT

N-type polymer based electrochemical devices include one or more source electrodes, one or more drain electrodes, one (Continued)

or more channels, a gate electrode, and an electrolyte solution are disclosed. The channels include one or more n-type polymers and one or more enzymes. The gate electrode includes one or more n-type polymers and one or more enzymes. The source and the drain electrodes are electrically connected by the corresponding channel. The electrolyte solution contains one or more metabolites capable of reacting with the one or more enzymes in the channel and the gate electrode and is in electrical contact with the channel and the gate electrode. Saturation current that flows through the channel increases when the metabolites react with the enzymes to produce electrons, which are directly transferred to the n-type polymers at the gate electrode and the channel. Methods of making and using the n-type electrochemical device are also disclosed.

19 Claims, 38 Drawing Sheets

(52) U.S. Cl.
CPC .............. *C12Q 1/002* (2013.01); *C12Q 1/005* (2013.01); *C12Q 1/006* (2013.01); *A61B 2562/125* (2013.01)

(56) References Cited

U.S. PATENT DOCUMENTS

| 2012/0143027 | A1 | 6/2012 | Phillips |
| 2016/0338626 | A1 | 11/2016 | Wang |
| 2019/0331673 | A1 | 10/2019 | Torsi |
| 2020/0033291 | A1 | 1/2020 | Tarasov |

FOREIGN PATENT DOCUMENTS

| WO | 2018048742 | 3/2018 |
| WO | 2021130525 | 7/2021 |

OTHER PUBLICATIONS

Pappa, Anna-Maria, et al. "Organic transistor arrays integrated with finger-powered microfluidics for multianalyte saliva testing." Advanced Healthcare Materials 5.17 (2016): 2295-2302. (Year: 2016).*
Pappa, Anna-Maria, et al. "Polyelectrolyte layer-by-layer assembly on organic electrochemical transistors." ACS Applied Materials & Interfaces 9.12 (2017): 10427-10434. (Year: 2017).*
Kros, et al., "Poly(3,4☐Lethylenedioxythiophene)☐Based Glucose Biosensors", Adv. Mater., 13:1555-1557 (2001).
Wustoni, et al., "Enzyme☐Free Detection of Glucose with a Hybrid Conductive Gel Electrode", Advanced Materials Interfaces, 6(1800928):1-10 (2019).
Al-Ani, et al., "Tuning the Density of Poly(ethylene glycol) Chains to Control Mammalian Cell and Bacterial Attachment", Polymers, 9:343 (2017).
Bambhania, et al., "Impact of Oxygen on Glucose Oxidation Kinetics in a Redox Polymer Mediated Glucose Oxidase Electrode", Journal of The Electrochemical Society, 164(4):H232-H240 (2017).
Bartlett, et al., "Enzyme switch responsive to glucose", Analytical Chemistry, 65(8):1118-1119 (1993).
Braendlein, et al., "Lactate detection in Tumor Cell Cultures Using Organic Transistor Circuits", Advanced Materials, 29(13):1605744 (2017).
Bruen, et al., "Glucose Sensing for Diabetes Monitoring: Recent Developments", Sensors, 17:1866 (2017).
Chen, et al., "Naphthalenedicarboximide- vs Perylenedicarboximide-Based Copolymers. Synthesis and Semiconducting Properties in Bottom-Gate N-Channel Organic Transistors", Journal of the American Chemical Society, 131(1):8-9 (2009).

Christwardana, et al., "Fabrication of Mediatorless/ Membraneless Glucose/ Oxygen Based Biofuel Cell using Biocatalysts Including Glucose Oxidase and Laccase Enzymes", Scientific Reports, 6(30128):1-10 (2016).
Du, et al., "Improving the Compatibility of Diketopyrrolopyrrole Semiconducting Polymers for Biological Interfacing by Lysine Attachment", Chemistry of Materials, 30(17):6164-6172 (2018).
Elmahmoudy, et al., "Tailoring the electrochemical and mechanical properties of PEDOT: pss films for bioelectronics", Macromol. Mater. Eng., 302(1600497):1-152 (2017).
Friere, et al., "Direct Electron Transfer: An Approach for Electrochemical Biosensors with Higher Selectivity and Sensitivity", J. Braz. Chem. Soc., 14:230-243 (2003).
Garjonyte, et al., "Investigation of electrochemical properties of FMN and FAD adsorbed on titanium electrode", Bioelectrochemistry, 61:39-49 (2003).
Gifford, et al., "Continuous Glucose Monitoring: 40 Years, What We've Learned and What's Next", ChemPhysChem. 14(10):2032-2044 (2013).
Giovannitti, et a., "Controlling the mode of operation of organic transistors through side-chain engineering", Proceedings of the National Academy of Sciences, 113(43):12017-12022 (2016a).
Giovannitti, et al., "Redox-Stability of Alkoxy-BDT Copolymers and their Use for Organic Bioelectronic Devices", Advanced Functional Materials, 28(17):1706325 (2018a).
Giovannitti, et al., "The Role of the Side Chain on the Performance of N-type Conjugated Polymers in Aqueous Electrolytes", Chemistry of Materials, 30(9):2945-2953 (2018b).
Giovannitti, et al., "N-type organic electrochemical transistors with stability in water", Nature Communications, 7:13066 (2016b).
Goodwin, et al., "Blood Lactate Measurements and Analysis during Exercise: A Guide for Clinicians", J. Diabetes Sci. Technol., 1(4):558-569 (2007).
Heller, et al., "Electrochemical Glucose Sensors and Their Applications in Diabetes Management", Chemical Reviews, 108(7):2482-2505 (2008).
Inal, et al., "Conjugated Polymers in Bioelectronics", Accounts of Chemical Research, 51(6):1368-1376 (2018a).
Inal, et al., "Visualizing the Solid-Liquid Interface of Conjugated Copolymer Films Using Fluorescent Liposomes", ACS Applied Bio Materials, 1(5):1348-1354 (2018b).
Inal, et al., "A High Transconductance Accumulation Mode Electrochemical Transistor", Advanced Materials, 26(44):7450-7455 (2014).
Inal, et al., "Organic electrochemical transistors based on PEDOT with different anionic polyelectrolyte dopants", Journal of Polymer Science Part B: Polymer Physics, 54(2):147-151 (2016).
Inal, et al., "Benchmarking organic mixed conductors for transistors", Nature Communications, 8(1):1767 (2017).
Jensen, et al., "Quantifying Protein Adsorption and Function at Nanostructured Materials: Enzymatic Activity of Glucose Oxidase at glad Structure Electrodes", Langmuir, 28(30):11106-11114 (2012).
Jiang, et al., "Enzyme-based Electrochemical Biosensors", Biosensors, 1:1-25 (2010).
Kang, et al., "Direct electrochemistry and bioelectrocatalysis of glucose oxidase in CS/CNC film and its application in glucose biosensing and biofuel cells", RSC Advances, 7(8):4572-4579 (2017).
Kergoat, et al., "Advances in organic transistor-based biosensors: from organic electrochemical transistors to electrolyte-gated organic field-effect transistors", Anal. Bioanal. Chem., 402:1813-1826 (2012).
Khodagholy, et al., "In vivo recordings of brain activity using organic transistors", Nature Communications, 4:1575 (2013a).
Khodagholy, et al., "High transconductance organic electrochemical transistors", Nature Communications, 4:2133 (2013b).
Khodagholy, et al., "NeuroGrid: recording action potentials from the surface of the brain", Nature Neuroscience, 18:310-315 (2014).
Kissinger, et al., "Engineering the Bioelectronic Interface: Applications to Analyte Biosensing and Protein Detection", Journal of the American Chemical Society, 132(4):1444-1444 (2010).
Kros, et al., "Poly (3, 4-ethylenedioxythiophene)-Based Glucose Biosensors", Adv. Mater., 13:1555-1557 (2001).

(56) References Cited

OTHER PUBLICATIONS

Liang, et al., "Heavily n-Dopable π-Conjugated Redox Polymers with Ultrafast Energy Storage Capability", *Journal of the American Chemical Society*, 137:4956-4959 (2015).
Liao, et al., "Flexible Organic Electronics in Biology: Materials and Devices", *Adv. Mater.*, 27:7493-7527 (2015).
Libansky, et al., "Basic electrochemical properties of sputtered gold film electrodes", *Electrochimica Acta*, 251:452-460 (2017).
Lineweaver, et al., "The Determination of Enzyme Dissociation Constants", *Journal of The American Chemical Society*, 56(3):658-666 (1934).
Mateo, et al., "Improvement of enzyme activity, stability and selectivity via immobilization techniques", *Enzyme and Microbial Technology*, 40(6):1451-1463 (2007).
Nielsen, et al., "Molecular Design of Semiconducting Polymers for High- Performance Organic Electrochemical Transistors", *Journal of the American Chemical Society*, 138(32):10252-10259 (2016).
Nien, et al., "Integrating an Enzyme-Entrapped Conducting Polymer Electrode and a Prereactor in a Microfluidic System for Sensing Glucose", *Electroanalysis*, 20:635-642 (2008).
Pappa, et al., "Direct metabolite detection with an n-type accumulation mode organic electrochemical transistor", *Science*, 4(6):eaat0911 (2018).
Pappa, et al., "Organic Transistor Arrays Integrated with Finger-Powered Microfluidics for Multianalyte Saliva testing", *Advance Healthcare Materials*, 5(17):2295-2302 (2016).
Pappa, et al., "Polyelectrolyte Layer-by-Layer Assembly on Organic Electrochemical Transistors", *ACS Appl. Mater. Interfaces*, 9:10427-10434 (2017a).
Pappa, et al., "Organic Electronics for Point-of-Care Metabolite Monitoring", *Trends in Biotechnology*, 36(1):45-59 (2017b).
Pas, et al., "Neurospheres on Patterned PEDOT: PSS Microelectrode Arrays Enhance Electrophysiology Recordings", *Advanced Biosystems*, 2(1):1700164 (2018).
Rathee, et al., "Biosensors based on electrochemical lactate detection: A comprehensive review", *Biochem. Biophys. Rep.*, 5:35-54 (2016).
Rivnay, et al., "Organic Electrochemical Transistors with Maximum Transconductance at Zero Gate Bias", *Advanced Materials*, 25(48):7010-7014 (2013).
Rivnay, et al., "Organic electrochemical transistors", *Nature Reviews Materials*, 3:17086 (2018).
Rivnay, et al., "High-performance transistors for bioelectronics through tuning of channel thickness", *Sci. Adv.*, 1:e1400251 (2015).
Rocchitta, et al., "Enzyme Biosensors for Biomedical Applications: Strategies for Safeguarding Analytical Performances in Biological Fluids", *Sensors*, 16(780)1-21 (2016).
Saboe, et al., "Biomimetic and bioinspired approaches for wiring enzymes to electrode interfaces", *Energy & Environmental Science*, 10:14-42 (2017).
Sakharov, et al., "Relationship between Lactate Concentrations in Active Muscle Sweat and Whole Blood", *Bulletin of Experimental Biology and Medicine*, 150(1):83-85 (2010).
Savva, et al., "Ionic-to-electronic coupling efficiency in PEDOT: PSS films operated in aqueous electrolytes", *Journal of Materials Chemistry C*, 6:12023-12030 (2018).
Schuhmann, et al., "Electron-transfer pathways in amperometric biosensors. Ferrocene-modified enzymes entrapped in conducting-polymer layers", *Biosensors and Bioelectronics*, 10:181-193 (1995).
Sekretaryova, et al., "Bioelectrocatalytic systems for health applications", *Biotechnol. Adv.*, 34:177-197 (2016).
Sessolo, et al., "Easy-to-Fabricate Conducting Polymer Microelectrode Arrays", *Advanced Materials*, 25(15):2135-2139 (2013).
Sheldon, et al., "Enzyme Immobilization: The Quest for Optimum Performance", *Advanced Synthesis & Catalysis*, 349(8-9):1289-1307 (2007).
Simon, et al., "Organic Bioelectronics: Bridging the Signaling Gap between Biology and Technology", *Chemical Reviews*, 116:13009-13041 (2016).
Strakosas, et al., "The organic electrochemical transistor for biological applications", *Journal of Applied Polymer Science*, 132(15):41735 (2015).
Sun, et al., "Complementary Logic Circuits Based on High-Performance n-Type Organic Electrochemical Transistors", *Advanced Materials*, 30(9):1704916 (2018).
Suzuki, et al., "Flavin mononucleotide mediated electron pathway for microbial U (VI) reduction", *Phys. Chem. Chem. Phys.*, 12:10081-10087 (2010).
Tekus, et al., "Comparison of Blood and Saliva Lactate Level After Maximum Intensity Exercise", *Acta Biol. Hung.*, 63(Suppl. 1):89-98 (2012).
Thompson, et al., "Conducting Polymer Enzyme Alloys: Electromaterials Exhibiting Direct Electron Transfer", *Macromolecular Rapid Communications*, 3(14):1293-1297 (2010).
Trefz, et al., "Electrochemical Investigations of the N-Type Semiconducting Polymer P(NDI2OD-T2) and Its Monomer: New Insights in the Reduction Behavior", *J. Phys. Chem. C.*, 40:22760-22771 (2015).
Turner, et al., "Biosensors: sense and sensibility", *Chem. Soc. Rev.*, 42:3184-3196 (2013).
Witkowska, et al., "Electrochemical Glucose Sensing: Is There Still Room for Improvement", *Analytical Chemistry*, 88(23):11271-11282 (2016).
Wu, et al., "Biosensors based on direct electron transfer in redox proteins", *Microchimica Acta*, 159(1):1-17 (2007).
Wustoni, et al., "Enzyme-Free Detection of Glucose with a Hybrid Conductive Gel Electrode", *Advanced Materials Interfaces*, doi.org. 10.1002/admi.201800928 (2018).
Yang, et al., "The effect of Crosslinked networks with poly (ethylene glycol) on sulfonated polyimide for polymer electrolyte membrane fuel cell", *Journal of Polymer Science B Polymer Physics*, 43:1455-1464 (2005).
Yates, et al., "Methodologies for "Wiring" Redox Proteins/Enzymes to Electrode Surfaces", *Chemistry: A European Journal*, 24(47):12164-12182 (2018).
Zhang, et al., "Third-Generation Biosensors Based on the Direct Electron Transfer of Proteins", *Analytical Sciences*, 20(4):603-609 (2004).
Zhang, et al., "Covalent attachment of glucose oxidase to an Au electrode modified with gold nanoparticles for use as glucose biosensor", *Biochemistry*, 67(1):15-22 (2005a).
Zhang, et al., "Highly selective and sensitive sensor based on an organic electrochemical transistor for the detection of ascorbic acid", *Biosens. Bioelectron.*, 100:235-241 (2018a).
Zhang, et al., "Lipid Bilayer Formation on Organic Electronic Materials", *Journal of Materials Chemistry C*, 6(19):5218-5227 (2018b).
Zhang, et al., "Immobilization of glucose oxidase on gold nanoparticles modified Au electrode for the construction of biosensor", *Sensors and Actuators B: Chemical*, 109(2):367-374 (2005b).
Zhao, et al., "Mediatorless glucose biosensor and direct electron transfer type glucose/air biofuel cell enabled with carbon nanodots", *Analytical Chemistry*, 87(5):2615-2622 (2015).
Zhu, et al., "Electrochemical Sensors and Biosensors Based on Nanomaterials and Nanostructures", *Analytical Chemistry*, 87(1):230-249 (2015).
International Search Report for corresponding PCT application PCT/IB2019/050443 dated May 9, 2019.
Bihar, et al. "Fully Printed Electrodes on Stretchable Textiles for Long_Term Electrophysiology", Adv. Mater. Technol., 2(4):1600251 (2017).
Bihar, et al., "A fully inkjet-printed disposable glucose sensor on paper", npj Flexible Electronics, 2(30):1-8 (2018).
Fahlman Mats et al, "Interfaces in organic electronics", Nature Reviews Materials, 4(10): 627-650 (2019).
Gerard, et al., "Application of conducting polymers to biosensors", Biosens. Bioelectron., 17(5):345-359 (2002).
Guo, et al., "Rapid single-molecule detection of COVID-19 and MERS antigens via nanobody-functionalized organic electrochemical transistors", Nature Biomedical Engineering, 5, (7):666-67 (2021).

(56) References Cited

OTHER PUBLICATIONS

Jia, et al., "Electrochemical Tattoo Biosensors for Real-Time Non-invasive Lactate Monitoring in Human Perspiration", Anal. Chem., 85(14):6553-6560 (2013).

Li, et al., "All Inkjet-Printed Amperometric Multiplexed Biosensors Based on Nanostructured Conductive Hydrogel Electrodes", Nano Lett., 18(6): 3322-3327 (2018). doi: 10.1021/acs.nanolett.8b00003.

Maattanen, et al., "A low-cost paper-based inkjet-printed platforn1 for electrochen1ical analyses", Sensors and Actuators B, 177:153-162 (2013).

Macchia, et al., "Organic electrochemical transistor immuno-sensor operating at the femto-molar limit of detection", 2017 7th IEEE International Workshop on Advances in Sensors and Interfaces (IWASI), IEEE, p. 68-72 (2017).

Oh, et al., "Recent advances in chemical functionalization of nanoparticles with biomolecules for analytical applications", Analytical and Bioanalytical Chemistry, 407(29):8627-8645 (2015).

Pu, et al., "Cylindrical Electrochemical Sensor Fabricated by Rotated Inkjet Printing on Flexible Substrate for Glucose Monitoring", 2017 19th International Conference on Solid-State Sensors, Actuators and Microsystems (Transducers), 1241-1244 (2017).

Scheiblin, et al., "Screen-printed organic electrochemical transistors for metabolite sensing", MRS Commun., 5(3):507-511 (2015).

Soni, et al., "A paper strip based non-invasive glucose biosensor for salivary analysis", Biosens. Bioelectron., 67:763-768 (2015).

Torricelli , "Enhanced multifunctional bioelectronics with integrated organic electrochemical transistor architectures", Progress in Biomedical Optics and Imaging, SPIE—International Society for Optical Engineering, vol. 11663, Mar. 5, 2021 (Mar. 5, 2021), p. 116630P-116630P.

Tortorich, et al., "Inkjet-Printed and Paper-Based Electrochemical Sensors", Applied Science, 8(288):1-16 (2018).

Xia, et al., "Conducting polymer nanostructures and their application in biosensors", J. Colloid Interface Sci., 341(1):1-11 (2010).

International Search Report received for PCT Patent Application No. PCT/IB2019/053496, mailed on Aug. 13, 2019, 4 pages.

Bihar, Eloïse , "Inkjet printed organic electronic devices for biomedical diagnosis", These de doctorat, Universite de Lyon, 2016, pp. 1-132.

* cited by examiner $$LOx\ (FMN) + 2e^- + 2H^+ \rightarrow LOx\ (FMNH_2) \quad (1)$$
$$LOx\ (FMNH_2) \rightarrow LOx\ (FMN) + 2e^- + 2H^+ \quad (2)$$
$$LOx\ (FMNH_2) + O_2 \rightarrow LOx\ (FMN) + H_2O_2 \quad (3)$$
$$LOx\ (FMN) + lactate \rightarrow LOx\ (FMNH_2) + Pyruvate \quad (4)$$

N-TYPE POLYMER BASED ELECTROCHEMICAL DEVICE FOR DIRECT ENZYMATIC METABOLITE SENSING AND METHODS OF MAKING AND USING

CROSS-REFERENCED TO RELATED APPLICATION

This application is a National Phase application under 35 U.S.C. § 371 of International Application No. PCT/IB2019/050443, filed on Jan. 18, 2019, which claims the benefit of and priority to U.S. Provisional Application No. 62/618,794 filed Jan. 18, 2018, which are hereby incorporated herein by reference in their entirety.

FIELD OF THE INVENTION

The invention is generally directed to n-type polymer based electrochemical device for metabolite sensing. Specifically, the present invention is directed to n-type polymer based accumulation mode organic electrochemical transistors for direct metabolites sensing.

BACKGROUND OF THE INVENTION

Enzyme-based electrocatalysis has gained significant interest for the development of biosensors (Sekretaryova, et al., *Biotechnol. Adv.*, 34:177-197 (2016)). Biosensors occupy a significant market in healthcare industry with a yearly US $13 billion annual turnover (Pappa, et al., *Trends in Biotechnology*, 36(1):45-59 (2017)). The inherent substrate specificity and catalytic activity of enzymes (oxidoreductases) coupled with their ability to undergo electronic communication with the sensing electrode have stimulated their widespread application in amperometric biosensors, predominantly for the detection of physiologically relevant metabolites such as glucose (Jiang and Zhao, *Enzyme-based Electrochemical Biosensors, in Biosensors*, P. A. Serra, Ed.: InTech (2010)).

The flagship figure of the modern biosensors is without a doubt glucose sensors, representing 85% of the total biosensor market (Gifford, et al., *ChemPhysChem*, 14(10):2032-2044 (2013); Witkowska, et al., *Analytical Chemistry*, 88(23):11271-11282 (2016)). This is due to the crucial role of glucose in cellular machinery: glucose is the primary source of energy used for performing various cell functions such as conduction of neurons and active transport as well as synthesis of biochemical substances. Monitoring glucose levels in bodily fluids is therefore crucial for early diagnosis of a variety of diseases, in particular of diabetes, a pandemic disorder related to abnormal levels of glucose build up in the bloodstream (Wang, et al., *Chemical Reviews*, 108(2):814-825 (2008); Heller, et al., *Chemical Reviews*, 108(7):2482-2505 (2008)). Today, the majority of glucose sensors are based on the enzyme, glucose oxidase, due to its high selectivity and excellent catalytic activity towards glucose (Mulchandani and Rogers, *Principles of Enzyme Biosensors, in Enzyme and Microbial Biosensors: Techniques and Protocols*, Humana Press, Ed.: Totowa, NJ (1998)). Glucose oxidase transforms glucose via an electrochemical reaction through an electron transfer process while it is electrochemically regenerated by ambient oxygen, generating hydrogen peroxide ($H_2O_2$). First generation of glucose biosensors detect this byproduct, $H_2O_2$, and correlate it to the amount of glucose. In order to improve selectivity, recent sensors have been designed such that they either involve an electron transfer mediator which replaces the co-substrate oxygen (therefore inhibits the $H_2O_2$ production) or an electronic transducer which can electronically wire the enzyme to its surface (direct detection of glucose) (Freire, et al., *Journal of the Brazilian Chemical Society*, 14:230-243 (2003); Wu, et al., *Microchimica Acta*, 159(1):1-17 (2007); Zhang, et al., *Analytical Sciences*, 20(4):603-609 (2004); Zhu, et al., *Analytical Chemistry*, 87(1):230-249 (2015)).

An obvious prerequisite when it comes to engineering such bioelectrochemical devices is the electron transfer (ET) between the sensing electrode and the redox active sites of the enzyme. For most of the enzymes, efficient electrical communication with the electrode is largely restricted by the distance between the active sites (and/or the electron transport pathways within the enzyme) and the electrode surface (Turner, *Chem. Soc. Rev.*, 42:3184-3196 (2013); Freire, et al., *Journal of the Brazilian Chemical Society*, 14:230-243 (2003)). This is more of an issue for flat, unstructured surfaces of traditional electrode materials, limiting intermolecular interactions. To mediate ET, a typical strategy has, therefore, been the inclusion of redox active molecules acting as electron relays in the sensor architecture—in a freely diffusing form or coupled to the electrode (Pappa, et al., *Trends in Biotechnology*, 36(1):45-59 (2017)).

A promising transducing element for sensitive and selective glucose sensing is organic mixed conductors (OMCs) (Inal, et al., *Accounts of Chemical Research*, 51(6):1368-1376 (2018)). OMCs are often conjugated polymers that support electronic charge transport along their backbones, while allowing for ionic transport through their bulk, with great potential to act as electron relays (Inal, et al., *Nature Communications*, 8:1767 (2017)). Alongside their inherent ability to undergo reversible electrochemical reactions (changes in their doping state upon ion exchange with an electrolye), their fuzzy/soft surfaces can aid in promoting interactions with proteins, thus inducing electronic communication with the catalytic sites of the enzymes (Pappa, et al., *Trends in Biotechnology*, 36(1):45-59 (2017); Thompson, et al., *Macromol. Rapid Commun.*, 31:1293-1297 (2010); Kros, et al., *Adv. Mater.*, 13:1555-1557 (2001); Simon, et al., *Chemical Reviews*, 116:13009-13041 (2016); Bartlett, et al., *Analytical Chemistry*, 65:1118-1119 (1993); Nien, et al., *Electroanalysis*, 20:635-642 (2008); Schuhmann, et al., *Biosensors and Bioelectronics*, 10:181-193 (1995)). In addition, the chemistry of conjugated polymers is tunable allowing for customized materials for biochemical sensing.

OMCs enable different modes of device operations such as electrochemical sensors and passive large-scale electrodes, aiming to include conjugated conducting polymers as bio-electronic transducers (Kissinger, et al., *Journal of the American Chemical Society*, 132(4):1444-1444 (2010)). However, biological signals often need to be amplified and such sensors render miniaturization challenging, limiting the applicability of the materials in different environments such as in vivo. An enticing solution is the organic electrochemical transistor (OECT), an electrolyte gated transistor which utilizes conjugated polymers in the channel (Rivnay, et al., *Nature Reviews Materials*, 3:17086 (2018); Strakosas, et al., *Journal of Applied Polymer Science*, 132(15):41735 (2015)). In OECTs, a bias at the gate electrode injects ions from an aqueous electrolyte into the bulk of the material, resulting in a change in the conductivity of the channel. The device acts as a switch and an amplifier. The OECT can transduce ionic signals of biological origin into electronic ones, with particularly high amplification (Kergoat, et al., *Anal. Bioanal. Chem.*, 402:1813-1826 (2012); Rivnay, et al., *Nature Reviews Materials*, 3:17086 (2018); Giovannitti, et al., *Proc. Natl. Acad. Sci. U.S.A.*, 113:12017-12022 (2016)).

The volumetric interactions of the electrolyte (dopant/dedopant) ions with the bulk of the OMC channel, leading to remarkable sensitivity for biotransduction (Rivnay, et al., *Sci. Adv.*, 1:e1400251 (2015); Zhang, et al., *Biosens. Bioelectron.*, 100:235-241 (2018); Liao, et al., *Adv. Mater.*, 27:7493-7527 (2015)).

For glucose detection with OECTs, the strategy has been the functionalization of the gate electrode (made of inert metals or the conducting polymer poly(3,4-ethylenedioxythiophene) doped with polystyrene sulfonate, PEDOT:PSS) with glucose oxidase/mediator and amplifying the glucose detection at the gate electrode by the PEDOT:PSS channel (Inal, et al., *Nature Communications*, 8(1):1767 (2017); Inal, et al., *Advanced Materials*, 26(44):7450-7455 (2014); Khodagholy, et al., *Nature Communications*, 4:2133 (2013); Rivnay, et al., *Science Advances*, 1(4):e1400251 (2015); Rivnay, et al., *Advanced Materials*, 25(48):7010-7014 (2013)). Moreover, side-chain engineering of the polymer structure has been successfully implemented to enhance biocompatibility, stability, and device performance (Du, et al., *Chemistry of Materials*, 30(17):6164-6172 (2018); Giovannitti, et al., *Nature Communications*, 7:13066 (2016); Giovannitti, et al., *Advanced Functional Materials*, 28(17):1706325 (2018); Giovannitti, et al., *Chemistry of Materials*, 30(9):2945-2953 (2018); Giovannitti, et al., *Proceedings of the National Academy of Sciences*, 113(43):12017-12022 (2016); Nielsen, et al., *Journal of the American Chemical Society*, 138(32):10252-10259 (2016)). To date, the gold standard of biosensing with OECT lies on the p-type semiconductor poly(3,4-ethylenedioxythiophene) doped with polystyrene sulfonate (PEDOT:PSS) as active material. Due to their outstanding properties (i.e conductivity, stability, response time), PEDOT:PSS and its derivatives, have been employed in numerous applications including metabolite sensing (Braendlein, et at, *Advanced Materials*, 29(13):1605744 (2017); Pappa, et al., *Advanced Healthcare Materials*, 5(17):2295-2302 (2016); Wustoni, et al., *Advanced Materials Interfaces*, doi.org/10.1002/admi.201800928 (2018)), evaluating lipid bilayer formation (Zhang, et al., *Advanced Functional Materials*, 26(40):7304-7313 (2016); Zhang, et al., *Journal of Materials Chemistry C*, 6(19):5218-5227 (2018)) and neural recordings, both in vitro (Pas, et al., *Advanced Biosystems*, 2(1):1700164 (2018)) and in vivo (Khodagholy, et al., *Nature Communications*, 4:1575 (2013); Khodagholy, et al., *Nature Neuroscience*, 18:310 (2014)).

In the aforementioned OECTs, however, as in most electrochemical biosensors to date, direct ET has been rather sluggish, limiting their selectivity and speed. This can be overcome by the integration of ET mediators, albeit at the expense of complicating the sensor fabrication. Moreover, despite the high signal amplification provided by the OECT, PEDOT:PSS-based devices display the inherent disadvantage in that they operate in depletion mode (Rivnay, et al., *Nature Reviews Materials*, 3:17086 (2018)). In this mode, electrochemical dedoping of the p-type channel (that is, a decrease in its conductance) as a result of the applied gate potential or a biological event (such as the enzyme-based electrocatalysis) will switch the transistor off, wherein many factors other than the electrochemical reactions of interest could lead to a decrease in channel current (e.g. degradation over time and non-specific interactions with electrolyte components).

For biosensing, it is more advantageous to have an accumulation mode device (Inal, et al., *Advanced Materials*, 26:7450-7455 (2014)), which switches on upon the biorecognition event as in depletion mode sensors; a reduction in current over time, possibly due to degradation of the polymer, might intervene with the actual sensor output. Moreover, the depletion OECT being always on increases power consumption. While the inherent specificity and electrochemical reversibility of enzymes poise them as the biorecognition element of choice for a wide range of metabolites, challenges associated with their facile integration and efficient communication with electrodes remain With the notable exception of today's market praised success story in glucose biosensors, enzyme-based devices, including OECTs, are still limited in their adaptation into different geometries and form factors and for applications beyond in vitro platforms.

There remains a need for conjugated polymers based accumulation mode electrochemical devices for metabolite sensing that are greatly simplified and with improved performance such as high sensitivity, wide dynamic range, tunable sensitivity according to the analyte range of choice (blood, saliva, sweat, and tears), good selectivity, and improved operational stability and shelf life.

It is therefore an object of the present invention to provide simple n-type polymers based accumulation mode electrochemical devices with improved performance.

It is another object of the present invention to provide methods of making the simple n-type polymers based accumulation mode electrochemical devices with improved performance.

It is yet another object of the present invention to provide methods of using the simple n-type polymers based accumulation mode electrochemical devices with improved performance.

SUMMARY OF THE INVENTION

Simple n-type polymer based accumulation mode electrochemical devices for metabolite sensing with improved performance, methods of making and using thereof, are provided.

The n-type polymer based electrochemical devices include one or more source electrodes, one or more drain electrodes, one or more channels, a gate electrode, and an electrolyte solution. The channels include the following: (a) one or more n-type polymers and (b) one or more enzymes. The gate electrode includes the following: (a) one or more n-type polymers and (b) one or more enzymes. The source electrode and the drain electrode are electrically connected by the corresponding channel. The electrolyte solution contains one or more metabolites capable of reacting with the one or more enzymes at the channel and the gate electrode. In one preferred embodiment, the enzyme is GOx and the metabolite is glucose. In another preferred embodiment, the enzyme is LOx and the metabolite is lactate. The electrolyte solution is in electrical contact with the channels and the gate electrode. In some embodiments, the electrochemical device contains a plurality of independently addressable source and drain electrodes, a common gate electrode, and corresponding channels, wherein the corresponding channels contain different enzymes.

A gate voltage ($V_G$) is applied to the electrochemical device and a source-drain current ($I_D$) is monitored. The $I_D$ increases when the metabolites react with the enzymes to produce electrons; the electrons are directly transferred to the n-type polymers at the gate electrode and the channel, increasing the conductivity of the polymers.

The structure of the n-type polymer facilitates interactions of the enzyme with the polymer, and allows good electrical contact between the enzyme and the polymer. This way, the electrons generated from the enzymatic reaction are transferred directly from the redox center to the polymer backbone. In some preferred embodiments the n-type polymer is naphthalene-1,4,5,8-tetracarboxylic-diimide-bithiophene (NDI-T2) polymer with 90% glycol chain percentage (P90).

The electrochemical device acts as both the amplifier and the signal transducer together with the properties of the n-type polymers lead to greatly improved sensing performance.

Also provided are methods of making n-type polymer based electrochemical devices, which includes one or more source electrodes, one or more drain electrodes, one or more channels, a gate electrode, and an electrolyte solution. The channel includes the following: (a) one or more n-type polymers and (b) one or more enzymes. The gate electrode includes the following: (a) one or more n-type polymers and (b) one or more enzymes. The electrochemical device is made by: (1) placing a source electrode and a drain electrode apart from each other; (2) electrically connecting the source and the drain electrodes with a channel containing one or more polymers; (3) placing a gate electrode apart from the source, the drain, and the channel; (4) contacting the gate electrode with one or more n-type polymer; (5) contacting the channel and the gate electrode with one or more enzymes; (6) contacting the channel and the gate electrode with an electrolyte solution contain one or more metabolites/substrate reactive with the one or more enzymes. In some embodiments, the electrochemical device contains a plurality of independently addressable source and drain electrodes, a common gate electrode, and corresponding channels, wherein the corresponding channels contain different enzymes. In a preferred embodiment, the dimension of the electrochemical device is between 1000 and 1000000 $\mu m^2$. In some embodiments, the dimension of the channel is 1000 $\mu m^2$ and the gate electrode is 250000 $\mu m^2$. In one embodiment, the channel and gate each has a dimension of 100 $\mu m^2$.

The n-type polymer based electrochemical devices disclosed herein can be utilized as an in vivo sensing device for measuring metabolites such as glucose and/or lactate from the blood stream. Such in vivo electrochemical sensing devices may be utilized as an implanted device for continuously monitoring a single metabolite or multiple metabolites simultaneously, wherein the metabolites are derived from the organism. In another embodiment, the electrochemical device can be utilized in vitro as portable devices and/or wearable electronics that measure a single metabolite or multiple metabolites that react with the enzymes, including, but are not limited to, glucose and lactate.

BRIEF DESCRIPTION OF THE DRAWINGS

FIG. 4A shows graphs of gate current over the successive additions of the different analytes tested. FIG. 4B shows graphs of normalized drain current (vs response to 1 mM Glucose) in presence of the enzyme GOx (top) or not (bottom) under different biasing conditions. The error is calculated from 3 measurements of 3 different devices.

FIG. 12A is in linear scale. FIG. 12B shows the magnified linear part of the cure from 10 $\mu M$ to 1 mM. The linear interpolation of the calibration curve, with an adjusted R-squared value of ~0.96, indicates a linear regression up to 1 mM of lactate. The slope, calculated to be ~0.214 expresses the sensitivity of the device per mM of lactate concentration. NR is calculated according to equation (1). FIG. 12C is in logarithmic scale. Error bars represent the standard deviation from the mean value (n=4).

FIG. 13B shows the raw QCM-D data of frequency change versus time in which the Left axis shows the change in frequency and the right one of the dissipation for the overtones $5^{th}$ and $7^{th}$. The film is first in air, then exposed to PBS which is followed by the introduction of Lox in PBS and is finally rinsed with PBS. The mass change is calculated treating this data with viscoelastic model. The inset is a magnification of the change in frequency ($5^{th}$ overtone) as the enzyme is injected into the PBS solution flowing over the film.

FIG. 16A shows the change in pH of the solution containing Lox as a function of lactate concentration. FIG. 16B shows CV curves of P90 film recorded in solutions of different Ph.

FIG. 17A shows the changes in the UV-vis-NIR spectrum of the P90 film, cast on an indium tin oxide (ITO) substrate, in PBS solution containing the enzyme (black curve) and upon addition of 10 mM lactate (red curve). The curves are normalized to the absorbance value at 1000 nm where no changes occur during electrochemical switching. a.u., arbitrary units. FIG. 17B shows the changes in the absorbance spectrum of the P90 film coated on an ITO substrate measured in PBS during the electrochemical switch (with and without applied bias of −0.5 V vs. Ag/AgCl).

FIG. 26A shows a scheme of interdigitated gold electrodes coated with lysine functionalized DPP polymers and the measurement solution (standard 0.1 M NaCl solution). FIG. 26B shows CV curves of the lysine functionalized DPP polymers. FIG. 26C shows the conductance of the lysine functionalized DPP polymers. The inset shows the full scale of conductance curves. FIG. 26D shows the electrochemical impedance spectra (impedance magnitude vs. frequency) of the lysine functionalized DPP polymers at open circuit potential (V=Voc, solid line) as well as at an oxidation potential (V=0.26 V vs. Voc, square symbols). All measurements are recorded in 0.1 M aqueous NaCl solution.

DETAILED DESCRIPTION OF THE INVENTION

I. Definitions

Figure 1A:
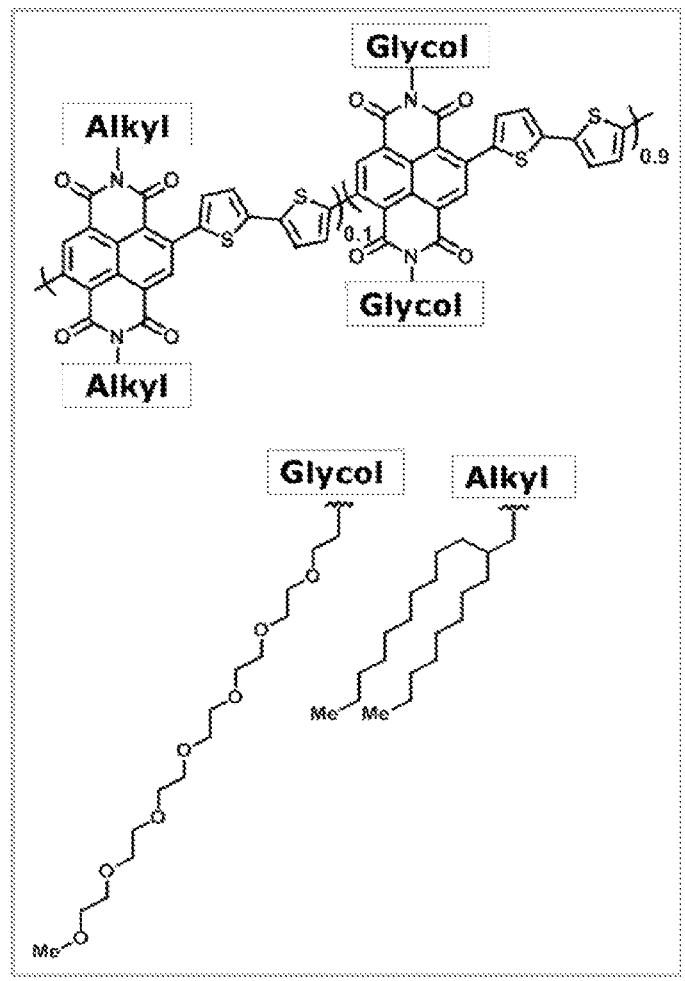
FIGS. 1A and 1B show the chemical structure of the n-type copolymer P90 (FIG. 1A) and a schematic illustration of the n-type accumulation mode organic electrochemical transistor (gate dimensions: 500 $\mu m^2$, channel dimensions: 10 $\mu m \times 100$ $\mu m$). The oxidation of glucose by the adsorbed GOx transfers electron to the polymer and further dopes it (FIG. 1B).

As used herein, the term "alkylene glycol" or "glycol" refers to ethylene oxide, propylene oxide, or copolymers of ethylene oxide or propylene oxide. The terms "alkylene glycol" or "glycol" are used interchangeably throughout the instant disclosure.

As used herein, the term "channel" refers to the electrical connection established between the source and the drain electrodes by the n-type polymer.

As used herein, the term "direct electron transfer" means the process of transferring electrons directly from an enzyme or a compound to an electron acceptor such as a polymer or an electrode, or from an electron donor to a compound or an enzyme.

As used herein, the term "drain" or "drain electrode" refers to an electrode which accepts charge carriers from a channel. The terms "drain" and "drain electrode" are used interchangeably throughout the instant disclosure.

As used herein, a "electrochemical device", "n-type electrochemical device", "n-type polymer based electrochemical device" or "n-type polymers based accumulation mode electrochemical device" includes one or more source electrodes, one or more drain electrodes, one or more channels, a gate electrode, and an electrolyte solution containing one or more metabolites. The source electrode and the drain electrode are placed apart and connected electronically by the channel. The channel contains one or more enzymes and one or more n-type polymers. The gate electrode contains one or more n-type polymers and one or more enzymes. The gate electrode is placed separately from the source electrode, the drain electrode, and the channel to prevent electron flow between the gate electrode and the channel. The electrolyte solution is in electrical contact with the gate electrode and the channel. The electrochemical device may contain a plurality of independently addressable source and drain electrodes, a common gate electrode, and corresponding channels, wherein the corresponding channels contain different enzymes. The terms "electrochemical device", "n-type electrochemical device", "n-type polymer based electrochemical device" and "n-type polymers based accumulation mode electrochemical device" are used interchangeably throughout the instant disclosure. The electrochemical device disclosed herein may be used for in vitro and in vivo applications.

As used herein, the term "electrolyte solution" refers to a solution that contains ions, atoms, or molecules that have lost or gained electrons, and is electrically conductive. The electrolyte solution is in electrical communication with the bioanode and the biocathode. The electrolyte solutions contains one or more metabolites.

As used herein, the term "electron mediator" refers to a compound that can accept or donate electrons. Electron mediators can facilitate electron transfer generated from an enzymatic reaction between enzymes and metabolites to electrodes.

As used herein, the term "enzyme" refers to a protein that functions as a catalyst in a chemical reaction. Enzymes include, but are not limited to glucose oxidase, glucose dehydrogenase, alcohol dehydrogenase, aldehyde dehydrogenase, formate dehydrogenase, formaldehyde dehydrogenase, lactic dehydrogenase, lactose dehydrogenase, lactate oxidase, cholesterol oxidase, tyrosinase, and pyruvate dehydrogenase. Preferred enzymes include oxidase which catalyzes the oxidation of a metabolite, such as glucose oxidase (GOx). Enzymes useful for biocathodes include oxygen reductase, such as laccase and bilirubin oxidase.

As used herein, the term "gate voltage" or "$V_G$" refers to the gate to source voltage.

As used herein, the term "improved performance" or "improved sensing performance" in connection with n-polymer based electrochemical devices disclosed include high sensitivity and selectivity, wide dynamic range, tunable sensitivity, insensitivity to oxygen and pH, and/or improved stability.

As used herein, the term "metabolite" means any compound that has stored energy. Preferred metabolites are carbon-based compound that has stored energy. Metabolites include but are not limited to nucleic acids, carbohydrates, alcohols, fatty acids and other hydrocarbons, ketones, aldehydes, amino acids, and proteins. The "metabolite" may be a biological compound within an organism. Preferred metabolites are carbohydrates, which include glucose, glucose-2, D-glucose, L-glucose, and glucose-6-phosphate.

As used herein, the term "n-type polymer" or "n-type conjugaed polymer" refers to a polymer capable of accepting electrons and stabilizing electrons on its backbone. A preferred "n-type semiconducting polymer", P90, is based on an NDI-T2 copolymer, which has a backbone comprising a highly electron-deficient naphthalene-1,4,5,8-tetracarboxylic diimide (NDI) repeat unit and an electron-rich unsubstituted bithiophene repeat unit (T2). (Giovannitti, et al., *Chemistry of Materials*, 30:2945-2953 (2018); Pappa, et al., *Science Advances*, 4:eaat0911 (2018)). The terms "n-type polymer" and "n-type conjugated polymer" are used interchangeably throughout the instant disclosure. The term "p-type polymer" refers to a polymer capable of donating electrons. The terms "n-type polymer" and "n-type conjugated polymer" are used interchangeably throughout the instant disclosure.

As used herein, the term "planar configuration" refers to the arrangement of the components of a electrochemical device is on a common plane.

As used herein, the term "physiological relevant concentration" refers to the concentration of the external or internal milieu that may occur in nature for that organism or cell system (Bruen, et al., *Sensors*, 17:1866 (2017)).

As used herein, the term "polar group" refers to a group in which the bond dipoles present do not cancel each other out and thus results in a molecular dipole.

As used herein, the term "sensor" refers to a device that detects or measures an event or a change of a physical property of an analyte, and records, indicates, or responds to the event or change. In one embodiment, the sensor can measure or sense metabolites, ions, pH, or temperature. In some embodiments, the sensor can measure or sense one or more analytes.

As used herein, the term "source" or "source electrode" refers to an electrode which provides charge carriers to a channel. The terms "source" and "source electrode" are used interchangeably throughout the instant disclosure.

As used herein, the term "source-drain current" or "$I_D$" refers to the saturation current that flows through the channel.

As used herein, the term "stability" or "shelf life" refers to the electrochemical device's capability to preserve its detection sensitivity with no noticeable effect of degradation. "Improved stability" is used to refer to the fuel cell's capability to preserve its detection sensitivity with no noticeable effect of degradation for 6 months.

As used herein, the term "threshold potential" refers to the minimum gate voltage required to result in a $I_D$ in the absence of an enzymatic reaction.

II. N-Type Polymer Based Electrochemical Device

The Examples below demonstrate for the first time the use of n-type conjugated polymers in an accumulation mode electrochemical device for the direct detection of metabolites. The detection is based on direct electron transfer between the enzyme and the polymers. The n-type polymer based electrochemical device is greatly simplified, obviating the need for synthetic or post-synthetic biofunctionalization that involves complex chemistry, mediators, and a reference electrode. The use of a lateral micrometer-scale gate electrode based on the n-type polymer and elimination of an external reference electrode allow for straightforward adaptation of this device type into different geometries and forms for both in vitro and in vivo applications. The device also exhibits improved performance such as high sensitivity, wide dynamic range, tunable sensitivity according to the analyte range of choice (blood, saliva, sweat, and tears), excellent selectivity, and improved operational stability and a shelf life of 6 months. The role of the electrochemical device as both the amplifier and transducer and the design simplicity endowed by the inherent surface and bulk properties of the n-type material poise the resulting platform as a prominent alternative to the conventional amperometric enzyme electrodes. Another feature of the n-type polymer based electrochemical device is that it is selective toward the specific metabolites of interest without being affected by oxygen or change of pH.

Figure 8A:
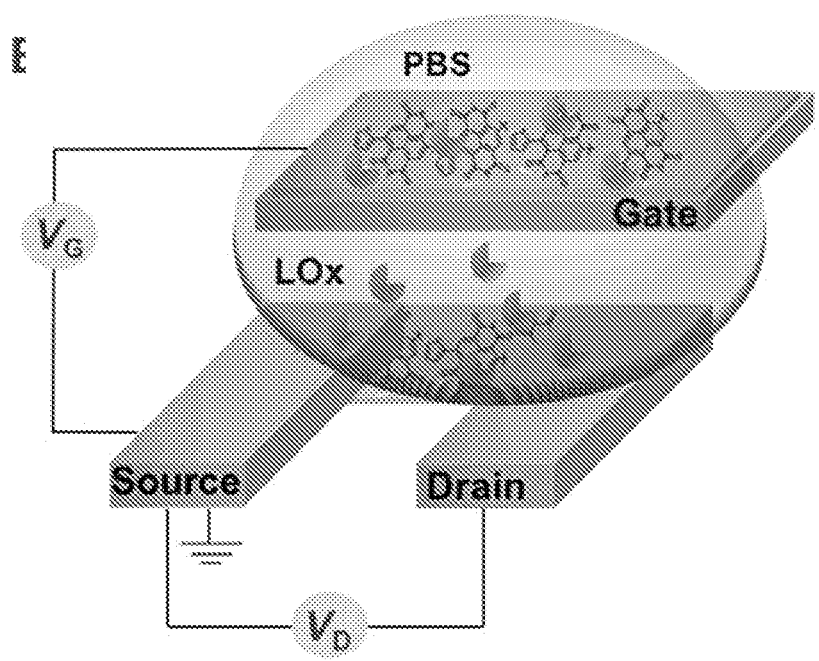
FIGS. 8A and 8B show a schematic of the OECT [gate dimensions, 500 mm2; channel dimensions, 10 mm (length)×100 mm (width)×~100 nm (thickness)] (FIG. 8A) and a schematic of the OECT biosensor showing the presumed interactions between the enzyme, LOx, and the n-type channel (note also that the gate electrode is exposed to Lox and lactate) (FIG. 8B).

N-type polymer based electrochemical device include one or more source electrodes, one or more drain electrodes, one or more channels, a gate electrode, and an electrolyte solution containing one or more metabolites. The dimension of the electrochemical device is between 1000 and 1000000 $\mu m^2$. In some embodiments, the dimension of the channel is 1000 $\mu m^2$ and the gate electrode is 250000 $\mu m^2$. In one embodiment, the channel and gate each has a dimension of 100 $\mu m^2$. The source electrode and the drain electrode are placed apart and connected electronically by a corresponding channel. The channel contains one or more enzymes and one or more n-type polymers. In some embodiments, the source electrode and drain electrode can be bridged by the channel, wherein the length of the channel is between 1 $\mu m$ and 1000 $\mu m$. In one embodiment, the length of the channel bridging source electrode and drain electrode (i.e., the inter-electrode gap) is 10 $\mu m$. The gate electrode contains one or more n-type polymers and one or more enzymes. The gate electrode is placed separately from the source electrode, the drain electrode, and the channel to prevent electron flow between the gate electrode and the channel. The electrolyte solution is in electrical contact with the gate electrode and the channel. In the most preferred embodiments, the n-type polymers based electrochemical device has a planar configuration as shown in FIG. 1B and FIG. 8A. Alternatively, the gate electrode is not provided coplanar with the source and the drain electrodes and may be provided on a different layer of the supporting substrate or separately from the supporting substrate. In some embodiments, the electrochemical device contains a plurality of independently addressable source and drain electrodes, a common gate electrode, and corresponding channels, wherein the corresponding channels contain different enzymes for detecting multiple analytes simultaneously. In some embodiment, the n-type polymer based electrochemical device further includes a supporting substrate, and the source, drain, and gate electrodes can be patterned on the supporting substrate. In yet some other embodiments, the electrochemical device can be incorporated into a microfluidics configuration.

In one embodiment, a gate voltage ($V_G$) is applied and the metabolites react with the enzymes to produce the oxidized form of the metabolite and produces electrons, resulting in doping of the n-type polymers via direct electron transfer to the channel, increasing the conductivity of the polymers, thus increasing the saturating current that flows through the channel. The reduction of enzyme is reversible so enzymes are not consumed.

Optionally, the redox reactions can be irreversible if an electron mediator is added to provide additional reactant. A conductive substrate and an enzyme can be used wherein an electron mediator in contact with the channel is able to transfer electrons between its oxidized and reduced forms at the channel.

The disclosed n-type polymer based electrochemical device shows significantly improved stability, i.e., the same device can be used for multiple times over 6 months with no noticeable effect of degradation.

The n-type polymer based electrochemical device, in its simplest design, exhibits superior performances at physiologically relevant metabolite concentration, e.g. glucose and lactate, in that: (i) it avoids the tedious processes of synthetic or post-synthetic biofunctionalization involving complex chemistry, (ii) it does not need an electron mediator, (iii) it does not need a reference electrode, (iv) it is simple and scalable, (v) it can be miniaturized for a broad scope of applications in vitro and in vivo, (vi) it is highly sensitive to micromolar of metabolites, (vii) it is stable for at least 6 months, (viii) it has excellent selectivity to the metabolite of interest, (ix) its sensitivity is tunable according to the analyte range of choice (blood, saliva, sweat, and tears), and (x) it has a wide dynamic range. In some embodiments, the physiologically relevant concentration of glucose is between 0.1 $\mu M$ and 6.9 mM, inclusive. In one embodiment, the physiological relevant concentration of glucose is between 0.1 $\mu M$ and 20 mM, inclusive. The physiological concentration of glucose in different body fluids is disclosed in Bruen, et al., *Sensors*, 17:1866 (2017). In one embodiment, the physiological relevant concentration of lactate is between 10 $\mu M$ and 100 mM, inclusive. The physiological concentration of lactate in different body fluids is disclosed in Goodwin, et al., *J. Diabetes Sci. Technol.*, 1(4):558-569 (2007); Sakharov, et al., *Bulletin of Experimental Biology and Medicine*, 150(1):83-85 (2010); and Tekus, et al., *Acta Biol. Hung.*, 63(Suppl. 1):89-98 (2012).

A. Source and Drain Electrodes

The source and drain electrodes are made from materials capable of conducting an electric current. The electrode materials can be organic or inorganic in nature, as long as it is able to conduct electrons through the material. The electrodes can be a polymeric electrode, a metallic electrode, a semiconductor, a carbon-based material, a metal oxide, or a modified electrode. In some embodiments, the source and drain electrodes are made from an electrochemically inert material such as gold, platinum, or a conductive form of carbon, in order to prevent electrochemical corrosion upon operation whilst in contact with the electrolyte solution. In one embodiment, the electrodes are gold electrodes with an additional insulating layer such as Parylene C.

In some embodiments, the electrodes are made from a metallic conductor. Suitable metallic conductors include but are not limited to gold, chromium, platinum, iron, nickel, copper, silver, stainless steel, mercury, tungsten and other metals suitable for electrode construction. The metallic conductor can be a metal alloy which is made of a combination of metals disclosed above. In addition, conductive substrates which are metallic conductors can be constructed of nanomaterials made of gold, cobalt, diamond, and other suitable metals.

In other embodiments, the electrodes are made from carbon-based materials. Exemplary carbon-based materials are conducting polymers (in the form of films or fibers) carbon cloth, carbon paper, carbon screen printed electrodes, carbon paper, carbon black, carbon powder, carbon fiber, singe-walled carbon nanotubes, double-walled carbon nanotubes, multi-walled carbon nanotubes, carbon nanotube arrays, diamond-coated conductors, glassy carbon and mesoporous carbon. In addition, other exemplary carbon-based materials are graphene, graphite, uncompressed graphite worms, delaminated purified flake graphite, high performance graphite and carbon powders, highly ordered pyrolytic graphite, pyrolytic graphite, and polycrystalline graphite.

The electrodes can be semiconductors. Suitable semiconductors are prepared from silicon and germanium, which can be doped (i.e., the intentional introduction of impurities into an intrinsic semiconductor for the purpose of modulating its electrical and structural properties) with other elements. The semiconductors can be doped with phosphorus, boron, gallium, arsenic, indium or antimony, or a combination thereof.

Other electrode materials can be metal oxides, metal sulfides, main group compounds, and modified materials. Exemplary materials of this type are nanoporous titanium oxide, tin oxide coated glass, glass, cerium oxide particles, molybdenum sulfide, boron nitride nanotubes, aerogels modified with a conductive material such as gold, solgels modified with conductive material such as carbon, ruthenium carbon aerogels, and mesoporous silicas modified with a conductive material such as gold.

In another preferred embodiment, the electrodes contain one or more conducting materials. In embodiments where the electrodes containing two or more conducting materials, the first conducting material can be a conducting polymer and a second conducting material can be a material disclosed above. The conducting polymers include but are not limited to poly(fluorine)s, polyphenylenes, polypyrenes, polyazulenes, polynaphthalenes, poly(pyrrole)s, polycarbozoles, polyindoles, polyzaepines, polyanilines, poly(thiophene)s, poly(3,4-ethylenedioxythiophene), poly(p-phenylene sulfide), poly(acetylene)s, poly(p-phenylene vinylene), and polyimides. The second conducting material can be sputter coated on top of the conducting polymer, and the aggregate of the two makes up the conductive substrate. A preferred conductive substrate is a Kapton (polyimide) film sputter coated with Cr/Au.

The source and drain electrodes can be any shape appropriate such as rectangular, square, circular, and cylindrical. In a preferred embodiment, the electrodes are rectangular gold electrodes.

B. Channel

Generally, the channel electrochemically connects a pair of source and drain electrodes and contains elements that effect the oxidation of metabolites. The channel is arranged such that flow of electrons between the source electrode and the drain electrode is controllable by a voltage applied to the gate electrode. In some embodiments, the length of the channel is between 1 μm and 1000 μm, the width of the channel is between 1 μm and 1000 μm, and the thickness of the channel is between 50 nm and 1 μm. In a preferred embodiment, the channel bridging the source and the drain electrode has a dimension of 10 mm (length)×100 mm (width)×100 nm (thickness). In a n-type polymer based electrochemical device, the reaction that occurs at the channel is the oxidation of a compound such as a metabolite with a concurrent release of electrons; the electrons are transferred directly to the channel coated with the n-type polymers, increasing its conductivity, thereby turning the device on. To facilitate the specific oxidation of compounds such as metabolites, the channel contains one or more n-type polymers and one or more enzymes. In the most preferred embodiment, the n-type polymer is P90.

In one embodiment, the channel contains one or more polymeric materials and one or more enzymes. In another embodiment, the channel optionally further contains an electron mediator. An electron mediator can be absent from the channel when the channel contains a n-type polymer that is capable of interacting with the enzymes and promoting electron transfer from the oxidation reactions to the channel.

The above-identified components of the channel are adjacent to one another; meaning they are physically or chemically connected by appropriate means. In a preferred embodiment, the component are physically connected by coating such as by spin-coating, drop-casting, or electropolymerization. In one embodiment, electropolymerization may be performed in a solution containing one or more monomers of the corresponding polymers. In another embodiment, polymerization may be performed on a surface modified with monomers via potential triggering or stimulus such as UV light or temperature. The components can be deposited separately, e.g. in layers, or they can be integrated into one deposition layer.

1. N-Type Polymers

The polymeric material on the channel is any polymer that is capable of accepting (n-type) electrons produced in a reaction, resulting in increased charge carrier density and thus the conductivity of the polymer. The n-type polymer is a polymer capable of accepting electrons and stabilizing electrons on its backbone. Exemplary n-type polymers include N2300, P(NDI-T2), poly(diketopyrrolopyrrole) (DPP), poly(benzimidazobenzophenanthroline), poly(2,5-di(3,7-dimethyloctyloxy)cyanoterephthalylidene), poly(2,5-di(hexyloxy)cyanoterephthalylidene), poly(5-(3,7-dimethyloctyloxy)-2-methoxy-cyanoterephthalylidene), poly(2,5-di(octyloxy)cyanoterephthalylidene), and poly(5-(2-ethylhexyloxy)-2-methoxy-cyanoterephthalylidene).

In some embodiments, the polymers on the channel is a single n-type polymer or a combination of several n-type polymers or a combination of n-type polymers with p-type polymers or semiconductor materials. A p-type polymer is any polymer that is capable of donating electrons to a compound, resulting in the reduction of an oxidant. In a preferred embodiment, the p-type polymer is a robust oxygen reducer, and it reduces oxygen to water.

Exemplary p-type polymers include, but are not limited to, poly(3,4-ethylenedioxythiphene) (PEDOT), poly(hydrooxymethyl 3,4-ethylenedioxythiphene) (PEDOT-OH), polystyrenesulfonate (PSS), F8BT, F8T2, J51, MDMO-PPV, MEH-PPV, PBDB-T, PBDTBO-TPD, PBDT(EH)-TPD, PBDTTT-C-T, PBDTTT-CF, PBTTPD, PBTTT-C14, PCDTBT, PCPDTBT, PDTSTPD, PffBT4T-20D, PffBT4T-C9C13, PFO-DBT, Poly([2,6'-4,8-di(5-ethylhexylthienyl)benzo[1,2-b;3,3-b]dithiophene]{3-fluoro-2[(2-ethylhexyl)carbonyl]thieno[3,4-b]thiophenediyl}), Poly(3-dodecylthiophene-2,5-diyl), Poly(3-hexylthiophene-2,5-diyl), Poly(3-octylthiophene-2,5-diyl), PSiF-DBT, poly(triaryl amine) (PTAA), PTB7, TQ1, and a combination thereof. Semiconductor materials may be inorganic, metal-organic, or organic, and the semiconductor may comprise small molecules, oligomers, or polymers (Kugler, US 2009/0040587).

Figure 25A:
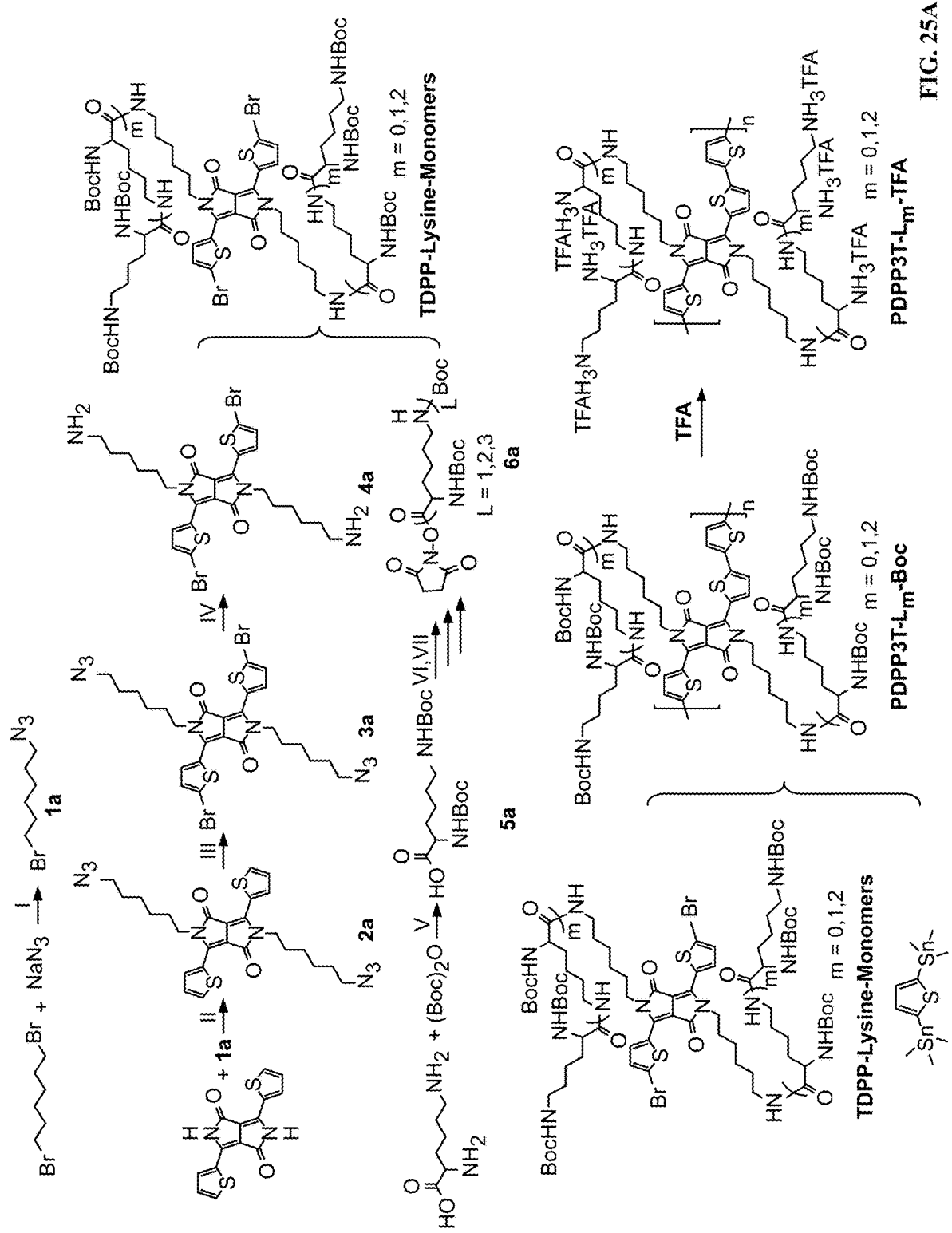
FIG. 25A is a scheme of lysine functionalization chemistry to prepare lysine side chains incorporated DPP polymer.
Figure 25B:
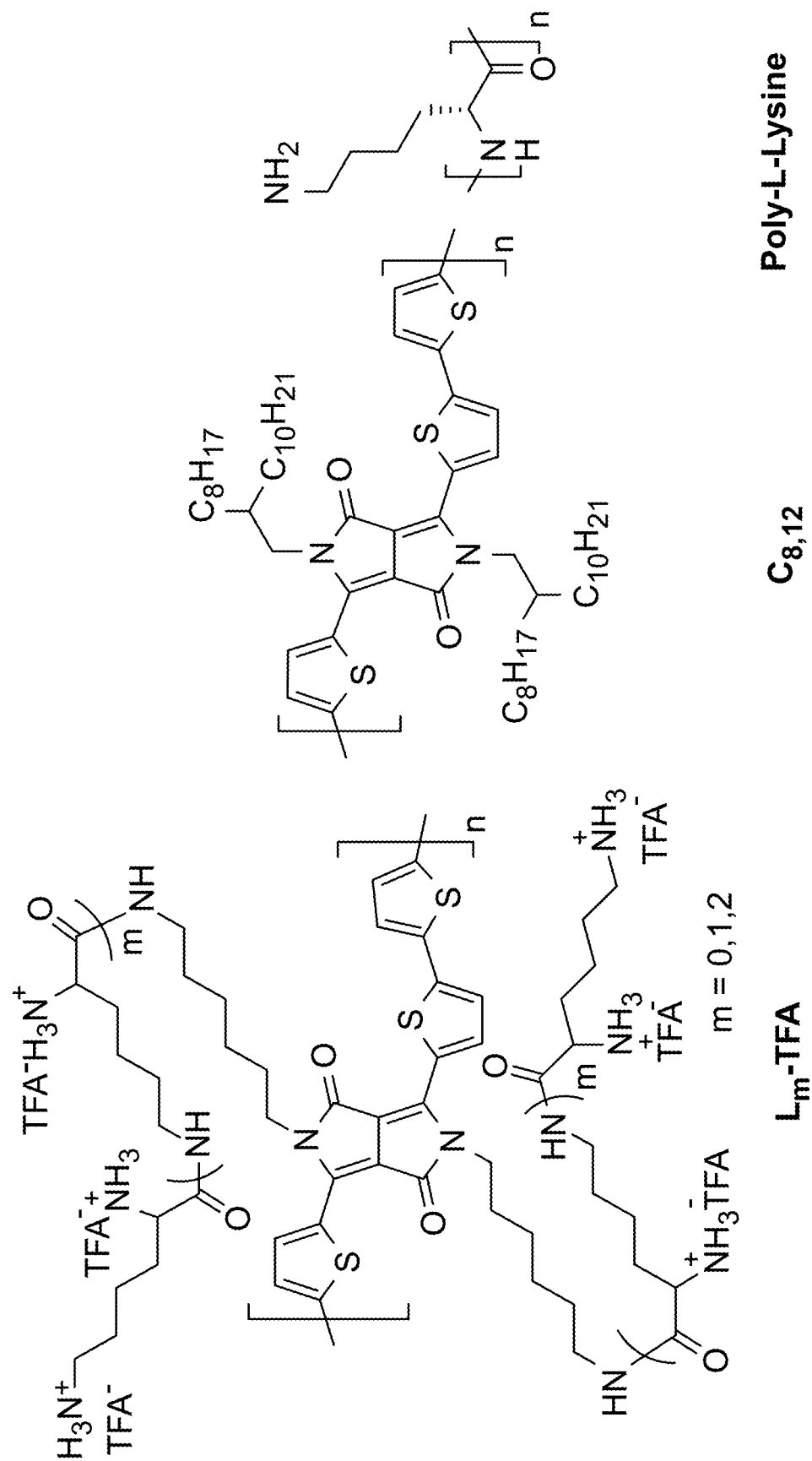
FIG. 25B shows the chemical structures of Lm-TFA and $C_{8,12}$ Poly-L-Lysine.
Figure 26A:
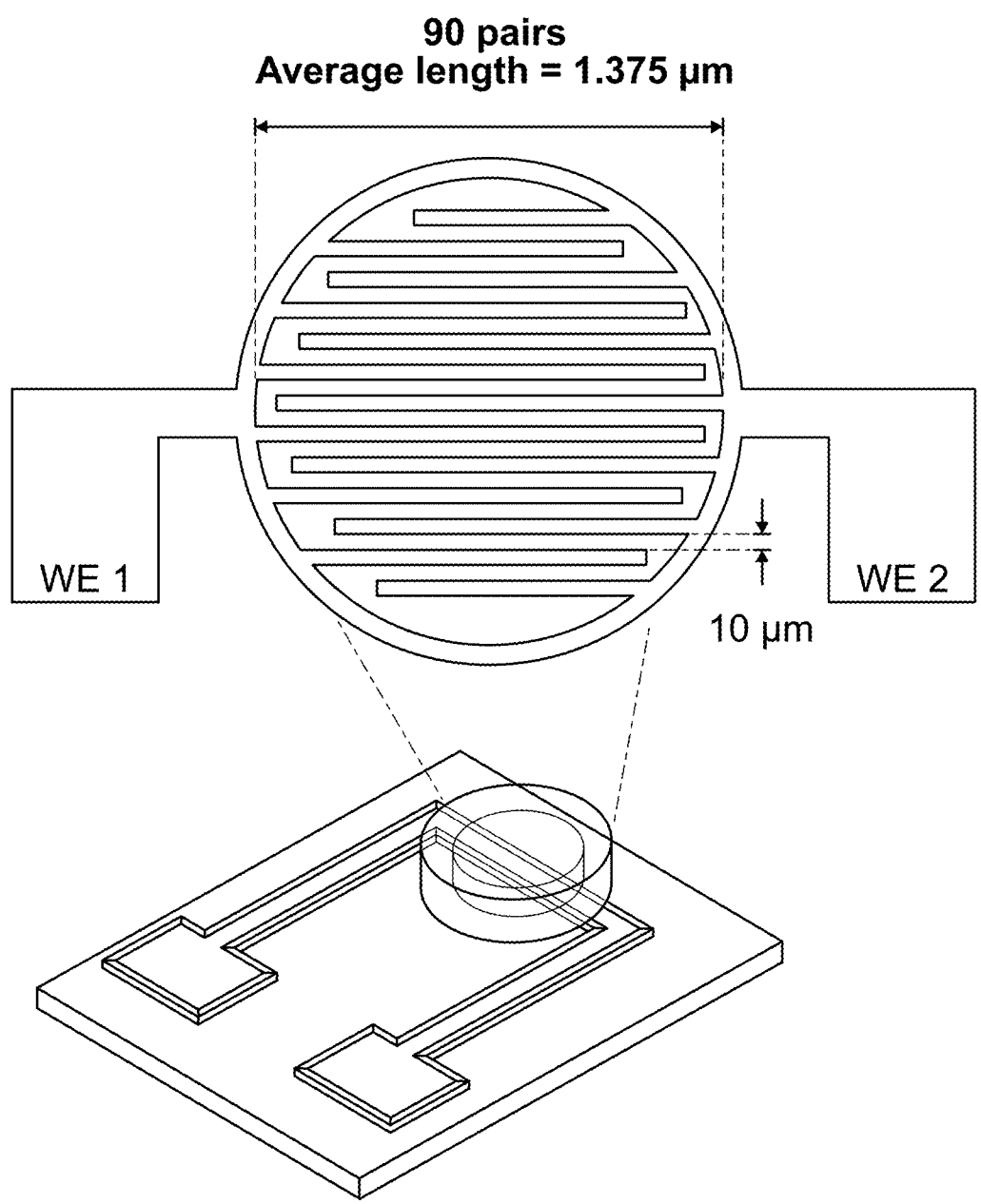
FIGS. 26A-D show the electrochemical behavior of the lysine functionalized DPP polymers.
Figure 26B:
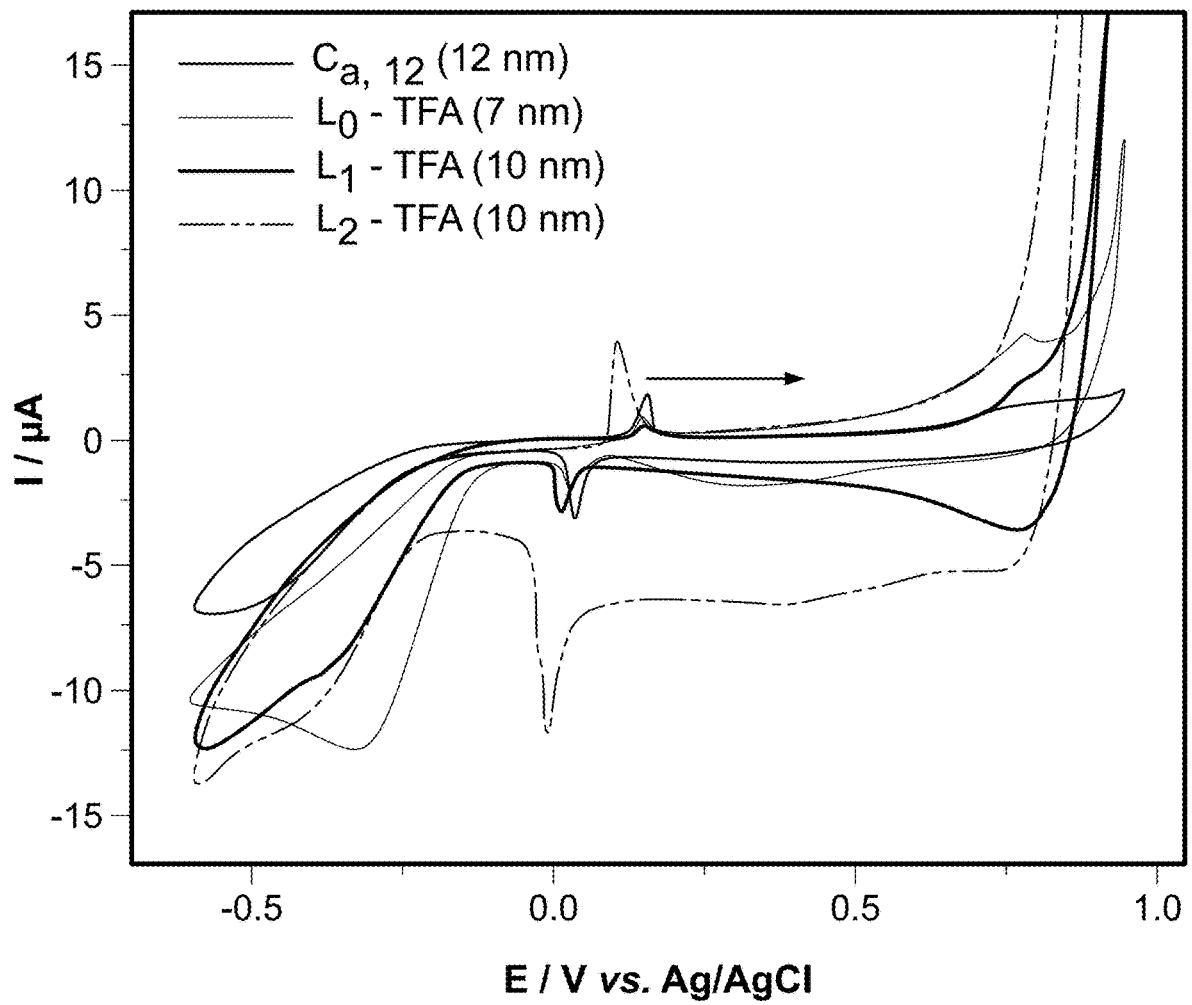
Figure 26C:
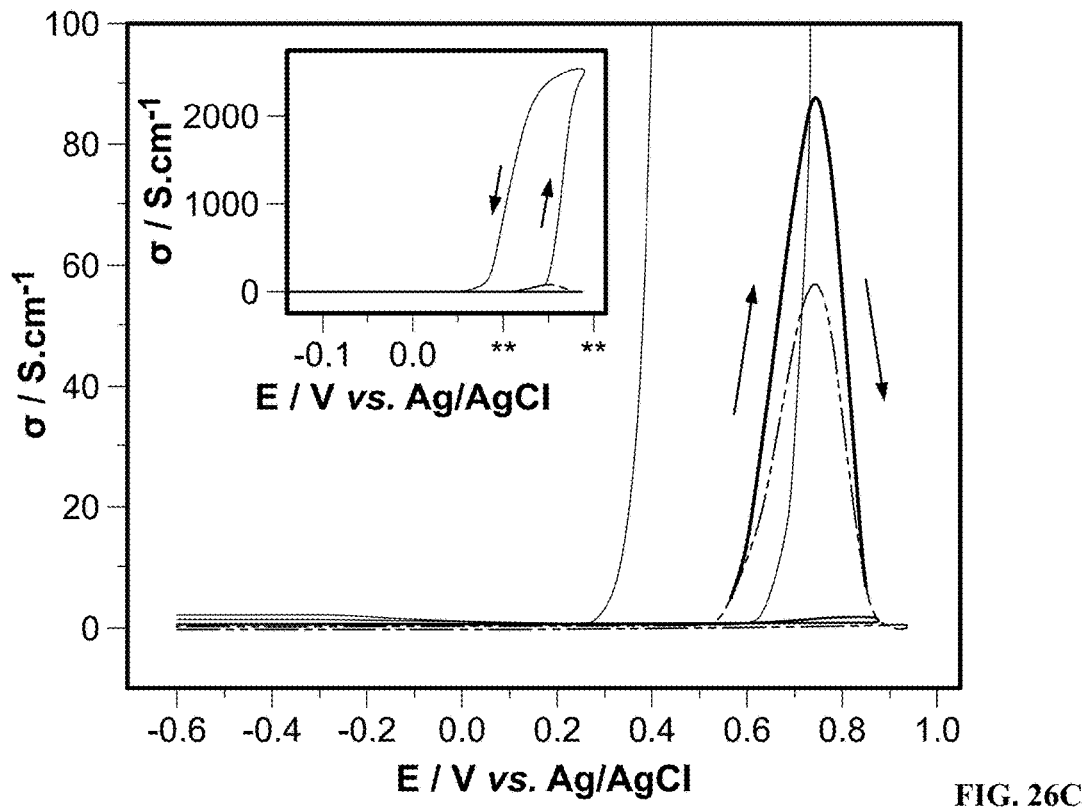
Figure 26D:
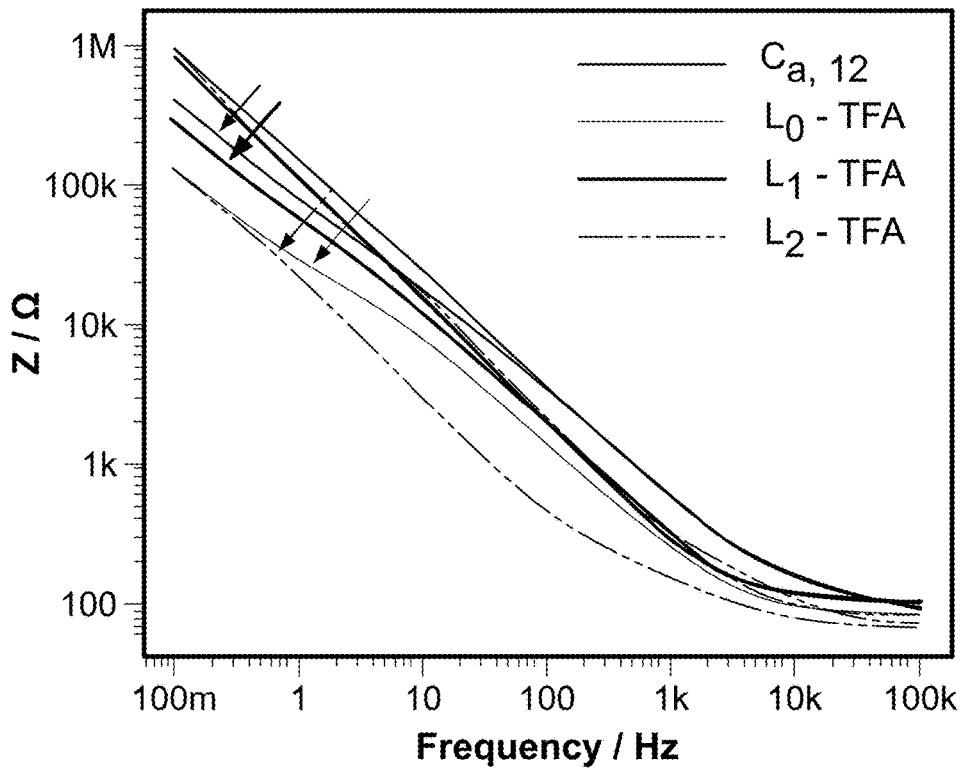

In some embodiments, the n-type polymer is a structure-modified polymer to introduce lysine side chains. In a particular embodiment, DPP polymers are modified to incorporate lysine side chains. To incorporate lysine side chains on the DPP polymer, a thienyl-DPP (TDPP) monomer containing amine functionality was used (FIGS. 25A and 25B). Introduction of lysine groups improves the electrochemical behavior of the DPP backbone, facilitates the ion penetration into the polymer bulk, thereof doping of the polymer by electrolyte ions, and increases the overall capacitance (FIGS. 26A to 26D). Functionalized polymers also exhibit more stable electrochemical behavior. Due to the presence of lysine groups on the surface, neurons attach, grow, and form a network without the need of an intermediate poly-D-lysine coating. Such functionalized polymers can also record/stimulate neural signals more effectively as the cells adhere to the protein-like surfaces (Du, et al., *Chemistry of Materials*, 30(17):6164-6172 (2018)).

In some embodiments, the n-type polymer is a structure-modified polymer to introduce polar groups. Exemplary polar groups include molecules with a single hydrogen, such as OH, molecules with at least one OH at one end, such as alcohol and alkylene glycol, and molecules with an N at one end, such as ammonia. In a preferred embodiment, the polar group is an alkylene glycol.

In the most preferred embodiment, the n-type polymer is P90, which is based on an NDI-T2 copolymer having a backbone comprising a highly electron-deficient naphthalene-1,4,5,8-tetracarboxylic diimide (NDI) repeat unit and an electron-rich unsubstituted bithiophene repeat unit (T2). (Giovannitti, et al., *Chemical Materials*, 30:2945-2953 (2018); Pappa, et al., *Science Advances*, 4:eaat0911 (2018)). The side chains on the diimide unit are a 90:10 randomly distributed ratio of polar glycol and nonpolar branched alkyl groups. Generally, the ratio of polar groups to nonpolar groups can be optimized to ensure solubility of the n-type polymer in polar solvents (Giovannitti, et al., *Chemical Materials*, 30:2945-2953 (2018)).

The polar groups such as the glycol side chains of P90 are envisaged to serve the dual role of (i) providing polar groups for the enzyme to interact with and (ii) enhancing the polymer's water uptake capacity to promote electrochemical activity in aqueous media (Al-Ani, et al., *Polymers*, 9:343 (2017); Yang, et al., *Journal of Polymer Science B Polymer Physics*, 43:1455-1464 (2005); Giovannitti, et al., *Proceedings of the National Academy of Sciences U.S.A.*, 113: 12017-12022 (2016)). The polar groups in the polymer structure play a key role in the promotion of the entrapment of the enzyme and enzyme stabilization on the polymer surface.

2. Enzymes

An enzyme is necessary in the n-type polymer based electrochemical device for metabolite sensing, to catalyze the oxidation of a metabolite of interest. Accordingly, useful enzymes at the channel are enzymes involved in oxidation. Generally, naturally-occurring enzymes, man-made enzymes, artificial enzyme, and modified naturally-occurring enzymes can be used. In addition, engineered enzymes that have been engineered by natural or directed evolution can be used. An organic or inorganic molecule that mimics an enzyme's properties can be used in an embodiment of the present disclosure. Exemplary enzymes for use in a bioanode include glucose oxidase, glucose dehydrogenase, alcohol dehydrogenase, aldehyde dehydrogenase, formate dehydrogenase, formaldehyde dehydrogenase, lactic dehydrogenase, lactose dehydrogenase, lactate oxidase, cholesterol oxidase, tyrosinase, and pyruvate dehydrogenase. In a preferred embodiment, the enzyme is glucose oxidase. In another preferred embodiment, the enzyme is lactate oxidase.

Strategies for biofunctionalization of channel/electrode surface with enzymes include: physical adsorption (i.e. spin-coating and drop-casting), covalent immobilization, cross-linking, affinity linking, and entrapment (Saboe, et al., *Energy & Environmental Science*, 10:14-42 (2017); Banica, *Chemical Sensors and Biosensors: Fundamentals and Applications*, John Wiley & Sons Ltd, United Kingdom (2012); Yates, et al., *Chemistry: A European Journal*, 24(47):12164-12182 (2018); Mateo, et al., *Enzyme and Microbial Technology*, 40(6):1451-1463 (2007); Sheldon, *Advanced Synthesis & Catalysis*, 349(8-9):1289-1307; Rocchitta, et al., *Sensors*, 16(6):780 (2016)). In a preferred embodiment, the enzyme is drop-casted on top of a channel coated with n-type polymers. Methods of drop casting enzyme solutions onto a surface are known in the art (Pappa, et al., *Science Advances*, 4(6):eaat0911 (2018)). The enzyme is efficiently anchored to the surface of the polymer because of the structure of the polymer. The polar groups of the polymer facilitate interactions of the enzyme with the polymer and bring the enzyme in close proximity to the surface of the conductive substrate (Inal, et al., *ACS Applied Bio Materials*, 1(5):1348-1354 (2018)). The efficient immobilization of the enzyme allows good electrical contact with the polymer, so the electrons generated from the enzymatic reaction can be transferred directly from the redox center to the polymer backbone. Direct electrical communication between the polymer and the enzyme enables mediator-free direct electron transfer. In a particularly preferred embodiment, biofunctionalization of the electrode surface does not require complex chemistry, i.e. covalent immobilization, cross-linking, or affinity linking.

C. Gate Electrode

Generally, the gate electrode is made from a material descried above for the source and the drain electrodes. The gate electrode can be any shape appropriate such as rectangular, square, circular, and cylindrical. In some embodiments, the gate electrode has a dimension between 100 $\mu m^2$ and 250000 $\mu m^2$. In a preferred embodiment, the electrodes are rectangular with a dimension of 500 $\mu m^2$. The gate electrode is placed separately from the source, the drain, and the channel and contains elements that effect the oxidation of metabolites. The oxidation of a compound such as a metabolite with a concurrent release of electrons; the electrons are transferred directly to the gate electrode coated with the n-type polymers, increasing its conductivity. In one embodiment, the gate electrode contains one or more n-type polymers and one or more enzymes. Polymers and enzymes described above can be used. The polymers and enzymes of the gate electrode can be the same or different from the polymers and enzymes at the channel. In another embodiment, the gate electrode optionally further contains an electron mediator. An electron mediator can be absent from the gate electrode when the gate electrode contains a n-type polymer that is capable of interacting with the enzymes and promoting electron transfer from the oxidation reactions to the gate electrode.

The above-identified components of the channel are adjacent to one another; meaning they are physically or chemically connected by appropriate means. In a preferred embodiment, the component are physically connected by coating such as by spin-coating, drop-casting, or electropolymerization. In one embodiment, electropolymerization may be performed in a solution containing one or more monomers of the corresponding polymers. In another embodiment, polymerization may be performed on a surface modified with monomers via potential triggering or stimulus such as UV light or temperature. The components can be deposited separately, e.g. in layers, or they can be integrated into one deposition layer.

In a n-type polymer based electrochemical device, a gate voltage ($V_G$) is applied to dope the polymer film caused by the cations injected from the electrolyte solution, resulting in a baseline source-drain current ($I_{BD}$), which is unrelated to the enzymatic reactions. The oxidation of a compound such as a metabolite with enzymes produces electrons that are directly transferred to the n-type polymers on the gate electrode and increase the polymers' conductivity thus leading to increased $I_D$ (signal output). In some embodiments, a constant $V_G$ is applied to the electrochemical device for metabolite sensing. In some embodiments, $V_G$ equal to or higher than a threshold voltage, that is, the minimum $V_G$ required to result in a $I_D$ in the absence of an enzymatic reaction, i.e. oxidation reaction between enzymes and metabolites. In one particular embodiment, the threshold voltage is 0.5 V. In some embodiments, the $I_D$ increases with increasing $V_G$. Giovannitti and co-workers (Giovannitti, et al., *Nature Communications*, 7:13066 (2016)) recently showed that the polar glycol side chains attached to n-type polymer backbones enabled reversible electrochemical switching between the reduced (n-type-doped), oxidized (p-type-doped), and neutral state of the film in similar aqueous electrolytes. During the reduction process (triggered by a positive gate bias), cations drift into the film to counterbalance the electrons stabilized on the backbone of the copolymer.

D. Electrolyte Solution

The electrolyte solution is in electrically contact with the channel and the gate electrode. The electrolyte solution is a solution that contains ions, atoms, or molecules that have lost or gained electrons, and is electrically conductive. Electrolyte solutions include but are not limited to buffers such as phosphate buffer solution (PBS), salt water, MES buffer, Bis-Tris buffer, ADA, ACES, PIPES, MOPSO, Bis-Tris propane, BES, MOPS, TES, HEPES, DIPSO, MOBS, TAPSO, Trizma, HEPPSO, POPSO, TEA, EPPS, Tricine, Gly-gly, Bicine, HEPBS, TAPS, AMPD, TABS, AMPSO, CHES, CAPSO, AMP, CAPS, CABS, or a combination thereof; biological fluids such as whole blood, serum, urine, saliva, sweat; and a combination of buffers and biological fluids. The electrolyte solution has a pH between 6 and 8.5. In the most preferred embodiment, the electrolyte solution has a pH of 7.4.

The electrolyte solution contains one or more metabolites that react with the enzymes at the channel and the gate to produce electrons. The metabolites are consumed in the oxidation reaction with the enzymes. Exemplary metabolites are glucose, glucose-1, D-glucose, L-glucose, glucose-6-phosphate, ammonia, methanol, ethanol, propanol, isobutanol, butanol and isopropanol, allyl alcohols, aryl alcohols, glycerol, cholesterol, propanediol, mannitol, glucoronate, aldehyde, carbohydrates, lactate, lactate-6-phosphate, D-lactate, L-lactate, fructose, galactose-1, galactose, aldose, sorbose, mannose, glycerate, coenzyme A, acetyl Co-A, malate, isocitrate, formaldehyde, acetaldehyde, acetate, citrate, L-gluconate, beta-hydroxysteroid, alpha-hydroxysteroid, lactaldehyde, testosterone, gluconate, fatty acids, lipids, phosphoglycerate, retinal, estradiol, cyclopentanol, hexadecanol, long-chain alcohols, coniferyl-alcohol, cinnamyl-alcohol, formate, long-chain aldehydes, pyruvate, butanal, acryl-CoA, steroids, amino acids, favin, NADH, $NADH_2$, NADPH, $NADPH_2$, and hydrogen. In a preferred embodiment, the metabolite is glucose, glucose-1, D-glucose, L-glucose, or glucose-6-phosphate. In one particular embodiment, the metabolite is glucose. In another preferred embodiment, the metabolite is lactate, lactate-6-phosphate, D-lactate, or L-lactate. In another particular embodiment, the metabolite is lactate.

E. Supporting Substrate

In some embodiments, a supporting substrate is used to support the source, drain, gate electrodes and the channel. In some embodiments, the components identified above are patterned on a single layer of the supporting substrate. In the most preferred embodiments, the n-type polymers based electrochemical device has a planar configuration as shown in FIG. 1B and FIG. 8A. Alternatively, the gate electrode is not provided coplanar with the source and the drain electrodes and may be provided on a different layer of the supporting substrate or separately from the supporting substrate. In some embodiments, a plurality of independently addressable source and drain electrodes, a common gate electrode, and corresponding channels are patterned on the supporting substrate, wherein the corresponding channels contain different enzymes for detecting multiple analytes simultaneously. Exemplary supporting substrates are glass, polyethylene terephthalate, polyethylene naphthalene dicarboxylate, polyethylene, polypropylene, polycarbonate, paper, coated paper, resin-coated paper, paper laminates, paperboard, and corrugated board.

In one embodiment, the components are physically and chemically connected with the supporting substrate. In a preferred embodiment, the component are physically connected with the supporting substrate by coating such as by sput-coating, spin-coating, drop-casting, or otherwise deposing the individual components on the supporting substrate (Libansky, et al., *Electrochimica Acta*, 251:452-460 (2017)).

F. Electron Mediator

Optionally, an electron mediator can be used in the n-type polymer based electrochemical device. The electron mediator is a compound that can accept or donate electrons. The electron mediator can be attached onto the channel and the gate electrode. Exemplary electron mediators are pyrroloquinoline quinone (PQQ), phenazine methosulfate, dichlorophenol indophenol, short chain ubiquinones, potassium ferricyan, or equivalents of each.

III. Methods of Making the N-Type Polymer Based Electrochemical Device

N-type polymer based electrochemical devices disclosed herein include one or more source electrodes, one or more drain electrodes, one or more channels, a gate electrode, and an electrolyte solution containing one or more metabolites. The source electrode and the drain electrode are placed apart and connected electronically by the corresponding channel. The channel contains one or more enzymes and one or more n-type polymers. In some embodiments, the source electrode and drain electrode can be bridged by the channel, wherein the length of the channel is between 1 μm and 1000 μm. In one embodiment, the length of the channel bridging source electrode and drain electrode (i.e., the inter-electrode gap) is 10 μm. The gate electrode contains one or more n-type polymers and one or more enzymes. The gate electrode is placed separately from the source electrode, the drain electrode, and the channel to prevent electron flow between the gate electrode and the channel. The electrolyte solution is in electrical contact with the gate electrode and the channel. In the most preferred embodiments, the n-type polymers based electrochemical device has a planar configuration as shown in FIG. 1B and FIG. 8A. Alternatively, the gate electrode is not provided coplanar with the source and the drain electrodes and may be provided on a different layer of the supporting substrate or separately from the supporting substrate. In some embodiments, the electrochemical device contains a plurality of independently addressable source and drain electrodes, a common gate electrode, and corresponding channels, wherein the corresponding channels contain different enzymes for detecting multiple analytes simultaneously.

In some embodiments, the n-type polymers and enzymes of the channel and the gate are adjacent to one another; meaning they are physically or chemically connected by appropriate means. In a preferred embodiment, the component are physically connected by coating such as by spin-coating, drop-casting, or electropolymerization. In one embodiment, electropolymerization may be performed in a solution containing one or more monomers of the corresponding polymers. In another embodiment, polymerization may be performed on a surface modified with monomers via potential triggering or stimulus such as UV light or temperature. The components can be deposited separately, e.g. in layers, or they can be integrated into one deposition layer.

In some embodiments, the n-type polymer based electrochemical device further includes a supporting substrate and the source, drain, and gate electrodes can be patterned on the supporting substrate. In some other embodiments, the electrochemical device can be incorporated into a microfluidics configuration. In one embodiment, the components are physically and chemically connected with the supporting substrate. In a preferred embodiment, the component are physically connected with the supporting substrate by coating such as by sputt-coating, spin-coating, drop-casting, or otherwise deposing the individual components on the supporting substrate.

In a preferred embodiment, gold contacts (located at the source, drain and gate) and interconnects were patterned on a glass substrate while an additional layer of Parylene C was used to insulate the gold interconnects according to established protocol (Nielsen, et al., *Journal of the American Chemical Society*, 138:10252-10259 (2016); Sessolo, et al., *Advanced Materials*, 25(15):2135-2139 (2013)). The final channel dimension is 10 µm in length and 100 µm in width. The gate electrode has an active area of 500 µm². The active material, P-90, was spin-casted (1000 rpm, 30 s) directly from a chloroform solution without any annealing or post processing steps. The polymer P-90 was synthesized according to the literature (Giovannitti, et al., *Chem. Mater.*, 30:2945-2953 (2018)).

IV. Methods of Using the N-Type Polymer Based Electrochemical Device

One of the various aspects of the disclosed n-type polymer based electrochemical device is a method of detecting metabolites. In a n-type polymer based electrochemical device, a gate voltage ($V_G$) is applied to dope the polymer film caused by the cations injected from the electrolyte solution, resulting in a baseline source-drain current ($I_{BD}$), which is unrelated to the enzymatic reactions. The oxidation of a compound such as a metabolite with enzymes produces electrons that are directly transferred to the n-type polymers on the gate electrode and the channel. The n-type polymers have conjugated backbone that have the ability to stabilize electrons. Enzymatic reactions increase the charge carrier density and thus the conductivity of the channel, leading to increased $I_D$ (signal output), thereby turning the device on. In some embodiments, a constant $V_G$ is applied to the electrochemical device for metabolite sensing. In some embodiments, $V_G$ equal to or higher than a threshold voltage, that is, the minimum $V_G$ required to result in a $I_D$ in the absence of an enzymatic reaction, i.e. oxidation reaction between enzymes and metabolites. In one particular embodiment, the threshold voltage is 0.5 V.

The n-type polymer based electrochemical device can be used for both in vitro and in vivo applications. In one embodiment, the electrochemical device can be used as an in vivo sensing device for measuring metabolites such as glucose and/or lactate from the blood stream. Such in vivo electrochemical sending devices may be utilized as an implanted device for continuously monitoring a single metabolite or multiple metabolites simultaneously, wherein the metabolites are derived from the organism. In another embodiment, the electrochemical device can be used as in vitro as portable devices and/or wearable electronics that measure metabolites, including, but not limited to, glucose and lactate.

In another embodiment, a method of detecting metabolites using the n-type polymers based electrochemical device is disclosed, which contains the steps of (a) applying a gate potential ($V_G$), (b) electron transferring from the enzymes to the n-type polymers during an enzymatic reaction between the enzymes and the metabolites in the electrolyte solution, and (c) monitoring changes of a source-drain current ($I_D$) that flows through the channel that connects the source electrode and the drain electrode. The $I_D$ changes with the change of metabolite concentration. In a preferred embodiment, the $I_D$ increases with the increase of metabolite concentration. In some embodiments, the $V_G$ equal to or higher than a threshold voltage. In a preferred embodiment, the threshold voltage is 0.5 V. In some embodiments, the sensor sensitivity is tunable by varying the biasing conditions to fit the analyte range of choice in different body fluids such as blood, saliva, sweat, and tears (Pappa, et al., *Science Advances*, 4(6):eaat0911 (2018)).

In a preferred embodiment, n-type polymer based electrochemical devices are fabricated using (a) gold source and drain electrodes, (b) GOx and n-type polymer coated channel, (c) GOx and n-type polymer coated gold gate electrode, and (d)phosphate buffer solution containing glucose wherein the glucose is at a physiological relevant concentration. Electrochemical devices employing these components have demonstrated responsive to nanomolar concentration of glucose and a wide dynamic range of detection from 100 nM to 20 mM and also high reversibility. For example, when the glucose solution is replaced with buffer solution, the current reverts to its original value. The electrochemical device are stable for 6 months.

In another preferred embodiment, n-type polymer based electrochemical devices are fabricated using (a) gold source and drain electrodes, (b) LOx and n-type polymer coated channel, (c) LOx and n-type polymer coated gold gate electrode, and (d) phosphate buffer solution containing lactate wherein the glucose is at a physiological relevant concentration. Electrochemical devices employing these components have demonstrated responsive to micromolar concentration of lactate and a wide dynamic range of detection from 10 µM to 10 mM and also high reversibility. The electrochemical device are stable for 6 months.

The present invention will be further understood by reference to the following non-limiting examples.

EXAMPLES

It is demonstrated for the first time the use of n-type conjugated polymers in an accumulation mode electrochemical device for the direct detection of metabolites. The detection is based on direct electron transfer between the enzyme and the polymers. The n-type polymers based electrochemical device is greatly simplified, obviating the need for synthetic or post-synthetic biofunctionalization that involves complex chemistry, mediators, and a reference electrode. The use of a lateral micrometer-scale gate electrode based on the n-type polymer and elimination of an external reference electrode allow for straightforward adaptation of this device type into different geometries and forms for both in vitro and in vivo applications. The device also exhibits improved performance such as high sensitivity, wide dynamic range, tunable sensitivity according to the analyte range of choice (blood, saliva, sweat, and tears), excellent selectivity, and improved operational stability and a shelf life of 6 months. The role of OECT as both the amplifier and transducer and the design simplicity endowed by the inherent surface and bulk properties of the n-type material poise the resulting platform as a prominent alternative to the conventional amperometric enzyme electrodes.

Example 1. N-Type OECT Allows for Direct Detection of Glucose

Materials and Methods

For the device fabrication, the gold contacts (located at the source, drain and gate) and interconnects were patterned on a glass substrate while an additional layer of Parylene C was used to insulate the gold interconnects according to established protocol (Sessolo, et al., *Advanced Materials*, 25(15):2135-2139 (2013)). The final channel dimension is 10 μm in length and 100 μm in width. The active material, P-90, was spin casted (1000 rpm, 30 s) directly from a chloroform solution without any annealing or post processing steps.

For the sensing experiments, GOx in PBS (10 mg mL$^{-1}$) was drop-casted on the device active area (channel and gate). Glucose was dissolved as stock solutions in PBS. Current-voltage characteristics of the devices were recorded using a Keithley 2602A dual SourceMeter. The readout signal of the OECT at zero analyte concentration was the steady-state current obtained in the PBS solution. After a steady baseline was obtained for the drain current, changes in response to subsequent additions of increasing concentrations of lactate solutions into the electrolyte were monitored as a function of time. For all experiments, the volume of the solution was kept at 40 μL. The response of the device to glucose was normalized to allow for an accurate comparison between different devices. The normalized response (NR) was determined by the equation (1), which takes into account the current output after it reaches a steady-state value:

$$NR = \left| \frac{I}{I_{max}} \right| \quad (1)$$

where I and $I_{max}$ are the current output at a given analyte concentration and the maximum current output of the device at the analyte saturation concentration, respectively.

Results

The sensor is composed of an n-type semiconductor coated OECT (Pappa, et al., *Trends in Biotechnology*, 36(1): 45-59 (2017); Inal, et al., *Nature Communications*, 8(1): 1767 (2017)) while the active material is a n-type conjugated polymer based on a naphthalene-1,4,5,8-tetracarboxylic-diimide-bithiophene (NDI-T2) copolymer (Chen, et al., *Journal of the American Chemical Society*, 131(1):8-9 (2009)) consisting of alternating naphthalene dicarboximide (NDI) acceptor and bithiophene (T2) donor subunits (FIG. 1). Engineering of the side chains by introducing non-polar branched alkyl and polar glycol groups, in a 10:90 random distribution, enhances the polymer's swelling properties (P90) (Pappa, et al., *Trends in Biotechnology*, 36(1):45-59 (2017)) and thereof its electrochemical activity, while in the same time provide polar groups for enzyme interaction (Freire, et al., *Journal of the Brazilian Chemical Society*, 14:230-243 (2003)). The copolymer P90 stabilizes electrons on its backbone and due to its ability to efficiently host enzymes, direct electron transfer between the active center of the enzyme and the copolymer can be realized, leading to its electrochemical doping upon analyte oxidation (FIG. 1). This allows the copolymer to function in accumulation mode (Rivnay, et al., *Nature Reviews Materials*, 3:17086 (2018)), enabling the device to "turn ON" only upon electrochemical doping, contrary to depletion mode devices.

Figure 1B:
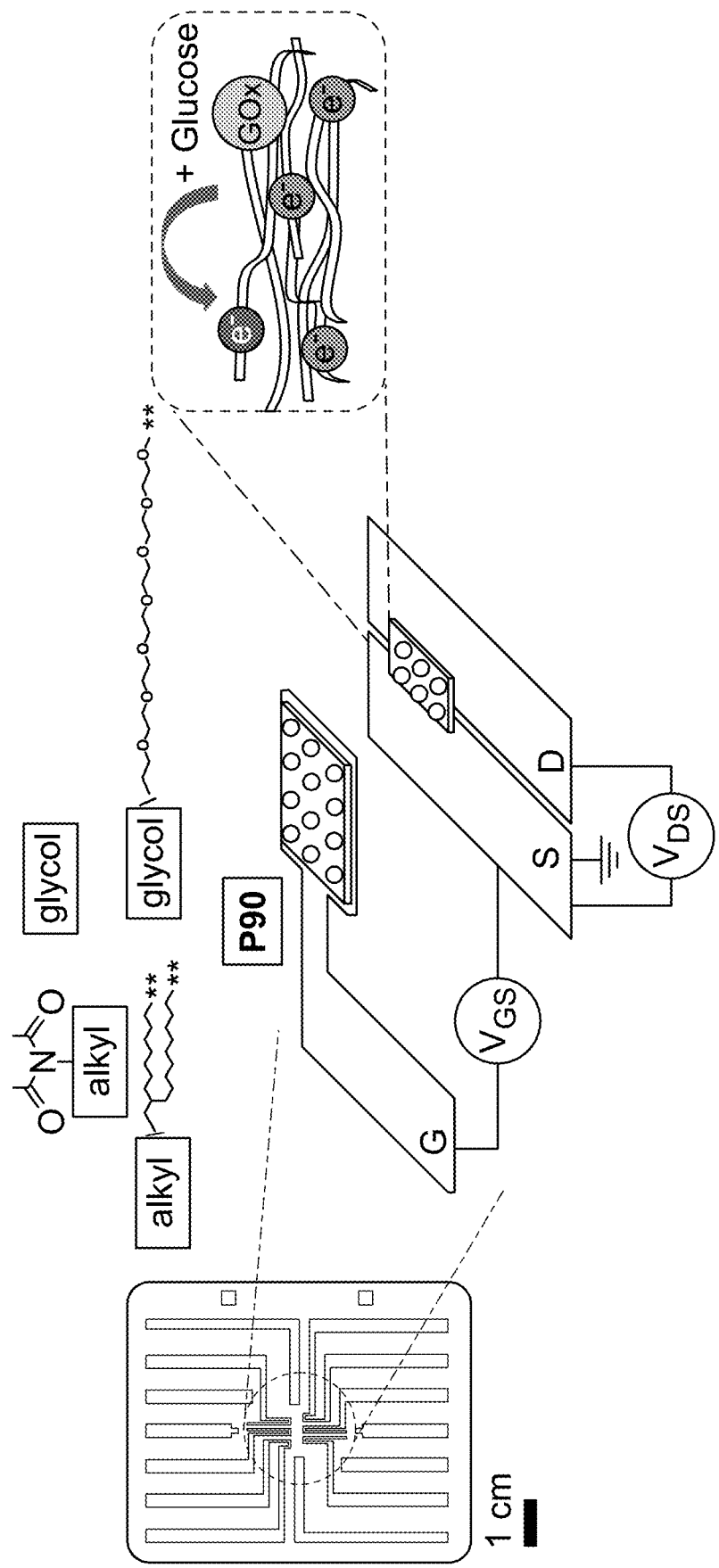
Figure 2:
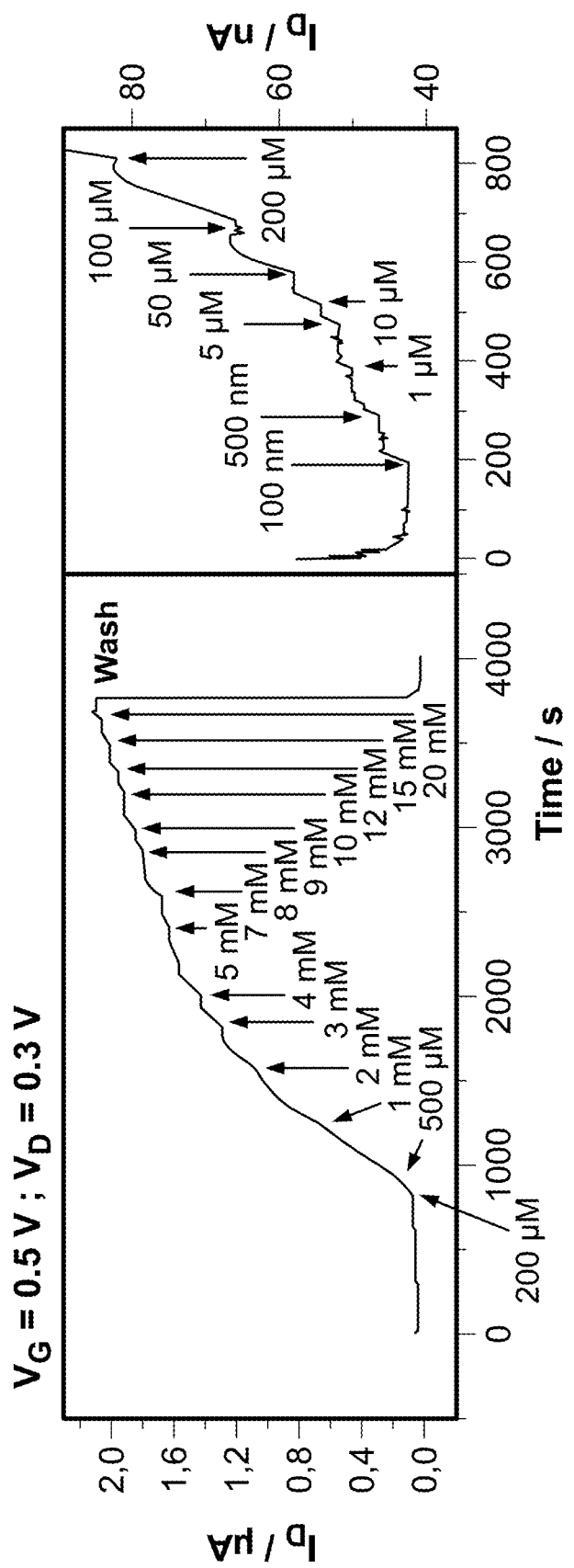
FIG. 2 shows a graph of the real-time response of the OECT (source-drain current, $I_D$, as a function of time) as successive amounts of glucose are added to the buffer saline solution in presence of the enzyme GOx.

The P90-based OECT is here functionalized with glucose oxidase (GOx) (FIGS. 1A and 1B). GOx is simply drop-casted on top of the device without any prior surface treatment. The real-time response of the OECT to increasing glucose concentration is shown in FIG. 2 where the drain current $I_D$ increases with analyte concentration. The GOx redox center (Flavin adenine dinucleotide (FAD/FADH$_2$) reacts with the glucose analyte and is reduced from FAD to FADH$_2$ while glucose get oxidized to gluconolactone via a two electron transfer process (Wang, et al., *Chemical Reviews*, 108(2):814-825 (2008)). Then, the electrons produced from the glucose oxidation are transferred to the P90 polymer, leading to an increase in the polymer conductivity. The device demonstrates a good response throughout a respectable dynamic range (100 nM to 20 mM) and also high reversibility. For instance, when the 20 mM glucose solution is replaced with buffer solution ("Wash"), the current reverts to its original value (FIG. 2). The detection of glucose occurs quite rapidly for low analyte concentrations. Direct electron transfer is normally very slow as a consequence of steric insulation of the redox center of the protein (Madou, *Solid-State Physics, Fluidics, and Analytical Techniques, in Micro- and Nanotechnology*, Taylor & Francis (2011)), highlighting the good contact between the redox center of GOx and P90. However, we observe a longer time for saturation of the current at higher glucose concentrations (mM range), attributed to the enzyme kinetics and its regeneration with ambient oxygen (Bambhania, et al., *Journal of The Electrochemical Society*, 164(4):H232-H240 (2017)). The device response to glucose is reproducible in terms of sensitivity and dynamic range despite probable device to device variations in the current response that are ascribed to thickness variation of the copolymer P90 in the channel. OECTs properties are governed by polymer thickness (Rivnay, et al., *Science Advances*, 1(4):e1400251 (2015)) whilst fabrication optimization can easily address these effects (Braendlein, et al., *Advanced Materials*, 29(13): 1605744 (2017)).

Example 2. The n-Type OECT Sensing Sensitivity is Tunable by Varying the Biasing Conditions Materials and Methods OECT response is governed by its gain (Rivnay, et al., *Nature Reviews Materials*, 3:17086 (2018); Inal, et al., *Nature Communications*, 8(1):1767 (2017)), which in turn depends on the bias applied. It is possible to tune the sensor sensitivity by varying the biasing conditions (Pappa, et al., *Science Advances*, 4(6):eaat0911 (2018)). In accumulation mode OECT, the magnitude of the bias applied dictates at which interface (gate or channel) the enzymatic reaction will occur, as opposed to classic depletion mode sensors where the reaction is always happening at the positively biased gate electrode. Three different combinations of gate and drain bias were tested herein, namely $V_G>V_D$, $V_D>V_G$ and $V_D=V_G$.

Results

Figure 3:
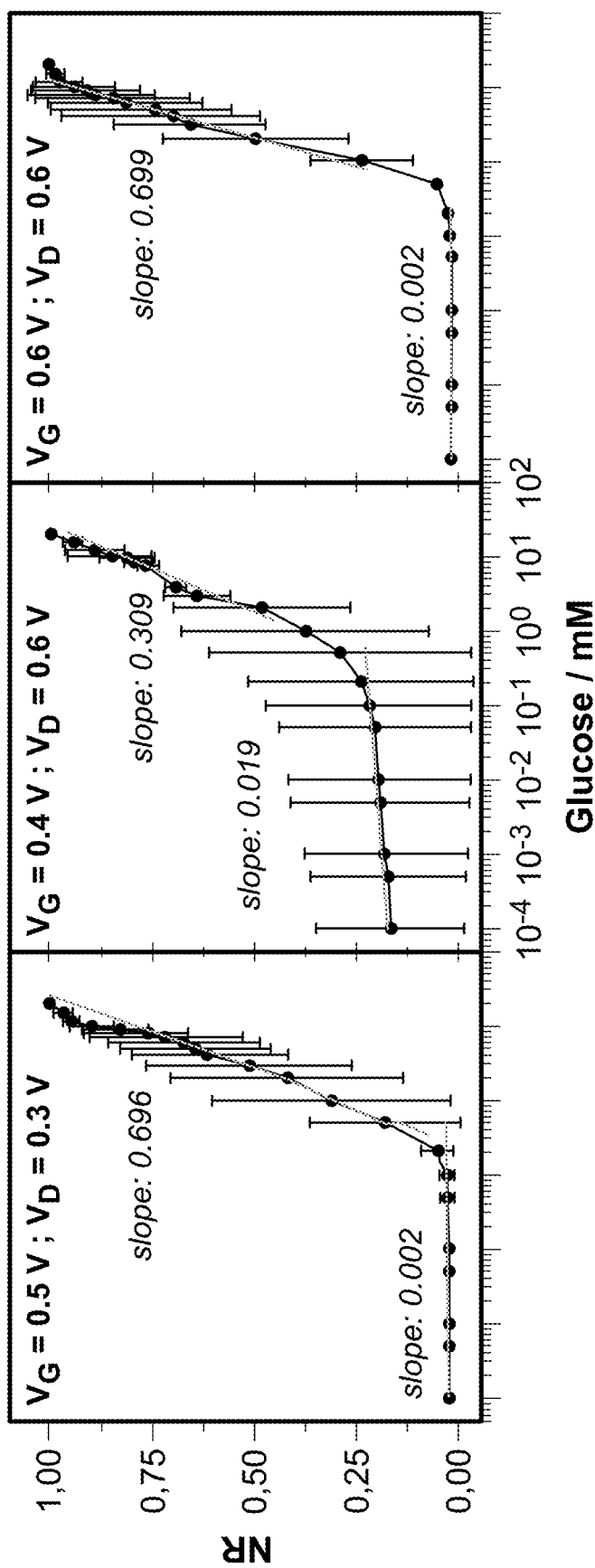
FIG. 3 shows graphs of normalized response (NR) of the OECT to glucose in the presence of GOx under different bias conditions: $V_G>V_D$, $V_D>V_G$ and $V_D=V_G$. The log scale was implemented so as to better appreciate the response to low concentrations.

FIG. 3 displays the calibration curves obtained for different gate and drain bias couples. All three conditions display the same dynamic range but different sensitivities for specific analyte concentration ranges. Moreover, two linear dependences for different glucose ranges can be extracted for all conditions. From the slope of the calibration curves, it is evident that the device shows better sensitivity towards low glucose concentrations when operating with a drain voltage higher than the gate voltage. However, when the gate voltage is larger than the drain voltage, the device exhibits better sensitivity to high glucose concentration (mM range). Due to the design and micron-scale of the device, both gate and channel are fully covered when drop-casting the GOx solution. Therefore it is hard to decouple the contribution of each element to the sensing performance. As a case in point, we calculated the Michaelis-Menten constant ($K_m^{app}$) from the sensing experiment in FIG. 2, as an indicator of enzyme-substrate kinetics and affinity. The smaller the $K_m^{app}$ value, the higher the affinity of the electrode to the substrate. The apparent constant can be calculated from the Lineweaver-Burk equation (Lineweaver, et al., *Journal of The American Chemical Society*, 56(3): 658-666 (1934)) (2):

$$\frac{1}{\Delta I_D} = \frac{K_M^{app}}{\Delta I_{max}} * \frac{1}{c} + \frac{1}{\Delta I_{max}} \quad (2)$$

where $\Delta I_D$ is the steady state current after addition of glucose, c is the glucose concentration and $\Delta I_{max}$ is the maximum current measured at analyte saturation. $K_m^{app}$ was determined from the slope and the intercept of the plot ($1/\Delta I_D$) vs ($1/c$). It is found that $K_m^{app}$ equals to 4.25 µM, much smaller than GOx entrapped in carbon nanotubes (Kang, et al., *RSC Advances*, 7(8):4572-4579 (2017)) or nanodots (Zhao, et al., *Analytical Chemistry*, 87(5):2615-2622 (2015)), immobilized on gold nanoparticles (Zhang, et al., *Sensors and Actuators B: Chemical*, 109(2):367-374 (2005); Zhang, et al., *Bioelectrochemistry*, 67(1):15-22 (2005)) and in carbon/polymer based materials (Christwardana, et al., *Scientific Reports*, 6:30128 (2016)).

Figure 4A:
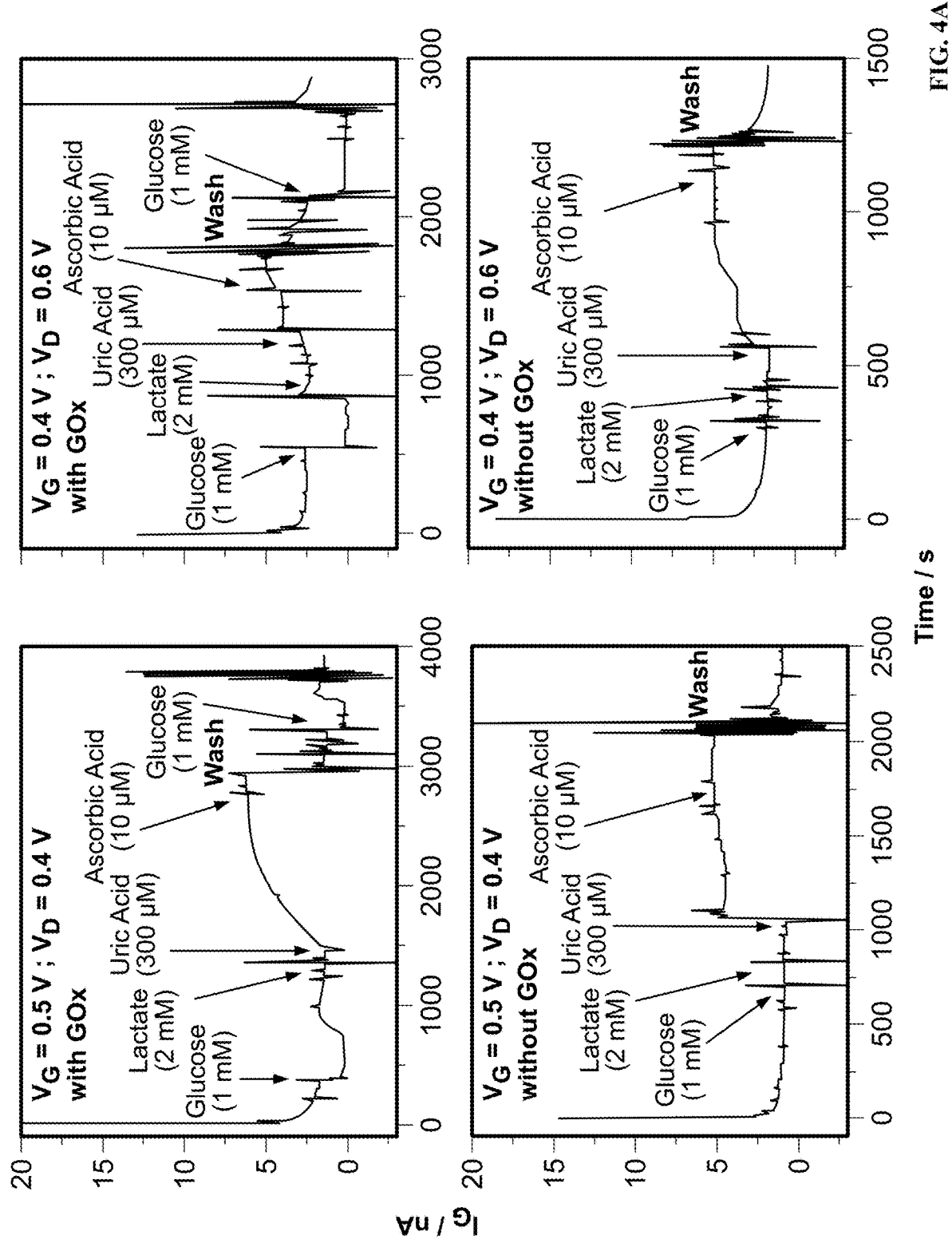
FIGS. 4A and 4B are graphs showing the selectivity of the device. The selective response of the sensor is tested against the analyte of choice (Glucose) and against the most common interferences found in biological fluids at relevant concentration.

Example 3. The n-Type OECT Demonstrates Excellent Selectivity to Glucose in the Presence of Glucose Oxidase Materials and Methods The selectivity measurements have been performed for two combination of $V_D$ and $V_G$ and the corresponding gate currents for each measurements are plotted in FIG. 4A.

Results

In electrochemical based detection, selectivity of the biosensor to the analyte of choice is paramount as other electrochemically active compounds, known as interferences in complex media, can give rise to false positive signals. The n-type OECT sensor exhibits excellent selectivity to glucose in the presence of GOx as verified from FIG. 4B, which shows the normalized response of the transistor to glucose in the presence of various interferences at relevant physiological concentration (lactate, uric acid and ascorbic acid) with and without GOx in buffer solution (PBS). In the absence of the GOx enzyme (FIG. 4), the device is not sensitive to glucose and lactate. Nonetheless, a somewhat relevant sensitivity is evidenced to uric and ascorbic acids, attributed to the change in the pH of the solution (pH<6), which does not impede the sensing performances (Pappa, et al., *Science Advances*, 4(6):eaat0911 (2018)). Upon introducing GOx, the device shows strong sensitivity to glucose as the channel current increases with glucose (in the expense of the gate current, FIG. 4A). Yet, the device still seems to be equally sensitive to the uric and ascorbic acids. Previous studies suggested that for this type of sensors, even at very low gate voltages (i.e to avoid electro-oxidation of interferents), there is always a contributing signal stemming from interferents and drifts of the baseline (Pappa, et al., *Advanced Healthcare Materials*, 5(17):2295-2302 (2016)). The latter issue can be easily addressed via background subtraction owing to circuit engineering (Braendlein, et at, *Advanced Materials*, 29(13): 1605744 (2017)).

Example 4. The n-Type OECT Demonstrates Enhanced Operational Stability and a Shelf Life of Over 6 Months Materials and Methods The device's operational stability has been tested under successive gate voltage pulses (5s pulse) for over 2h of operation with different $V_D/V_G$ combination effects.

Results

Figure 4B:
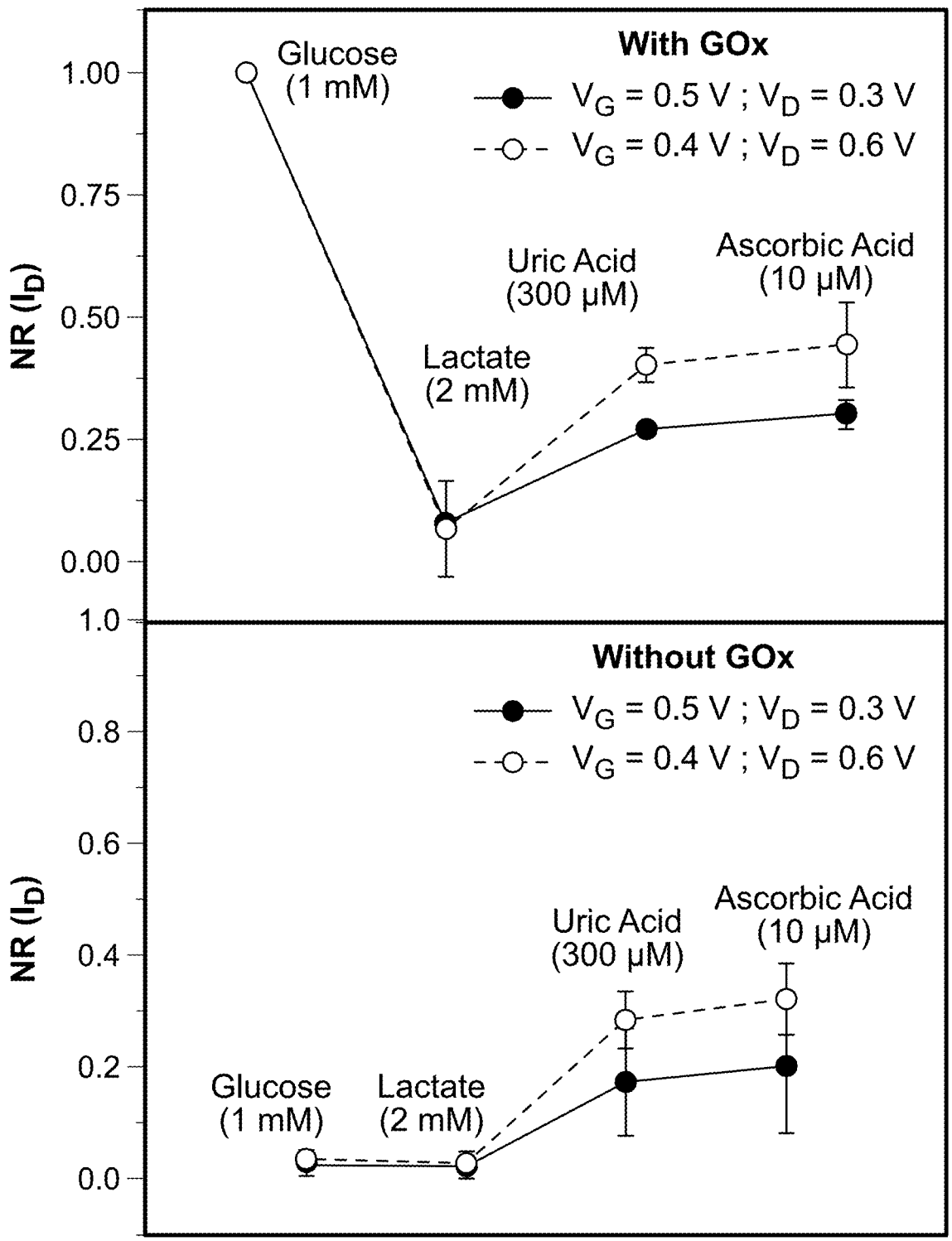
Figure 5:
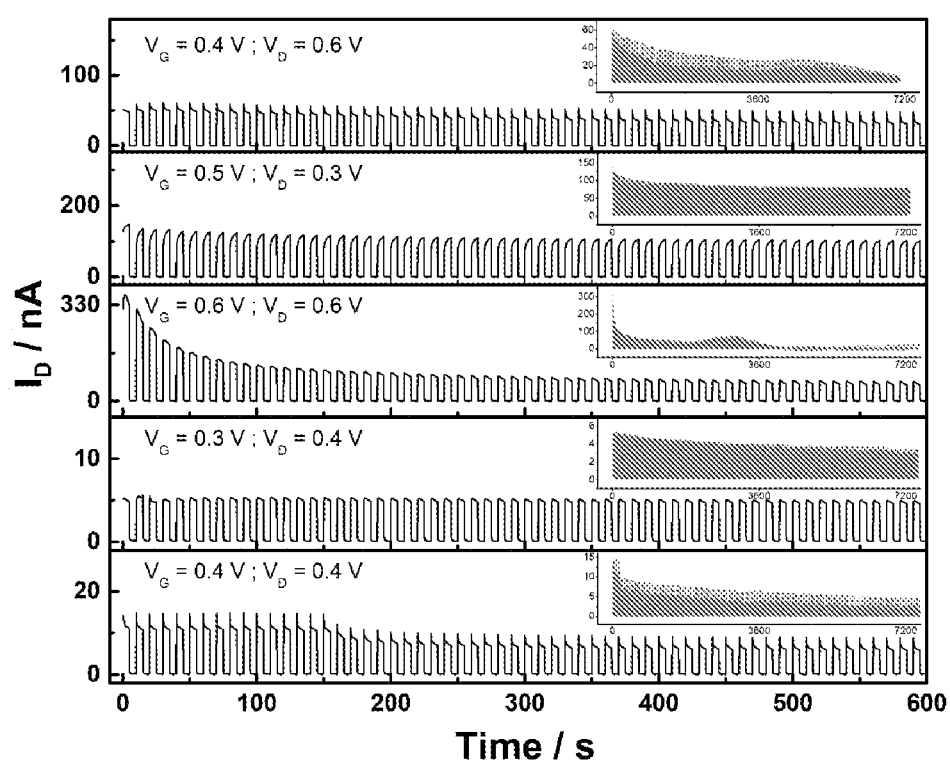
FIG. 5 shows graphs of drain current versus time to demonstrate long term stability of the transistor in PBS. The drain current versus time is plotted under different biasing conditions during the first 10 min of operation. Inset shows the stability over 2 hours of operation. A gate voltage pulse was applied for 5 s with an interval time of 5 s between the successive pulses while a drain voltage is continuously applied.

The sensitivity to interference is strongly linked with the bias conditions applied (FIG. 4B). Giving the importance of the bias applied on sensor sensitivity and selectivity, it is crucial to evaluate its effect on the device stability. The latter is highly dependent on the magnitude of the bias applied. FIG. 5 shows the device operational stability under successive gate voltage pulses (5s pulse) for over 2h of operation with different $V_D/V_G$ combination effects. For the same $V_D$ (0.4 or 0.6V), a more positive $V_G$ leads to a higher transconductance operational regime of the device but results as well in a more pronounced device degradation (Pappa, et al., *Science Advances*, 4(6):eaat0911 (2018)). The drain voltage value exerts more influence on device stability while high $V_G$ (0.5 V) and low $V_D$ (0.3 V) values yield the most stable conditions. It is important here to note that all conditions reveal an initial degradation from which the amplitude is found to be dependent on bias combination. In biosensing nonetheless, the sensor is operated at constant gate voltages, so the material does not suffer from continuous doping and dedoping cycles as in the case of this experiment where the conditions are more stressful to the material. The device showed remarkable recovery from this "pulsed gating stress" over time; it could be used for subsequent biosensing experiments with an efficiency similar to that of the fresh device (same dynamic range—100 nM to 20 mM—and sensitivity—portrayed from the error bars (±10%)). The same sensor can be used for multiple times over 6 months with no noticeable effect of degradation. Because of the simple design of the biosensor and the properties of the devised active material, no bio-functionalization is necessary whilst the enzyme can be washed away via incubation in water and fresh enzyme can be adsorbed for new measurements. This memory behavior is very intriguing.

Overall, a diligent choice of the bias applied not only allows to tune the sensitivity of the device but also enhances the control of the devices operational stability. The device exhibits a wide dynamic range with the ability to tune its sensitivity according to the analyte range of choice (blood, saliva, sweat, and tears), good selectivity and operational stability and importantly a shelf life of over 6 months.

Example 5. The n-Type Polymer Allows Direct Electrochemical Communication Between the Enzyme and the Polymer Film Materials and Methods.

GOx was drop-casted on the surface of the device for 30 minutes, followed by tedious rinsing with deionized water and drying with nitrogen gas. The extra rinsing step implemented here reassures the removal of non-adsorbed enzyme. Fresh buffer solution, without enzyme, was then introduced on the device as electrolyte and bias was applied to the OECT. The drain current was monitored over time as progressively glucose aliquots were added in the solution. In order to validate the direct electron transfer mechanism, the gate was disconnected and the device was placed in a resistor configuration. GOx and the analyte (1 mM glucose) were added sequentially and the drain current was monitored over time.

Results

Figure 6A:
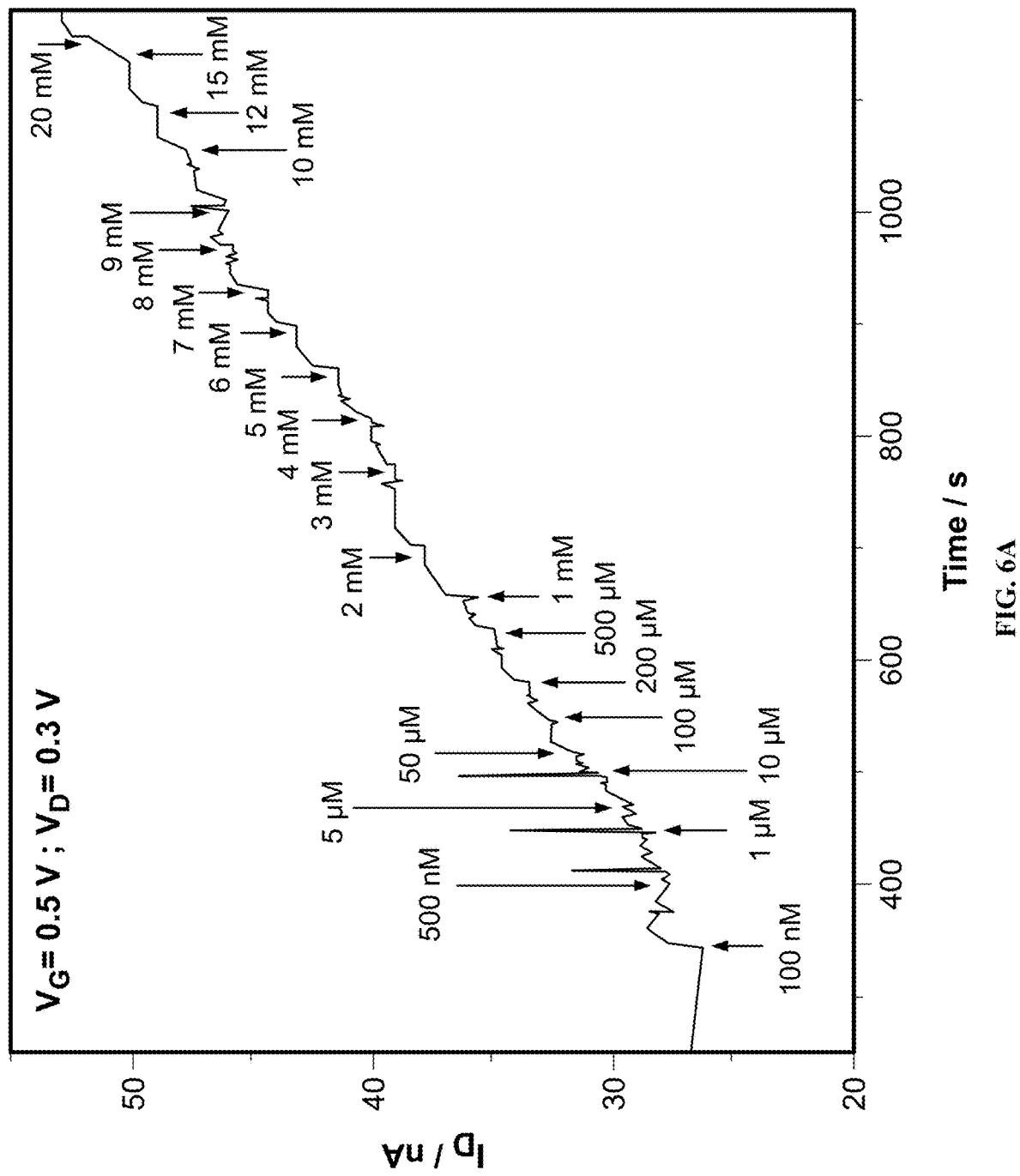
FIGS. 6A and 6B show graphs of real-time response of the OECT upon consecutive addition of glucose to the buffer solution (PBS) (FIG. 6A) and the corresponding normalized calibration curves when the enzyme is rinsed off the surface (red) and not rinsed off the surface (black) (FIG. 6B). Calibration plots for different biasing conditions (gate or channel driven reaction) are displayed. The enzyme GOx was drop casted on the device, left to adsorb for 30 min and followed by extensive rinsing with deionized water. Fresh buffer solution was added bias was applied.
Figure 6B:
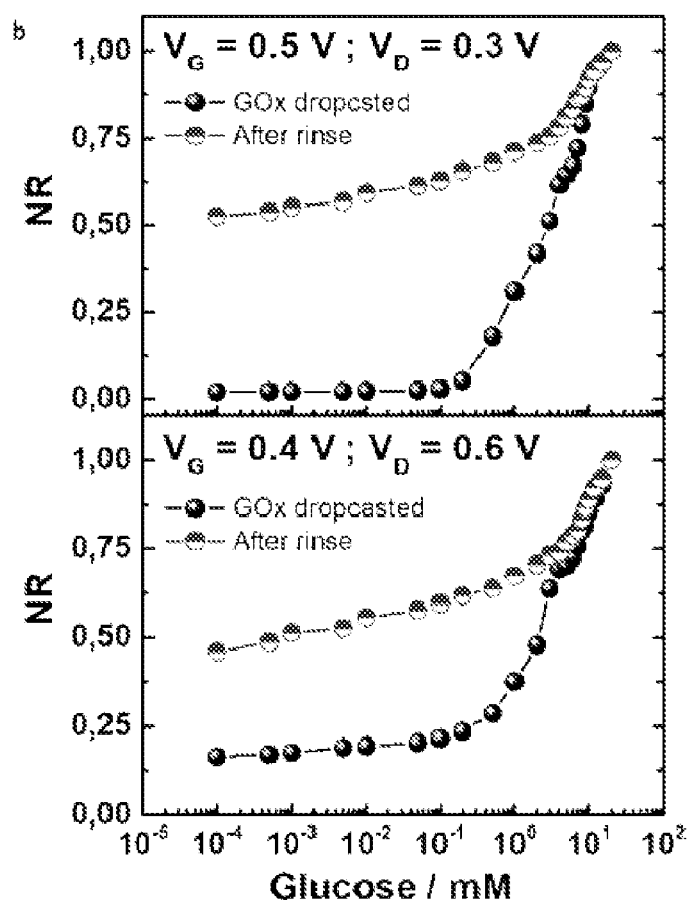

The direct electrochemical communication between enzymes and the polymer film is attributed to the presence of ethylene glycol groups from the copolymer side-chains. The direct electron transfer mechanism as well as the vital role of polar glycol groups in the enzyme stabilization on the surface were demonstrated. FIGS. 6A and 6B show the real-time response along with the normalized glucose titration curve. Initial results revealed that the device was sensitive to the same dynamic range (100 nM to 20 mM), as in FIG. 2, highlighting the successful immobilization of the enzyme. In the comparative glucose titration curves of FIG. 6B under the same biasing conditions, the device "rinsed" and the one "non-rinsed" display similar sensitivity (i.e slope) over the same range of analyte. The higher current values for low analyte concentrations of the "rinsed" device stem from the normalization method followed here (normalized to the maximum sensing current) so as to accurately compare the tested devices. When the surface of the OECT is rinsed and enzymes are somewhat removed, the maximum current obtained with analyte saturation is lower than when the device is non-rinsed. The active sites on the substrate upon rinsing are not efficiently replenished leading to lower currents. The $K_M^{app}$ was found marginally smaller value ($K_M^{app}$=2.68 μM) when compared with previous calculations.

Figure 7:
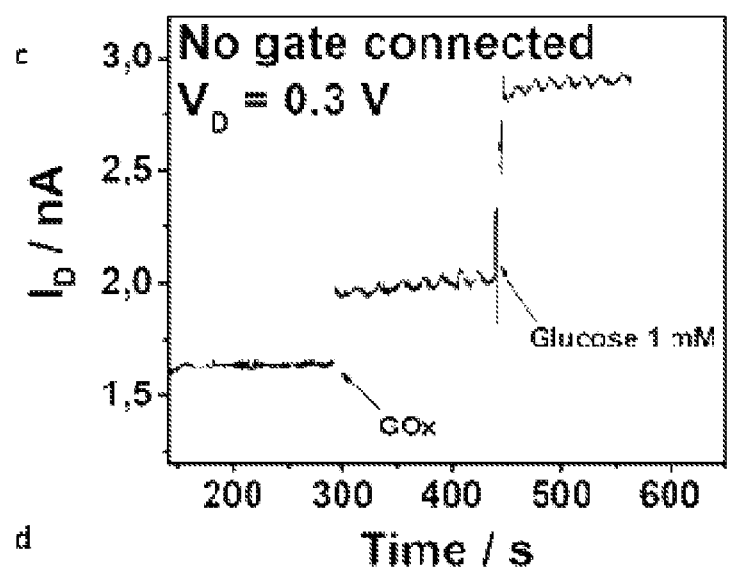
FIG. 7 is a graph showing the doping effect of GOx and glucose oxidation by the enzyme on P90. The gate was disconnected and only a drain bias was applied.

In order to validate the direct electron transfer mechanism, the gate was disconnected and the device was placed in a resistor configuration. GOx and the analyte (1 mM glucose) were added sequentially and the drain current was monitored over time (FIG. 7). FIG. 7 demonstrates that the addition of both enzyme and subsequent analyte increases the drain current of the transistor channel, thus making it more conductive as additional electrons are injected into the channel. When doing so with the lactate as analyte, the change in current of the OECT was near the noise level. This is likely caused by the deeper active site of the LOx compared to the GOx's one (8.7 Å) (Madou, *Solid-State Physics, Fluidics, and Analytical Techniques, in Micro- and Nanotechnology*, Taylor & Francis (2011)), making the direct electron transfer more difficult in the case of former. By comparing the amplitude of the response at 1 mM of glucose with or without the gate of the OECT connected, the amplification properties of the OECT (gate connected) compared to a conventional amperometric sensor (gate disconnected) are highlighted. Further, the addition of GOx leads to the doping of the polymer as the current increases from 1.6 nA to 2 nA, validating the direct electron transfer between the P90 and the FAD center of the GOx. Doping by GOx incorporation into polymer structures has been previously reported (Thompson, et al., *Macromolecular Rapid Communications*, 31(14):1293-1297 (2010)). According to Thompson et al., the structural change of PEDOT was devised via vapor phase polymerization through introducing GOx into the structure.

Example 6. The n-Type Polymer Structure Promotes the Entrapment and Stability of the Enzymes on the Polymer Surface Materials and Methods The role of polar glycol groups on the enzyme adsorption on the polymer was investigated through QCM measurements in similar manner to previously attempts (Pappa, et al., *Science Advances*, 4(6):eaat0911 (2018)). The adhesion of GOx on two different copolymers sharing the same NDI-T2 backbone but a different ratio of alkyl/glycol side chains, 100/0 (P0) and 10/90 (P90) respectively. The effective physical entrapment of the GOx enzyme on the P90 film using quartz microbalance with dissipation monitoring (QCM-D) was determined. QCM-D has been used in numerous applications owing to its ability to monitor surface interactions (Savva, et al., *Journal of Materials Chemistry C*, epub online Jul. 11, 2018; Jensen, et al., *Langmuir*, 28(30):11106-11114 (2012)). QCM-D measurements were conducted using a Q-sense analyzer (QE401) on bare Au sensor (as reference) and then on the Au sensor coated with the film.

Results

Figure 24:
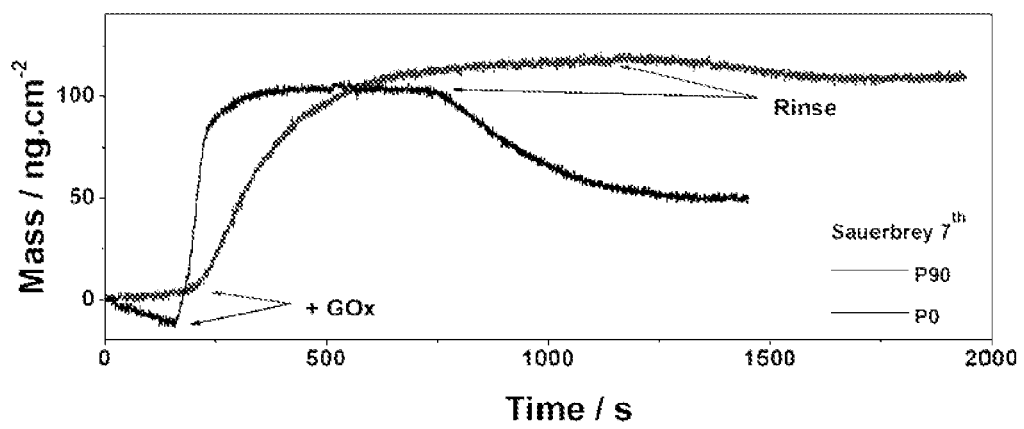
FIG. 24 shows graphs of QCM-D measurements ($7^{th}$ overtone) showing the interactions between the enzyme and two polymer films characterized by their glycol content (P90=90% glycol and P0=0% glycol) in two stages: (1) when the GOx enzyme is injected into the PBS solution (+GOx), and (2) when the enzyme-exposed film is rinsed with PBS (Rinse). The mass of the film was calculated using a Sauerbrey equation (3).

The evidenced strong adsorption of enzymes lies in the presence of ethylene glycol side chains that promote the adhesion of proteins on the surface of the polymer. The ethylene glycol side chains are distributed on the surface of the electrode as demonstrated by monitoring lipids bilayer formation (Inal, et al., *ACS Applied Bio Materials*, 1(5): 1348-1354 (2018)). The adhesion of GOx on two different polymers with different glycol fraction, a P90 film (90% glycol) and a P0 film (0% glycol) was compared. The QCM-D modelling of the mass added on the polymer film (using the $7^{th}$ overtone) for the two different surfaces was done using the Sauerbrey equation:

$$\Delta m = \frac{-17.7}{n * \Delta f} \qquad (3)$$

where n is the number of the selected overtone for the quantification of the mass and −17.7 is a constant determined on the resonant frequency, active area, density and shear modulus of the piezoelectrically active quartz crystal (Savva, et al., *Journal of Materials Chemistry C*, epub online Jul. 11, 2018). Based on a previous reported study of the NDI-T2 polymer series with various ethylene glycol fractions and the appropriate fitting of our measurements, modelling the experiment through the Sauerbrey equation is valid (Inal, et al., *Journal of Polymer Science Part B: Polymer Physics*, 54(2):147-151 (2016)). After stabilizing the film in buffer solution (PBS), a GOx solution (10 mg·mL$^{-1}$) is introduced in the chamber. The film is stabilized and pure buffer is purged in the chamber to allow loosely bound proteins to desorb. As the enzyme solution is flowing on the sensor surface, a similar amount is observed to get adsorbed on the surface of the two polymers under constant flow (ca. 100 ng and 118 ng·cm$^{-2}$ for P0 and P90 respectively). Upon rinsing the sensor with PBS, a 50% decrease of the adsorbed enzyme amount on the P0 surface was found, compared to the mere 7% for the case of the P90 film (FIG. 24). The results stemmed from the QCM-D demonstrate that the ethylene glycol side chains in the polymer structure play a key role in promoting the entrapment of the enzyme and enzyme stabilization on the polymer surface.

Overall, the n-type OECT device in an accumulation mode allows for complex biofunctionalization-free, mediator-free, and reference electrode-free direct glucose detection. The device detection is based on direct electron transfer between the enzyme and the polymer and exhibits a wide dynamic range (100 nM to 20 mM, spanning through the physiologically relevant concentration ranges of glucose in biological fluids), excellent selectivity and selectivity, improved operational stability and a shelf life of over 6 months. It is confirmed that the polymer structure plays an important role in the adsorption of the enzyme through the presence of ethylene glycol side-chains. Further, by tuning the device operation parameters, it is possible to control the sensitivity and dynamic range of the device according to the biological fluid of interest (blood, saliva, sweat).

Example 7. N-Type OECT Allows for Direct Detection of Lactose

Materials and Methods

For the device fabrication, the Au contacts (located at the source, drain, and gate) and interconnects were patterned on a glass substrate, and an additional layer of Parylene C was used to insulate the Au interconnects according to established protocol (Nielsen, et al., *Journal of the American Chemical Society*, 138:10252-10259 (2016)). The final channel dimension is 10 mm in length and 100 mm in width, while the gate electrode has an active area of 500 mm$^2$. The active material, P-90, was spin-cast directly from a solution (1000 rpm, 30 s) without any annealing or post processing steps. The polymer P-90 was synthesized according to the literature (Giovannitti, et al., *Chem. Mater.*, 30:2945-2953 (2018)).

For the sensing experiments, lactate oxidase (Lox) in PBS (10 mg ml$^{-1}$) was drop-casted on the device active area (channel and gate). The schematics describing this functionalization step can be found in FIG. 8. Lactate was dissolved as stock solutions in PBS. Current-voltage characteristics of the deviceswere recorded using a Keithley 2612A dual SourceMeter. The readout signal of the OECT at zero analyte concentration was the steady-state current obtained in PBS solution. After a steady baseline was obtained for the drain current, changes in response to subsequent additions of increasing concentrations of lactate solutions into the electrolyte were monitored as a function of time. For all the experiments, the volume of the solution was kept fixed at 50 mL. The response of the device to lactate was normalized to allow for an accurate comparison between different devices. The NR was determined by formula (1) as described above, which considers the current output after it reaches a steady-state value according to formula (1).

Results

The n-type-conjugated polymer that was chosen as the active material is P90 (Chen, et al., *Journal of the American Chemical Society*, 131:8-9 (2009)), which has a backbone comprising a highly electron-deficient naphthalene-1,4,5,8-tetracarboxylic diimide (NDI) repeat unit and an electron rich unsubstituted bithiophene repeat unit (T2) (FIG. 1A). The side chains on the diimide unit were a 90:10 randomly distributed ratio of polar glycol and nonpolar branched alkyl groups, where the ratio was optimized to ensure solubility of the copolymer in polar solvents (Giovannitti, et al., *Chem. Mater.*, 30:2945-2953 (2018)). The glycol side chains are envisaged to serve the dual role of (i) providing polar groups for the enzyme to interact with (Al-Ani, et al., *Polymers*, 9:343 (2017)) and (ii) enhancing the polymer's water uptake capacity (Yang, et al., *J. Polym. Sci. B Polym. Phys.*, 43:1455-1464 (2005)), known to promote electrochemical activity in aqueous media (Giovannitti, et al., *Proc. Natl. Acad. Sci. U.S.A.*, 113:12017-12022 (2016)).

The copolymer P90 based OECT coupled with lactate oxidase (LOx) is schematically depicted in FIG. 8. An all-planar configuration is adopted, where the polymer is used in the channel and at the gate electrode. Note that the film surface is not chemically treated to immobilize the enzyme (the enzyme solution was simply placed on the active area), neither is an ET mediator incorporated into this device. As such, the device not only is compatible with large area processes such as printing but also provides ease of integration with microfluidics or adaptation for use in in vivo environments (Khodagholy, et al., *Nature Communications*, 4:1575 (2013)). These accumulation mode OECTs exhibit a high signal on/off response (translating into high gain) and a low-power operation in common aqueous electrolytes (Nielsen, et al., *Journal of the American Chemical Society*, 138:10252-10259 (2016)). The current-voltage characteristics show a monotonic increase of the source-drain current ($I_D$) with increasing gate voltage ($V_G$) due to doping of the film by the cations injected from the phosphate-buffered saline (PBS), a buffer that mimics the pH, osmolarity, and ion concentration in the human body (FIGS. 9A and 9B). The first derivative of this curve, that is, the output ($I_D$) of the device versus the input ($V_G$), expresses the signal amplification by the OECT, namely, the transconductance. The transconductance curve follows a monotonic trend as well: the efficiency of transduction scales with $V_G$ (FIG. 9B). Giovannitti and co-workers (Giovannitti, et al., *Nature Communications*, 7:13066 (2016)) recently showed that the polar glycol side chains attached to such hydrophobic polymer backbones enabled reversible electrochemical switching between the reduced (n-type-doped), oxidized (p-type-doped), and neutral state of the film in similar aqueous electrolytes. During the reduction process (triggered by a positive gate bias), cations drift into the film to counterbalance the electrons stabilized on the backbone of the copolymer.

Figure 8B:
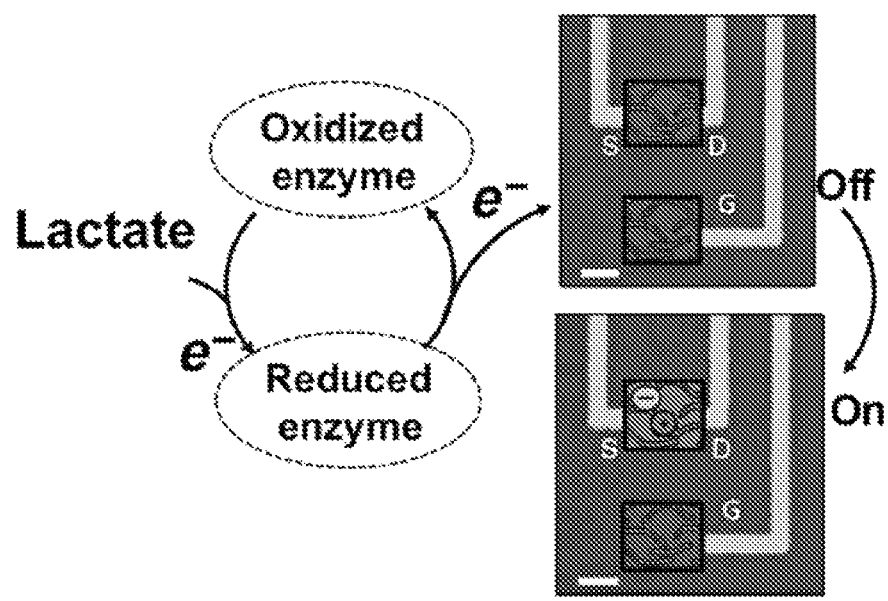
Figure 9A:
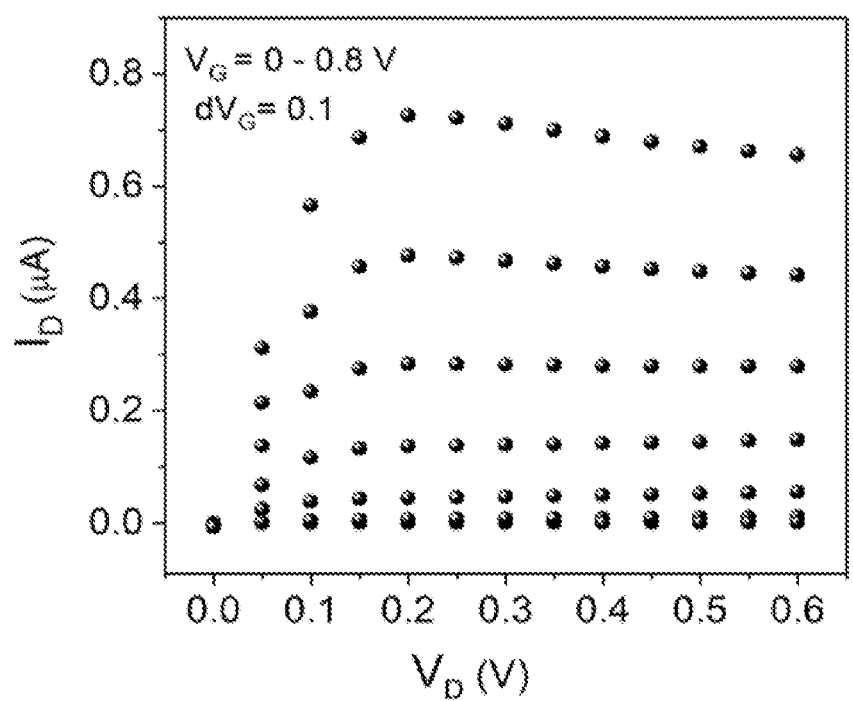
FIGS. 9A and 9B are graphs showing the output and transfer characteristics of a typical all n-type polymer (P90) based OECT (FIG. 9A) and the corresponding transconductance values (gm) along with the transfer curve ($V_D=0.5$ V) (FIG. 9B). The channel has a thickness, width, and length of ca. 100 nm, 100 $\mu m$, and 10 $\mu m$, respectively. The electrolyte is PBS.
Figure 9B:
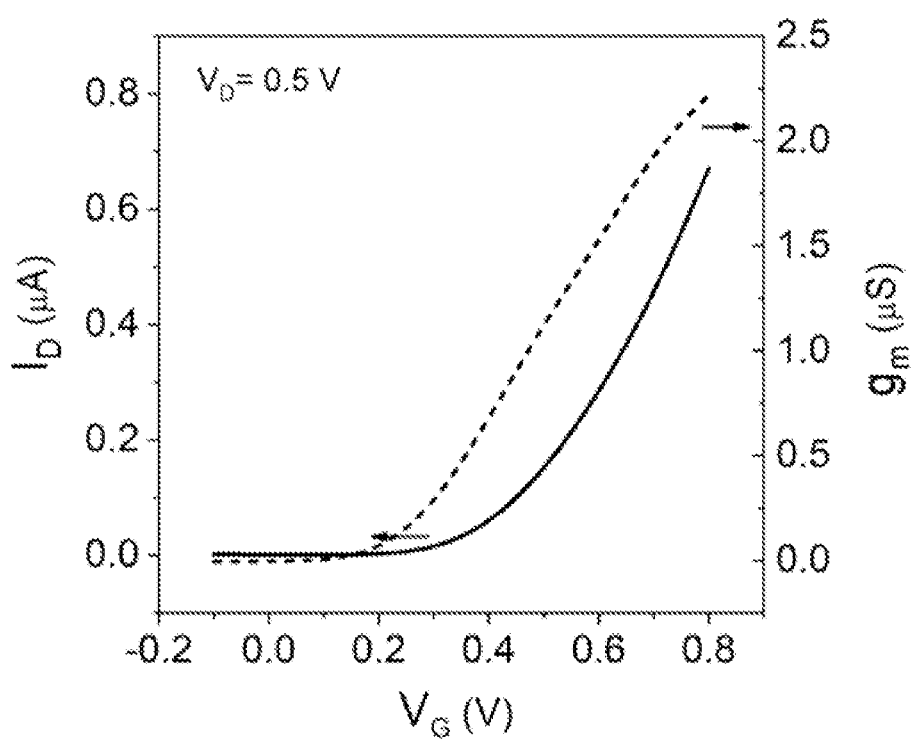
Figure 10:
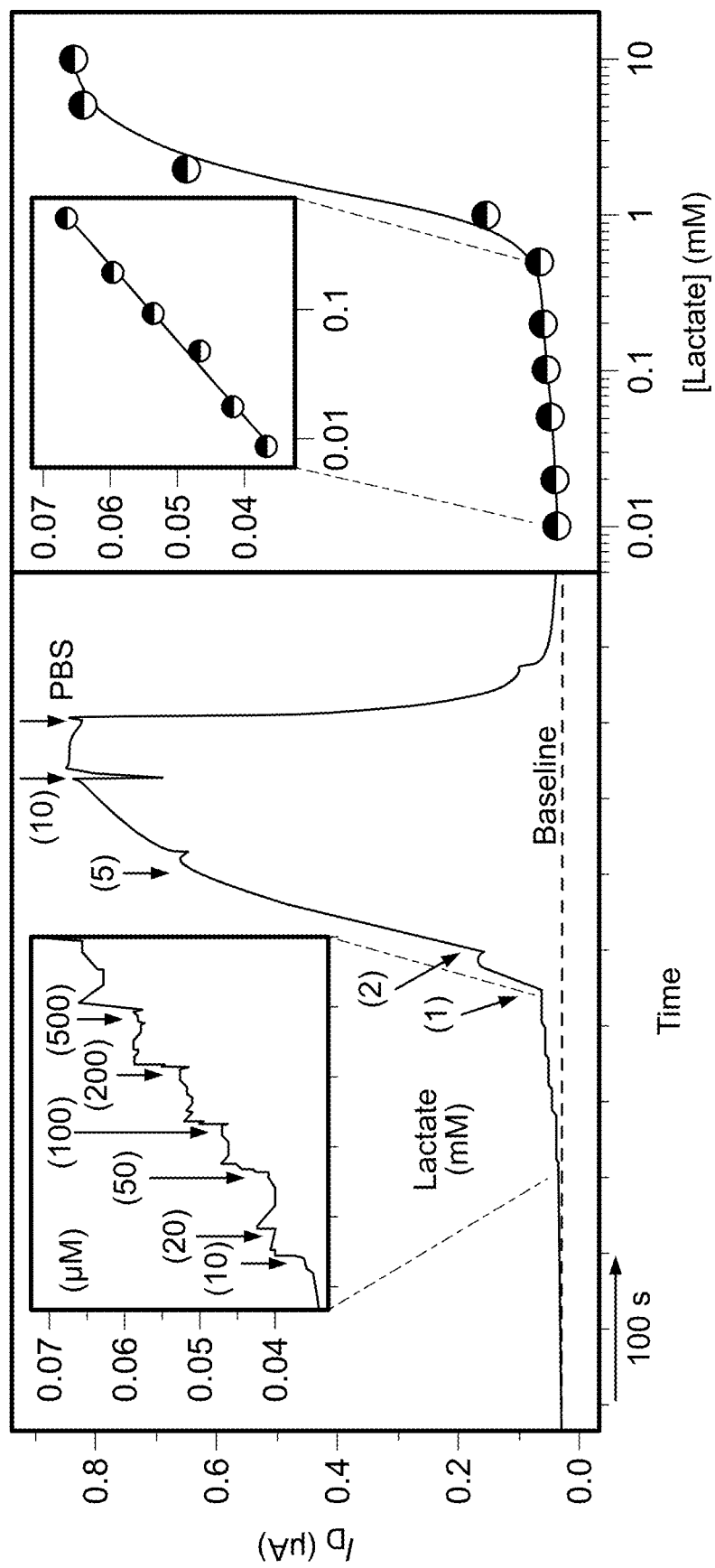
FIG. 10 show graphs of real-time response of the OECT (source-drain current, ID, as a function of time) as successive amounts of lactate are added to the PBS solution containing the enzyme, LOx, and the corresponding calibration curve in semilogarithmic scale. Arrows indicate the addition of lactate. After 10 mM lactate, the device is washed with PBS, and the output signal decreases back to its initial value. The insets represent the magnified response of the transistor to low amounts of the analyte (10 to 500 mM).
Figure 11:
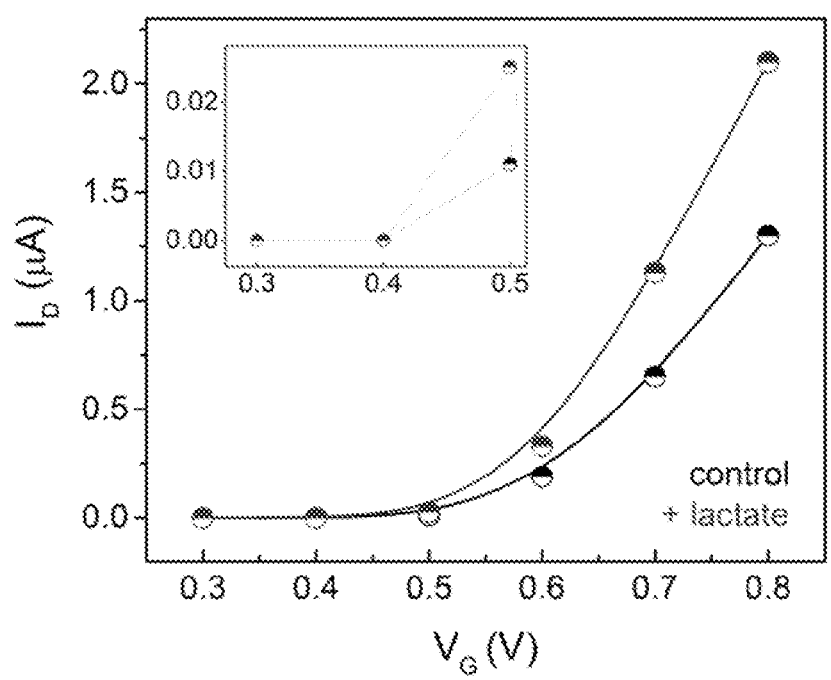
FIG. 11 shows curves of transfer curves of the OECT in the absence and presence of the enzymatic reaction. The curves show the increase in $I_D$ as a function of $V_G$ ($V_D=0.5$ V) in the presence (red line) and absence (black line) of lactate in the solution containing Lox. The onset $V_G$ that needs to be applied for sensing lactate corresponds to the actual onset voltage of the device. The inset show the magnified response of the device at low $V_G$.

As P90 has the ability to stabilize electrons on its backbone, those generated during an enzymatic reaction could be directly transferred to the channel, increasing its conductivity (Liang, et al., *Journal of the American Chemical Society*, 137:4956-4959 (2015)), thereby turning the device on (FIG. 8B). FIG. 10 shows the chronoamperometric response of the OECT, that is, the change in the saturation current that flows through the P90 channel, to the real-time additions of cumulative concentrations of lactate in the presence of LOx in PBS. The $I_D$ increases with increasing concentrations of lactate, suggesting a reaction-triggered gating of the channel. The specific and reversible reaction of LOx with lactate affects the conductance of the channel. It is noted that the device is responsive to lactate only when it is operated at gate voltages equal to or higher than the threshold voltage (that is, the minimum $V_G$ required to turn the device on) (FIG. 11). The dose-dependent effect of lactate on the steady-state characteristics of the OECT, for a remarkably wide range of concentrations, outperforms PEDOT:PSS-based OECTs of comparable geometry used as lactate sensors, despite the absence of an electron mediator (Pappa, et al., *Advanced Healthcare Materials*, 5(17):2295-2302 (2016)).

Figure 12A:
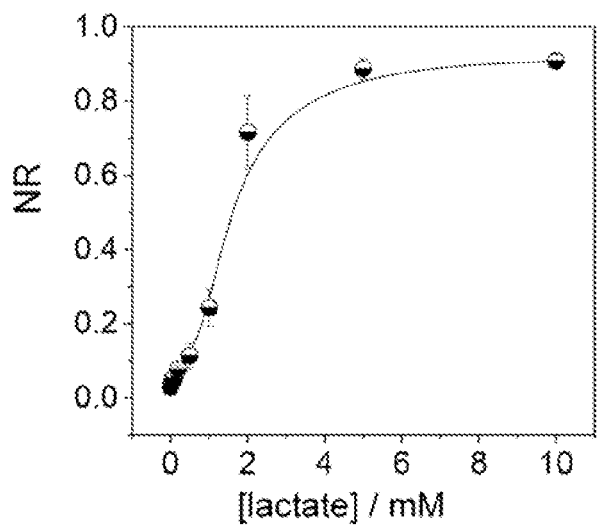
FIGS. 12A-12C show calibration curves relating the NR of the device to a range of lactate concentrations.
Figure 12B:
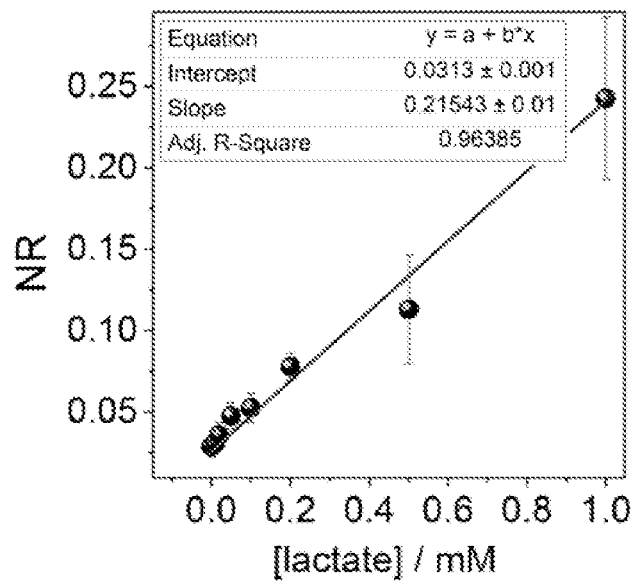
Figure 12C:
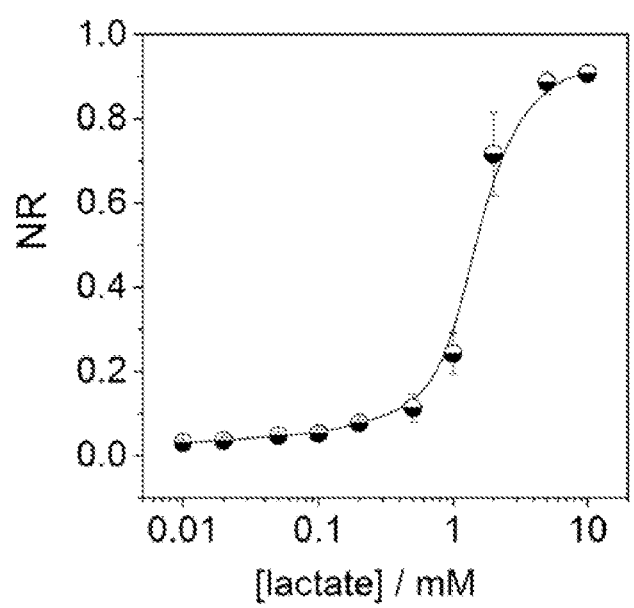

This platform yields excellent biosensor analytical characteristics as evidenced from the normalized lactate titration curves (FIGS. 12A-12C). When operated in the bespoke parameters (that is, $V_D$=0.7 V and $V_G$=0.5 V), the channel with this particular geometry responds to micromolar concentrations of lactate with a linear relationship up to 1 mM and a wide dynamic range of detection from 10 µM to 10 mM. The change in the $I_D$ occurs rapidly (within ca. 2 s), particularly for low metabolite concentrations (<0.3 mM) (FIG. 10). Notably, the device response is reversible; for example, when the 10 mM lactate solution on top of the device is replaced with PBS (washing step), the current reverts to its initial, lactate-free value. The device response to lactate is reproducible with no significant device-to-device and measurement-to-measurement variations, especially for the detection of low lactate concentrations (mean calculated error, 2.4%; FIGS. 12A-12C).

The observed deviation in the sensor performance among different devices is mostly attributed to the thickness variations of the film in the channel, which affect the gain of the OECT. It is believed that control over film thickness can be easily addressed by adjusting the fabrication procedure as showed in previous study (Braendlein, et al., *Advanced Materials*, 29(13):1605744 (2017)). Furthermore, the error arising from multiple measurements on the same device can be reduced by introducing a more controlled environment for the addition of lactate. For example, the volume of the liquid that the device is exposed to could be controlled precisely by integration of microfluidics, which would mitigate user error.

Example 8. The n-Type OECT Allows for Efficient Electron Transfer from the Enzyme to the Polymer Materials and Methods All characterization was performed in PBS. The cyclic voltammograms were recorded using a potentiostat-galvanostat (PGSTAT128N, Autolab) with an Ag/AgCl reference electrode and a Pt counter electrode. The working electrode was P-90 cast on a Au-coated glass substrate. The system, in a closed chamber, was systematically degassed for at least 15 min in N2 before performing any measurements for characterization under inert atmosphere. The topography and the roughness of the polymer film and the enzyme adsorption were investigated using AFM and QCM-D. AFM measurements were performed in tapping contact mode with an Agilent 5500 SPM AFM in both air and liquid. QCM-D measurements were conducted using a Q-sense analyzer (QE401) on a bare Au sensor (as reference) and then on the Au sensor coated with the film. The data were treated with a viscoelastic model to calculate the mass of the enzyme adsorbed on the film (ElMahmoudy, et al., *Macromol. Mater. Eng.*, 302:1600497 (2017)). UV-vis-NIR spectra were recorded using an Ocean Optics QE Pro Scientific grade spectrometer (185 to 1050 nm). For spectroelectrochemistry measurements, the spectrometer was coupled to a Keithley 2606A source measure unit, and when required, bias was applied between the polymer-coated ITO substrate, which serves as the working electrode and a Ag/AgCl reference electrode.

Results

Figure 13A:
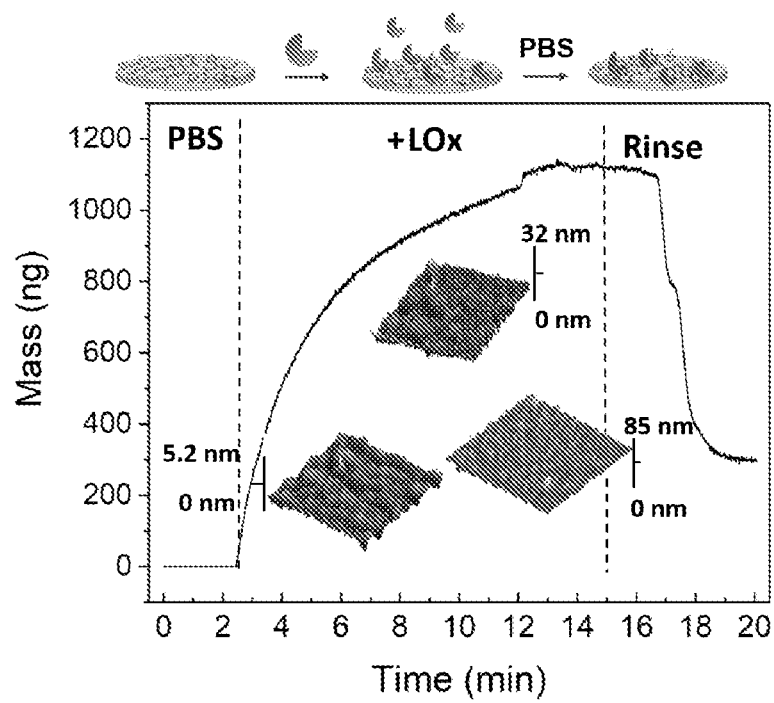
FIGS. 13A and 13B are graphs of QCM-D measurements showing the interactions between the enzyme and the polymer film in three stages: when the film is exposed to the electrolyte (PBS), when the enzyme is injected into the PBS solution (+LOx), and when the enzyme-exposed film is rinsed with PBS (Rinse). The mass of the film was calculated using a viscoelastic model (FIG. 13A). Three dimensional AFM images (2×2 mm$^2$) show the changes on the surface of the film during the three stages.
Figure 13B:
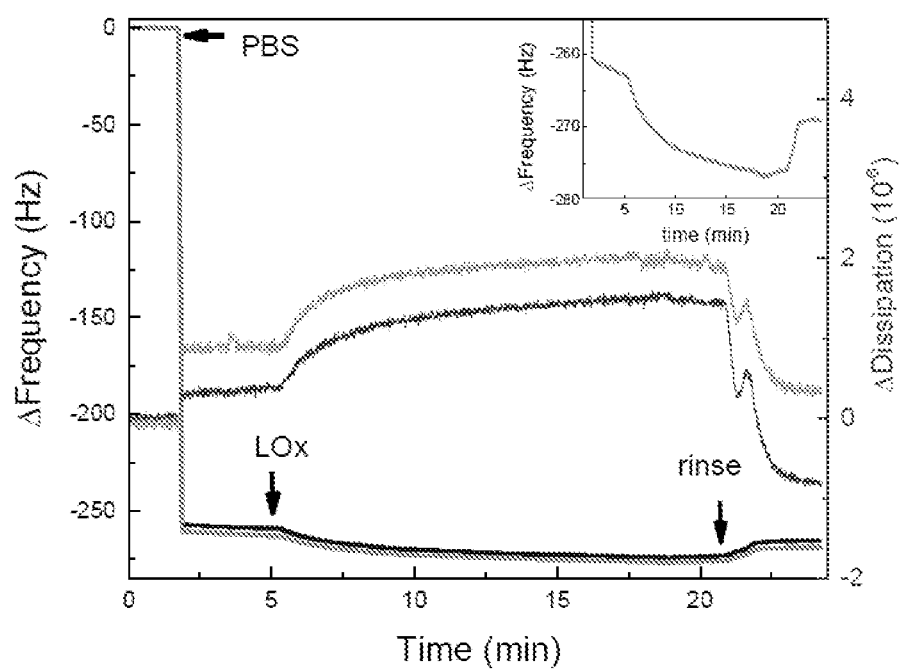

To elucidate the mechanism behind the gradual increase in the channel current as lactate is oxidized by LOx in the electrolyte, the interactions between the enzyme and the film is studied, which leads to such an efficient electrochemical communication. Quartz crystal microbalance with dissipation monitoring (QCM-D) measurements are used because of the versatility of the tool in monitoring interactions of a solid surface with certain species in a solution (Pappa, et al., *ACS Appl. Mater. Interfaces*, 9:10427-10434 (2017)). FIG. 13A shows the enzyme-induced changes in the oscillation frequency of the QCM crystal coated with the copolymer P90 that are translated into the variations in the mass of the film (see FIG. 13B for the raw QCM-D data, that is, frequency change versus time plots). As LOx is introduced into the PBS solution that is flowing over the film, the mass on the sensor increases (FIG. 13A, the region marked as "+LOx"). Distinct changes are also monitored in the surface topography of the polymer film in the presence of the enzyme. Even after rinsing this film with PBS, we find that a high amount of the enzyme remains on the polymer surface (FIG. 13A, the region marked as "Rinse"). At this stage, the film surface is also rougher compared to its pristine state, which further substantiates the localization of the protein on the surface.

Figure 14A:
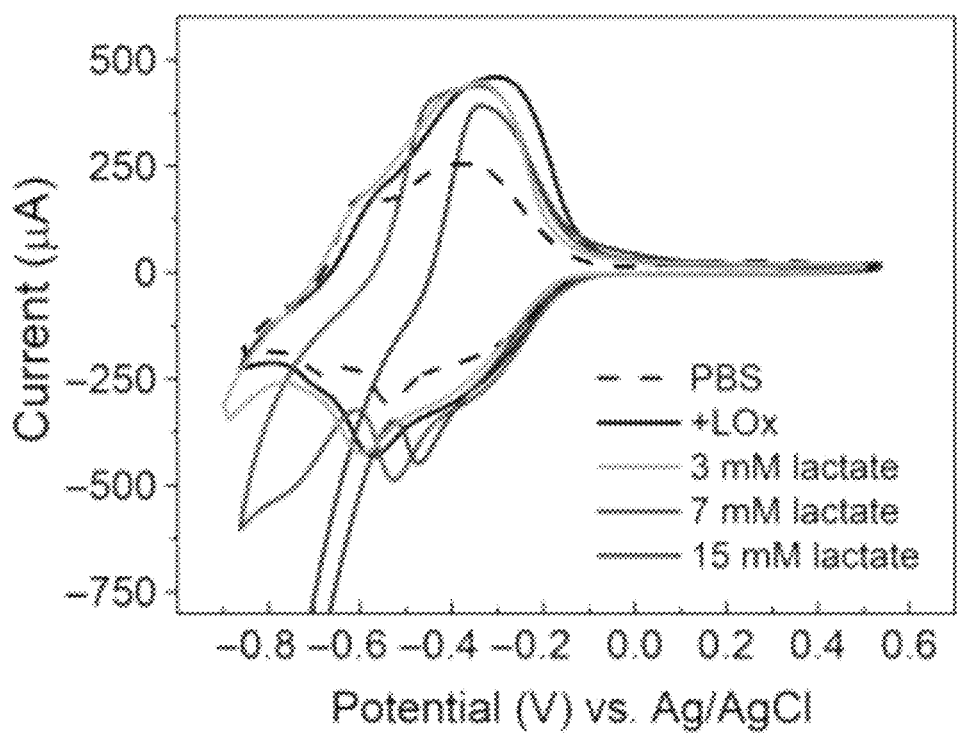
FIGS. 14A and 14B show cyclic voltammogram (CV) curves of the P90 film cast on gold (Au)-coated glass substrate recorded in PBS (dashed black lines) and with LOx (black solid lines). The spectrum changes further upon addition of increasing concentrations of lactate into the solution because of the reaction with Lox (FIG. 14A). The CV curves of FIG. 14B show the peak positions of the two prominent redox couples (Red/Ox 1 and Red/Ox 2) of the material (dashed lines). Enzyme addition causes a change in the shape of the curve (solid lines). The scan rate is 50 mV s$^{-1}$ and the scanning bias is in the backward direction.
Figure 14B:
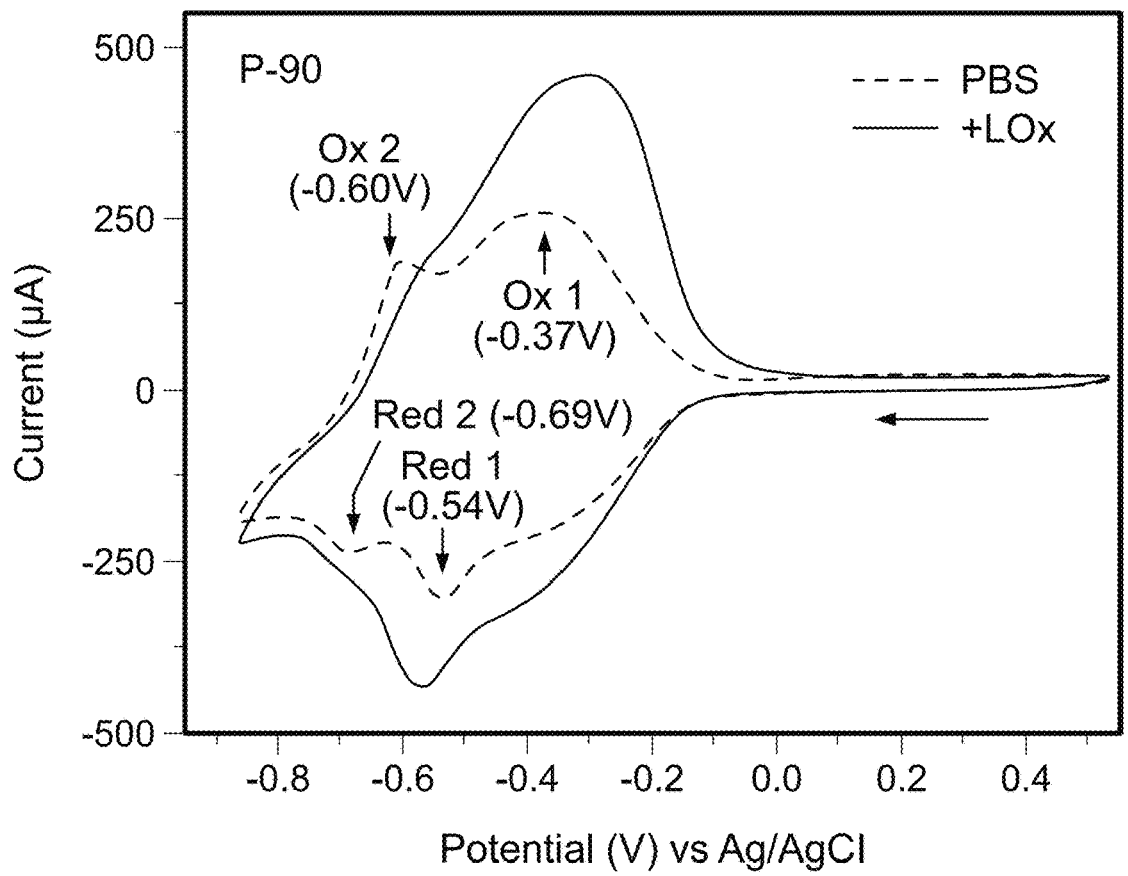
Figure 15:
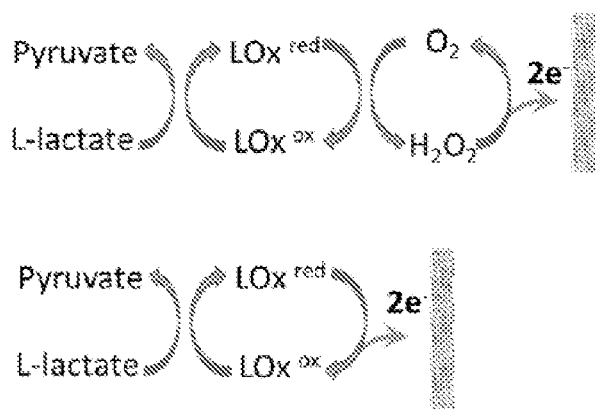
FIG. 15 shows the reaction cycles in the presence and absence of $O_2$, with the associated redox reactions.
Figure 16A:
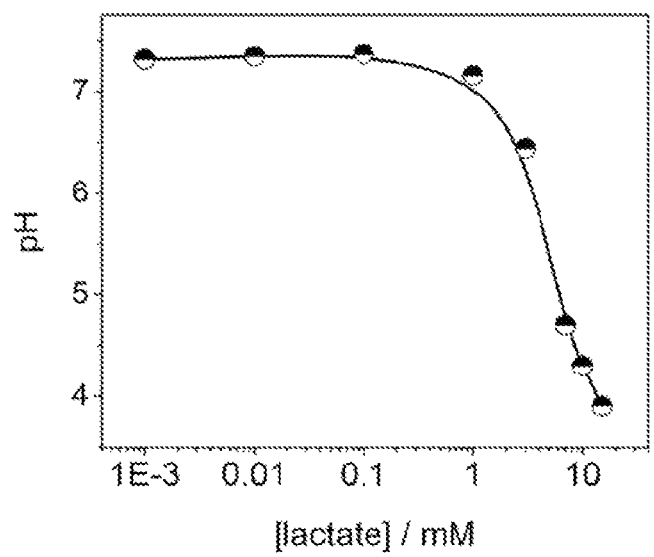
FIGS. 16A and 16B are graphs showing the effect of pH on the CV curves of the P90 film.
Figure 16B:
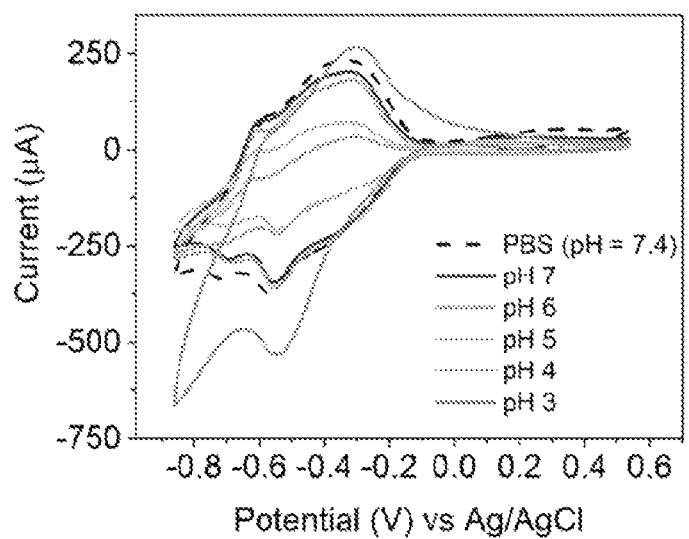

The cyclic voltammetry (CV) curves show footprints of the interactions and the electronic communication between the enzyme and the film (FIG. 14A, compare PBS; P90 only, with +LOx; upon enzyme addition). The CV curve of P90 in PBS is characterized by two reversible redox couples (FIG. 14B). The associated redox peaks are attributed to ET processes along the chain where the negative charge is mainly localized on the carbonyl oxygens of the NDI unit (Trefz, et al., *J. Phys. Chem. C*, 40:22760-22771 (2015)). The enzyme addition causes an increase both in the reduction and in the oxidation peak currents. No new feature is observed possibly due to the inherently complex CV curve of P90, while the oxidation peak shifts slightly toward more positive voltages (FIGS. 14A and 14B). The increase in the redox peak amplitudes can be attributed to the activity of flavin mononucleotide (FMN), the catalytic site of LOx (Suzuki, et al., *Phys. Chem. Chem. Phys.*, 12:10081-10087 (2010); Garjonyte, et al., *Bioelectrochemistry*, 61:39-49 (2003)). When lactate is added into the solution and is oxidized by LOx, an increase in the cathodic current is observed, as well as a shift of the peak potentials, which is more prominent as the lactate concentration increases (FIG. 14A). The electrocatalytic reactions occurring during the enzymatic sensing of lactate are described in FIG. 15 (Freire, et al., *J. Braz. Chem. Soc.*, 14:230-243 (2003)). These changes can be related to a local pH decrease, resulting from the H+ produced upon the enzymatic reaction and/or because of the high amount of lactate present in the solution (see FIG. 16A for the pH of the solution in the presence of enzymatic reactions with different amounts of lactate). The net effect of pH on the electrochemical behavior of the P90 film was investigated (FIG. 16B). With the decrease of solution pH from 7.4. to 5, both the cathodic and anodic peak potentials shift slightly toward positive potentials, accompanied by a decrease in their magnitudes. Only below pH 4 an increase in the peak amplitudes was observed, suggesting the participation of $H^+$ to dope the polymer. Therefore, $H^+$ evolution in the solution seems to be responsible for the shift of the redox peak potentials but does not play a major role in generating current, at least for lactate concentrations below 15 mM (pH<4). As such, the observed changes in the CV curve of P90 in FIG. 14A can be attributed to a synergistic effect of ET and a local pH decrease, while the contribution of the latter is pronounced for high lactate concentrations.

Figure 17A:
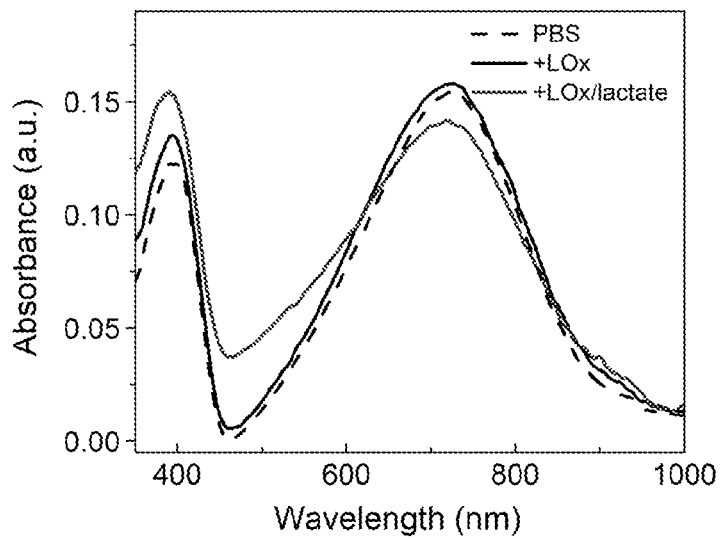
FIGS. 17A and 17B are graphs of UV-vis-NIR spectra.
Figure 17B:
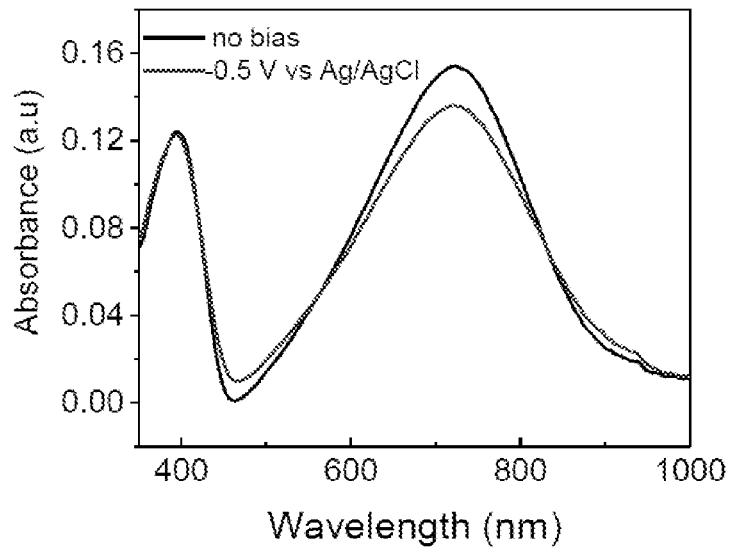
Figure 18:
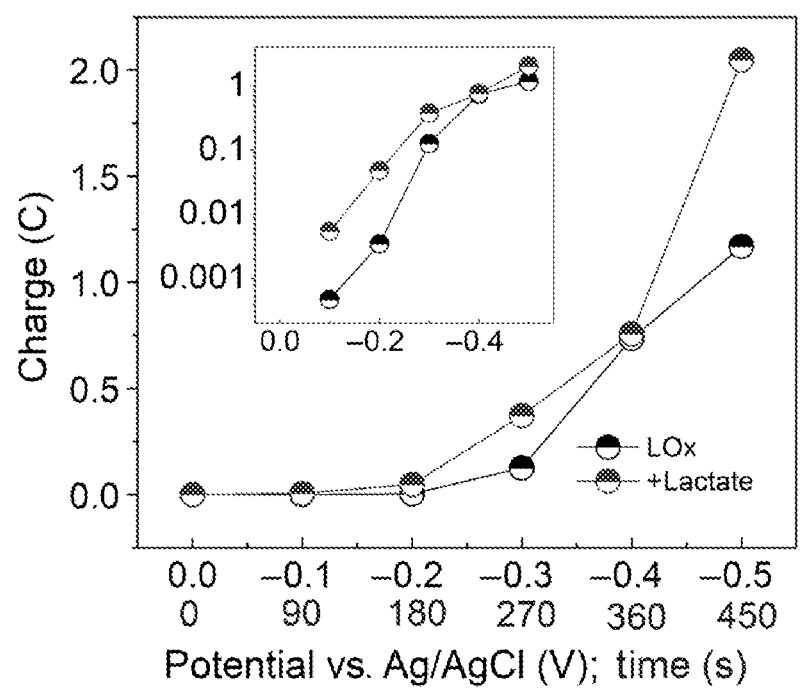
FIG. 18 are graphs showing the number of charges generated by the P90 film while a reduction potential (−0.5 V) was applied using an Ag/AgCl electrode immersed in the same solution as in FIG. 17A. The red curve represents the current generated in the co-presence of lactate and LOx in the solution. The inset shows the same plot, this time in semilogarithmic scale, magnifying the current generated at low voltages.

The ultraviolet-visible-near-infrared (UV-vis-NIR) absorbance spectrum of the P90 film in PBS solution containing LOx illustrates these interactions from another aspect (FIG. 17A). The changes in the spectrum that occur upon enzymatic reaction are comparable to those observed when the film is electrochemically doped by electrolyte cations (FIG. 17B). When lactate is added to the solution containing LOx, the absorbance peaks between 350 and 550 nm increase in intensity, with a subsequent decrease in the broader energy transition between 550 and 850 nm, which is attributed to an intramolecular charge transfer complex. These spectral changes suggest doping of the polymer film upon enzymatic reaction. The electrons produced in the reaction are efficiently transferred to the conjugated backbone, increasing the charge carrier density and hence the conductivity of the copolymer, even at voltages as low as −0.1 V (versus Ag/AgCl), which is below the reduction peak of the copolymer (FIG. 18). It is worthy to note that, in response to 10 mM lactate, the OECT channel generates three orders of magnitude higher current density compared to the output of this macroscale electrode (biased at −0.5V with respect to the reference electrode), highlighting the gain that the transistor circuit provides.

Example 9. The n-Type OECT Allows for Highly Specific Lactate Detection

Materials and Methods

Figure 19:
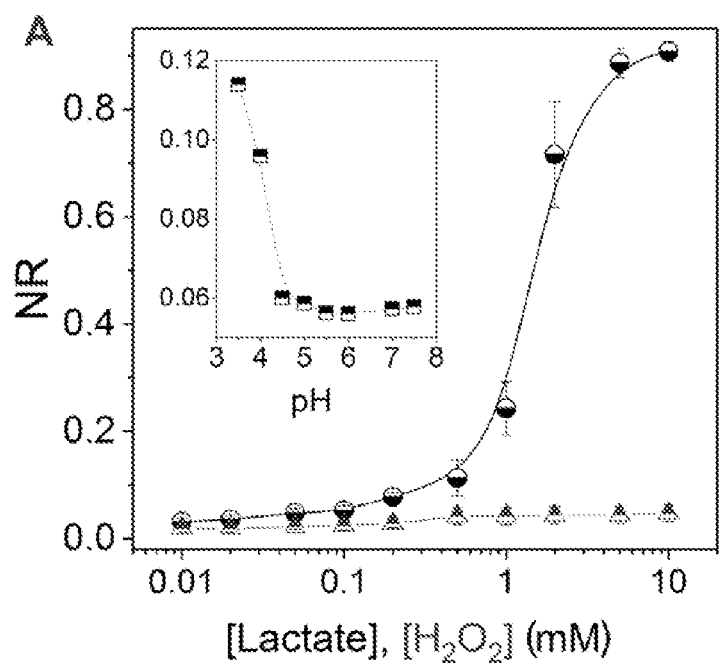
FIG. 19 are graphs of NR of the OECT to $H_2O_2$ (red triangles) and to lactate in the presence of LOx (black circles). The inset shows the sensitivity of the device to pH. The pH was adjusted using HCl and measured with an external pH electrode. The plot shows that the sensor cannot catalyze $H_2O_2$ oxidation and exhibits negligible response to changes in pH. Error bars represent the standard deviation from four measurements on two devices.
Figure 20:
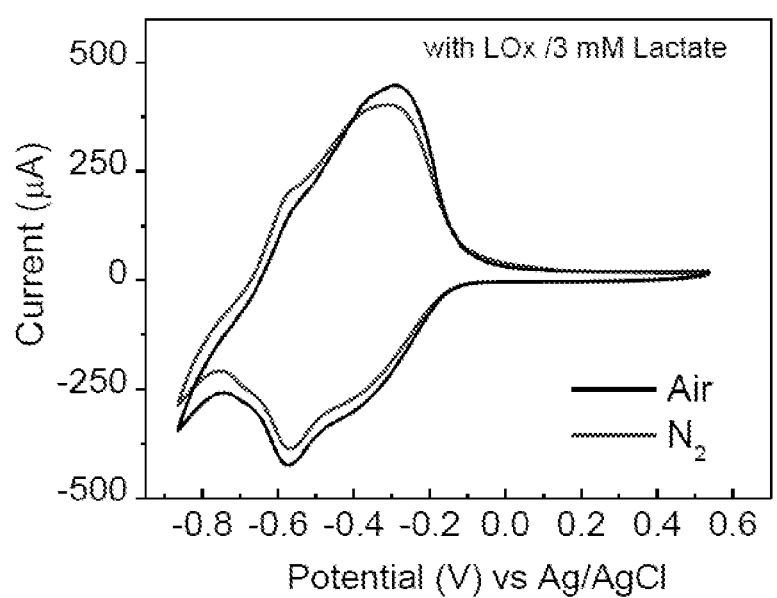
FIG. 20 shows CV curves of the P90 film in air (black) and $N_2$ (red) saturated PBS solution to demonstrate the effect of air on the reaction of lactate with LOx-functionalized P90. The solution includes LOx and 3 mM of lactate.

To rule out the possibility of P90 exhibiting inherent catalytic activity toward $H_2O_2$, the device sensitivity to $H_2O_2$ was tested. The device sensitivity to pH was also evaluated.
Results
Generally, for oxidases (such as LOx) where the cofactor is not sufficiently wired to the electrode and in the absence of an ET mediator, the diffusing molecular $O_2$ sequesters the electrons from the reduced cofactor and is converted to hydrogen peroxide (H2O2) (FIG. 15) (Pappa, et al., *Trends in Biotechnology*, 36(1):45-59 (2017)). To rule out the possibility of P90 exhibiting inherent catalytic activity toward $H_2O_2$, the device sensitivity to $H_2O_2$ was tested. FIG. 19 shows the device response to cumulative concentrations of $H_2O_2$, corresponding to the lactate concentrations tested in this study. The negligible change in channel conductance with $H_2O_2$ further confirms the selectivity of the sensor to lactate and that the ET from the enzyme to the film governs the device operation. Likewise, no significant differences in the electrochemical behavior of the system recorded in air-saturated PBS compared to that in deoxygenated PBS was observed (FIG. 20). In air, only slightly higher reduction (and oxidation) currents can be observed because of the diffusing $O_2$ that acts as an electron acceptor competing with P90.

Figure 21:
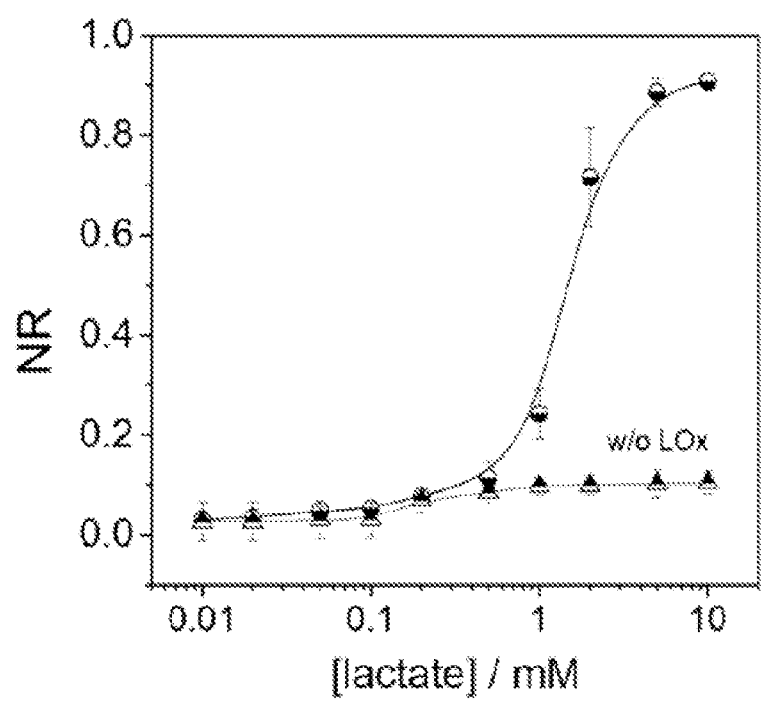
FIG. 21 are graphs of the device response to lactate in the presence (circles) and in the absence (triangles) of the enzyme, LOx.

Moreover, the sensitivity of the device to detect lactate is specific to its oxidation by the enzyme and not due to a decrease in pH of the solution (for example, $H^+$ doping). The decrease in solution pH, adjusted via HCl additions or an increase in lactate concentration, does not have a major influence in the normalized response (NR) of the OECT (see the inset of FIG. 19 and FIG. 21).

Figure 22:
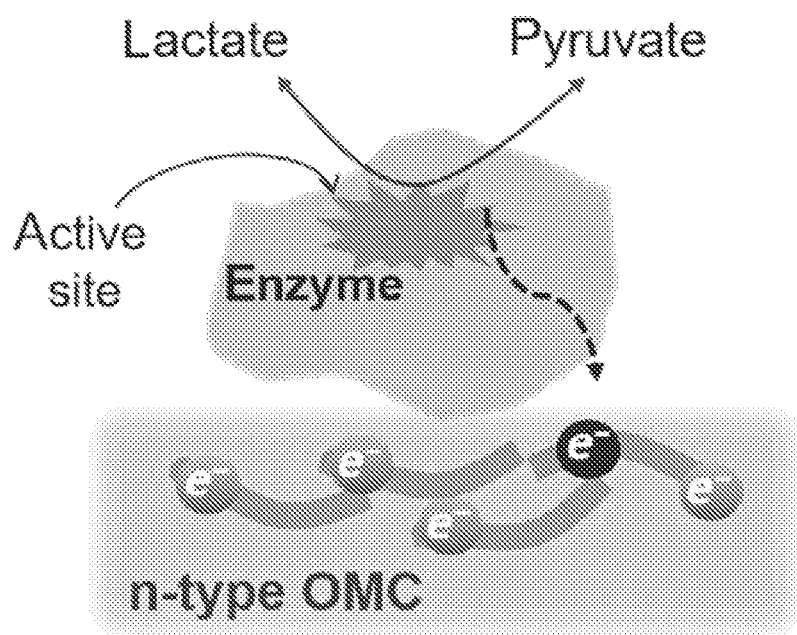
FIG. 22 is a schematic showing the proposed mechanism of lactate sensing based on the direct ET from the enzyme to the n-type OMC.

Together, it is concluded that the enzyme is efficiently anchored to the surface of the P90 film, presumably because of interactions with ethylene glycol side chains (Al-Ani, et al., *Polymers*, 9:343 (2017)). As such, it has a good electrochemical contact with the redox-active copolymer; that is, the electrons generated from the enzymatic reaction can be transferred from the FMN to the polymer backbone (FIG. 22). The NDI units of the copolymer act not only as electron-transporting conjugated segments but also as redox centers, capable of switching between the neutral and reduced state, thus obviating the need for a mediator (Rathee, et al., *Biochem. Biophys. Rep.*, 5:35-54 (2016)).

Figure 23A:
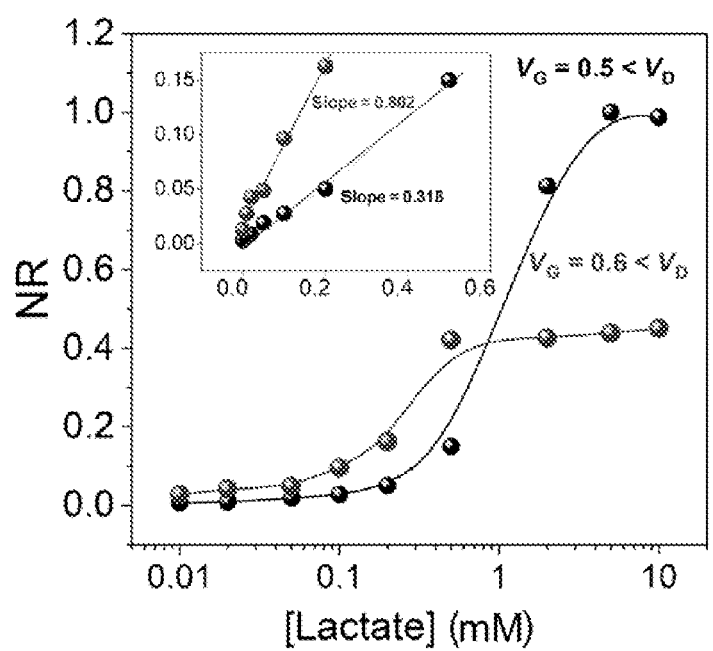
FIGS. 23A-23C show the normalized calibration curves of the device operated under different biasing conditions at the gate electrode for a $V_D$ fixed at 0.7 V (FIG. 23A), a schematic showing the distribution of electrolyte potential at the critical interfaces (gate/electrolyte and channel/electrolyte) in the presence of the enzymatic reaction under different relative biasing conditions (FIG. 23B), and the device response to lactate operated at a $V_G$ of 0.5 V and $V_D$ of 0.7 V (black), or at $V_G$ of 0.7 V and $V_D$ of 0.5 V (red) (FIG. 23C). The insets of FIGS. 23A and 23C show the response of the device to lactate represented in linear scale, with the slope indicating the sensitivity of the device.

Example 10. The Sensitivity of the n-Type OECT can be Tuned to the Desired Lactate Concentration Range Materials and Methods To evaluate the change of the analytical characteristics of the n-type OECT device depending on the biasing conditions, different biasing conditions at the gate electrode for a $V_D$ fixed at 0.7 V were tested.
Results
In the comparative lactate titration curves of the n-type accumulation mode OECT biosensor, the change of analytical characteristics of the device depending on the biasing conditions was shown (FIG. 23A). At a higher gate bias ($V_G$=0.6 V compared to 0.5 V), the sensor exhibits better sensitivity at the low lactate concentration regime (<1 mM) as determined from the slope of the linear calibration curve (FIG. 23A, inset). The increased sensitivity at higher gate bias can be sought to be directly correlated to the device's transconductance. At a $V_G$ of 0.6 V, the transconductance of the device is higher compared to operation at $V_G$=0.5 V (FIG. 9B). However, operating the device at high $V_G$ leads to faster saturation; that is, the sensor is no longer responsive to high concentrations of lactate (>0.5 mM). The closer to the threshold potential the device is gated, the larger the operation window, and therefore the larger the dynamic range of the sensor. Thus, by adjusting the gate potential, one can tune the sensitivity of the biosensor to the desired lactate concentration range, depending on the application demands.

Figure 23B:
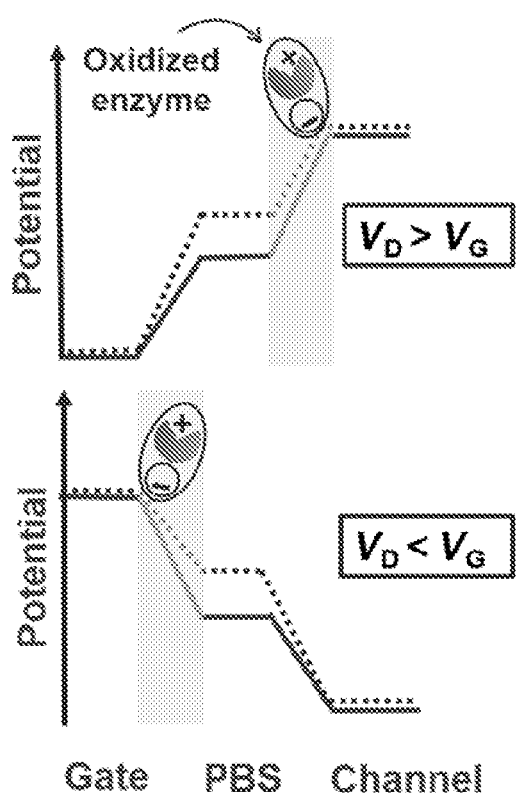
Figure 23C:
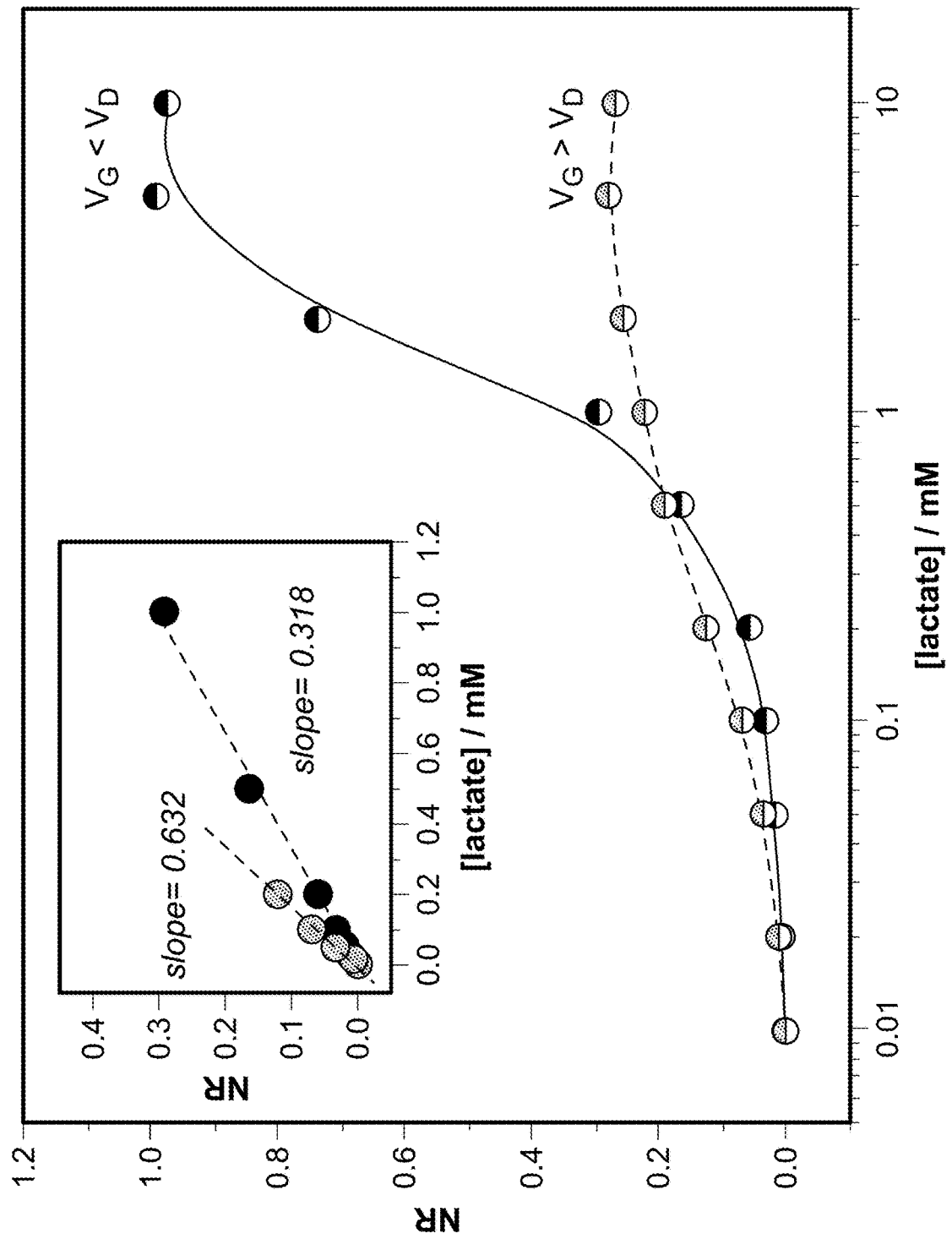

Another striking feature of this device type is the capability to drive the enzymatic reaction either at the gate or at the channel by varying the magnitude of the voltage applied at the corresponding contacts (FIG. 23B). This is implausible with the benchmark OECTs based on the p-type PEDOT:PSS because the oxidation reaction always takes place at the positively biased gate electrode rather than the negatively biased channel. When $V_G > V_D$, the gate acts as the oxidizing electrode, while the channel amplifies the sensing event (FIG. 23C). The ability to tune the polarity of the two electrodes can be beneficial in cases where the potential drop is equal at the two interfaces; that is, the gate and the channel have the same size and are made of the same material.

Overall, the n-type OECT device embodies a new concept in enzyme-based sensing where it takes advantage of the superior ion-to-electron transducing qualities of an electron-transporting (n-type) organic semiconductor and the inherent amplification properties of an ion-to-electron converting device, the OECT. The detection of lactate, a target metabolite of high biological significance in determining cellular metabolic pathways and tightly associated with critical health care conditions, was demonstrated using a fully integrated, miniaturized, easy-to-fabricate transistor platform. The polar side chains of the copolymer aid in promoting interactions with the enzyme, alleviating the need of synthetic or post-synthesis biofunctionalization that involves complex chemical approaches that aim to bring the enzyme in close proximity to the sensing surface. As such, direct electrical communication between the film and the enzyme enables mediator-free direct detection of lactate, benefiting from the electron-accepting properties of the OMC. When used in an OECT configuration, the sensing performance is greatly enhanced because of the inherent amplification of these devices.

One obvious advantage of this accumulation mode OECT compared to a conventional amperometric sensor is the inherent amplification of the signal by the channel, allowing for miniaturization. Only a few tens of micromolars of lactate causes a detectable change in the channel current. When the micrometer-scale LOx-functionalized channel is used as a resistor (simply by disconnecting the gate electrode), the change in its current with lactate is close to noise level, highlighting the role of the transistor circuit in amplifying the signal. The use of a lateral micrometer-scale gate electrode based on the n-type polymer and elimination of an external reference electrode allow for straightforward adaptation of this device type into different geometries and forms and, thus, greatly expand the application scope. Furthermore, it has been shown that controlling the operation conditions not only fine-tunes the device's analytical performance but also determines where the redox reactions take place, without the need to redesign de novo.

One evident benefit of this mode of operation is its compatibility with spatially resolved multi parametric sensing based on a single device platform including a common gate electrode and channels functionalized with different enzymes.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. An n-type polymer based electrochemical device for metabolite sensing comprising:
   one or more source electrodes;
   one or more drain electrodes;
   one or more channels which comprise (a) one or more n-type polymers and (b) one or more enzymes; and
   a gate electrode formed of an electrode material capable of conducting an electric current, wherein the gate electrode further comprises (a) one or more n-type polymers and (b) one or more enzymes, wherein the one or more n-type polymers and one or more enzymes are coated on a surface of the electrode material, and wherein the one or more n-type polymers are in physical contact with the one or more enzymes, allowing direct electron transfer therebetween;
   wherein the source electrodes and drain electrodes are electrically connected by the one or more channels, and wherein the electrochemical device is an organic electrochemical transistor.

2. The electrochemical device of claim 1 further comprising:
   (a) a supporting substrate, wherein the one or more source electrodes, the one or more drain electrodes, and the gate electrode are patterned on the supporting substrate; or (b) an electron mediator, or a combination thereof.

3. The electrochemical device of claim 2, wherein the supporting substrate is glass, polyethylene terephthalate, polyethylene naphthalene dicarboxylate, polyethylene, polypropylene, polycarbonate, paper, coated paper, resin-coated paper, paper laminates, paperboard, or corrugated board.

4. The electrochemical device of claim 1, wherein: (a) the one or more source electrodes, the one or more drain electrodes, and the gate electrode are in planar configuration, (b) the one or more n-type polymer is a structure-modified n-type polymer to introduce polar groups; or (c) the electrochemical device comprises a plurality of independently addressable source and drain electrodes, a common gate electrode, and corresponding channels, or a combination thereof.

5. The electrochemical device of claim 4, wherein the polar group is lysine.

6. The electrochemical device of claim 5, wherein the one or more n-type polymer is P90.

7. The electrochemical device of claim 4, wherein the corresponding channels each comprise a different enzyme.

8. The electrochemical device of claim 1, wherein the one or more n-type polymer is selected from the group consisting of N2300, P (NDI-T2), poly (diketopyrrolopyrrole) (DPP), poly(benzimidazobenzophenanthroline), poly(2,5-di (3,7-dimethyloctyloxy) cyanoterephthalylidene), poly(2,5-di(hexyloxy) cyanoterephthalylidene), poly(5-(3,7-dimethyloctyloxy)-2-methoxy-cyanoterephthalylidene), poly(2,5-di(octyloxy) cyanoterephthalylidene), and poly(5-(2-ethylhexyloxy)-2-methoxy-cyanoterephthalylidene).

9. The electrochemical device of claim 1, wherein the one or more enzymes are selected from the group consisting of glucose oxidase, glucose dehydrogenase, alcohol dehydrogenase, aldehyde dehydrogenase, formate dehydrogenase, formaldehyde dehydrogenase, lactic dehydrogenase, lactose dehydrogenase, lactate oxidase, cholesterol oxidase, tyrosinase, and pyruvate dehydrogenase.

10. The electrochemical device of claim 1, wherein the gate electrode has a dimension between 100 μm$^2$ and 250000 μm$^2$; the length of the one or more channels are is between 1 μm and 1000 μm; the width of the one or more channels are is between 1 μm and 1000 μm; or a dimension of the electrochemical device is between 1000 and 1000000 μm$^2$, or a combination thereof.

11. The electrochemical device of claim 1, wherein the electrochemical device is stable for 6 months.

12. The electrochemical device of claim 1, wherein the electrochemical device does not contain a reference electrode.

13. A method of detecting one or more metabolites using the electrochemical device of claim 1, comprising contacting the electrochemical device with an electrolyte solution, wherein the electrolyte solution is in electrical contact with the one or more channels and the gate electrode, and wherein the electrolyte solution comprises the one or more metabolites: (a) applying a gate potential ($V_G$); and (b) monitoring changes of a source-drain current ($I_D$) that flows through the one or more channels that connect the one or more source electrodes and the one or more drain electrodes.

14. The electrochemical device of claim 13, wherein the electrolyte solution is a buffer, a biological fluid, or a combination thereof.

15. The method of claim 13, wherein: (a) the $I_D$ increases with increasing concentration of the metabolites; (b) the gate potential equal to or higher than a threshold voltage; or (c) wherein the reaction between the one or more enzymes on the one or more channels and/or the gate electrode and the one or more metabolites produces electrons which are directly transferred to the one or more n-type polymers, or a combination thereof.

16. The method of claim 15, wherein the threshold voltage is 0.5 V.

17. The method of claim 13, wherein the one or more metabolites are capable of reacting with the enzymes on the one or more channels and/or the gate electrode.

18. The method of claim 17, wherein the one or more metabolites are selected from the group consisting of glucose, glucose-1, D-glucose, L-glucose, glucose-6-phosphate, ammonia, methanol, ethanol, propanol, isobutanol, butanol and isopropanol, allyl alcohols, aryl alcohols, glycerol, cholesterol, propanediol, mannitol, glucoronate, aldehyde, carbohydrates, lactate, lactate-6-phosphate, D-lactate, L-lactate, fructose, galactose-1, galactose, aldose, sorbose, mannose, glycerate, coenzyme A, acetyl Co-A, malate, isocitrate, formaldehyde, acetaldehyde, acetate, citrate, L-gluconate, beta-hydroxysteroid, alpha-hydroxysteroid, lactaldehyde, testosterone, gluconate, fatty acids, lipids, phosphoglycerate, retinal, estradiol, cyclopentanol, hexadecanol, long-chain alcohols, coniferyl-alcohol, cinnamyl-alcohol, formate, long-chain aldehydes, pyruvate, butanal, acryl-CoA, steroids, amino acids, favin, NADH, $NADH_2$, NADPH, $NADPH_2$, and hydrogen.

19. The method of claim 13 further comprising applying a drain voltage.

* * * * *